(12) United States Patent
Kahn et al.

(10) Patent No.: US 7,424,399 B2
(45) Date of Patent: Sep. 9, 2008

(54) SYSTEMS AND METHODS FOR FLUID QUALITY SENSING, DATA SHARING AND DATA VISUALIZATION

(75) Inventors: Malcolm R. Kahn, Franklin Lakes, NJ (US); Uwe Michalak, Ypsilanti, MI (US); Dimitris Papageorgiou, Ann Arbor, MI (US)

(73) Assignee: GE Analytical Instruments, Inc., Boulder, CO (US)

( * ) Notice: Subject to any disclaimer, the term of this patent is extended or adjusted under 35 U.S.C. 154(b) by 44 days.

(21) Appl. No.: 11/450,923

(22) Filed: Jun. 9, 2006

(65) Prior Publication Data

US 2007/0050157 A1     Mar. 1, 2007

Related U.S. Application Data

(60) Provisional application No. 60/689,257, filed on Jun. 10, 2005.

(51) Int. Cl.
G06F 11/00    (2006.01)
(52) U.S. Cl. .............................. 702/188; 702/25; 702/50
(58) Field of Classification Search .................... 702/25, 702/50, 188
See application file for complete search history.

(56) References Cited

U.S. PATENT DOCUMENTS

| 4,649,515 A | 3/1987 | Thompson et al. |
|---|---|---|
| 4,743,954 A | 5/1988 | Brown |
| 4,766,550 A | 8/1988 | Byers et al. |
| 4,830,757 A | 5/1989 | Lynch et al. |
| 4,833,622 A | 5/1989 | Barto et al. |
| 4,849,098 A | 7/1989 | Wilcock et al. |
| 4,886,590 A | 12/1989 | Tittle |
| 4,943,161 A | 7/1990 | Michaelis et al. |
| 4,943,929 A | 7/1990 | Simonoff |
| 4,967,337 A | 10/1990 | English et al. |
| 5,102,526 A | 4/1992 | Brown et al. |
| 5,120,421 A | 6/1992 | Glass et al. |
| 5,203,984 A | 4/1993 | Sakai et al. |
| 5,239,483 A | 8/1993 | Weir |
| 5,394,543 A | 2/1995 | Hill et al. |

(Continued)

FOREIGN PATENT DOCUMENTS

EP    1197753 A2    4/2002

(Continued)

OTHER PUBLICATIONS

Crossbow-water, Internet document retrieved on Mar. 27, 2004, retrieved from http://www.crossbow-water.com/os.html, 45 pages.

(Continued)

*Primary Examiner*—Bryan Bui
*Assistant Examiner*—Stephen J Cherry
(74) *Attorney, Agent, or Firm*—GE Global Patent Operation

(57) ABSTRACT

A service provider receives fluid test data generated from multiple different entities and permits authorized users affiliated with the different entities, as well as others, to visualize information associated with that data to via the Internet using graphical computer interfaces at respective computers. The fluid test data can be gathered using portable sensor units equipped with GPS and wireless communication to transmit the fluid test data and geographical information to the service provider.

43 Claims, 35 Drawing Sheets

U.S. PATENT DOCUMENTS

| | | |
|---|---|---|
| 5,417,835 A | 5/1995 | Brown et al. |
| 5,492,632 A | 2/1996 | Reber |
| 5,494,573 A | 2/1996 | Schoenmeyr et al. |
| 5,504,692 A | 4/1996 | Cardner |
| 5,525,297 A | 6/1996 | Dinger et al. |
| 5,607,566 A | 3/1997 | Brown et al. |
| 5,608,171 A | 3/1997 | Hunter et al. |
| 5,631,744 A | 5/1997 | Takeuchi et al. |
| 5,674,397 A | 10/1997 | Pawlak et al. |
| 5,696,696 A | 12/1997 | Gunther et al. |
| 5,724,254 A | 3/1998 | Millett et al. |
| 5,737,519 A | 4/1998 | Abdelnour et al. |
| 5,748,495 A | 5/1998 | Arita et al. |
| 5,832,410 A | 11/1998 | Lin et al. |
| 5,832,411 A | 11/1998 | Schatzmann et al. |
| 5,835,724 A | 11/1998 | Smith |
| 5,861,303 A | 1/1999 | Barshter et al. |
| 5,865,718 A | 2/1999 | Chan |
| 5,865,991 A | 2/1999 | Hsu et al. |
| 5,905,570 A | 5/1999 | White et al. |
| 5,925,240 A | 7/1999 | Wilkins et al. |
| 5,966,683 A | 10/1999 | Millett et al. |
| 5,970,426 A | 10/1999 | Mandel et al. |
| 5,976,466 A | 11/1999 | Ratner et al. |
| 5,993,662 A | 11/1999 | Garr et al. |
| 6,012,152 A | 1/2000 | Douik et al. |
| 6,023,223 A | 2/2000 | Baxter, Jr. |
| 6,042,788 A | 3/2000 | De Wit et al. |
| 6,061,603 A | 5/2000 | Papadopoulos et al. |
| 6,074,539 A | 6/2000 | Deininger et al. |
| 6,099,735 A | 8/2000 | Kelada |
| 6,123,820 A | 9/2000 | Bergkuist et al. |
| 6,208,940 B1 | 3/2001 | Kram et al. |
| 6,236,941 B1 | 5/2001 | Kram et al. |
| 6,245,224 B1 | 6/2001 | Enoki et al. |
| 6,290,908 B1 | 9/2001 | Fukunaga et al. |
| 6,305,944 B1 | 10/2001 | Henry et al. |
| 6,317,639 B1 | 11/2001 | Hansen |
| 6,317,694 B1 | 11/2001 | Kram et al. |
| 6,332,110 B1 | 12/2001 | Wolfe |
| 6,356,205 B1 | 3/2002 | Salvo et al. |
| 6,370,448 B1 | 4/2002 | Eryurek |
| 6,387,329 B1 | 5/2002 | Lewis et al. |
| 6,389,331 B1 | 5/2002 | Jensen et al. |
| 6,398,930 B2 | 6/2002 | Fukunaga et al. |
| 6,444,172 B2 | 9/2002 | Fukunaga et al. |
| 6,458,257 B1 | 10/2002 | Andrews et al. |
| 6,523,426 B1 | 2/2003 | Vincent et al. |
| 6,536,272 B1 | 3/2003 | Houston et al. |
| 6,560,543 B2 | 5/2003 | Wolfe et al. |
| 6,591,166 B1 | 7/2003 | Millett et al. |
| 6,607,668 B2 | 8/2003 | Rela |
| 6,625,548 B2 | 9/2003 | Babel |
| 6,626,042 B2 | 9/2003 | Havlena |
| 6,670,810 B2 | 12/2003 | Duncan et al. |
| 6,677,861 B1 | 1/2004 | Henry et al. |
| 6,738,728 B2 | 5/2004 | Jacquez |
| 6,798,347 B2 | 9/2004 | Henry et al. |
| 6,836,737 B2 | 12/2004 | Petite et al. |
| 6,839,597 B2 | 1/2005 | Hattori et al. |
| 6,845,336 B2 | 1/2005 | Kodukula et al. |
| 6,873,916 B2 | 3/2005 | Kolosov et al. |
| 6,915,211 B2 | 7/2005 | Kram et al. |
| 6,936,156 B2 | 8/2005 | Smith et al. |
| 6,954,701 B2 | 10/2005 | Wolfe |
| 6,999,898 B2 | 2/2006 | King et al. |
| 7,100,427 B2 | 9/2006 | Kahn et al. |
| 7,104,115 B2 | 9/2006 | Kahn et al. |
| 7,189,314 B1 | 3/2007 | Pace ................... 204/412 |
| 2001/0020195 A1 | 9/2001 | Patel et al. |
| 2001/0053992 A1 | 12/2001 | Eto et al. |
| 2002/0019725 A1 | 2/2002 | Petite et al. |
| 2002/0023479 A1 | 2/2002 | Burge et al. |
| 2002/0130069 A1 | 9/2002 | Moskoff |
| 2002/0133270 A1 | 9/2002 | Hung et al. |
| 2002/0142477 A1 | 10/2002 | Lewis et al. |
| 2003/0177851 A1 | 9/2003 | Henry et al. |
| 2004/0006513 A1 | 1/2004 | Wolfe |
| 2004/0138840 A1 | 7/2004 | Wolfe et al. |
| 2004/0144163 A1 | 7/2004 | Kram et al. |
| 2004/0166548 A1 | 8/2004 | Sullivan et al. |
| 2005/0066711 A1 | 3/2005 | Discenzo |
| 2005/0228688 A1* | 10/2005 | Visser et al. ................... 705/1 |
| 2005/0251366 A1 | 11/2005 | Kahn et al. |
| 2005/0251367 A1 | 11/2005 | Kahn et al. |
| 2006/0020427 A1 | 1/2006 | Kahn et al. |

FOREIGN PATENT DOCUMENTS

| | | |
|---|---|---|
| GB | 2131169 A | 6/1984 |
| WO | WO 01/80494 | 10/2001 |

OTHER PUBLICATIONS

WaterTrax Agency Service (brochure), 2003, 2 pages, retrieved from the Internet on Aug. 12, 2005 at http://www.watertrax.com/pdf/WaterTrax_Agency_Service.pdf.

WaterTrax Utility Service (brochure), 2003, 2 pages, retrieved from the Internet on Aug. 12, 2005 at http://www.watertrax.com/pdf/WaterTrax_Utility_Service.pdf.

Richard B. Brown, *Solid-State Liquid Chemical Sensor Testing Issues*, Proceedings of the International Test Conference, 2000, p. 1135, IEEE.

Hyo Jung Yoon et al., *Solid-state ion sensors with a liquid junction-free polymer membrane-based reference electrode for blood analysis*, Sensors and Actuators B 64, 2000, pp. 8-14, Elsevier.

Water Recirculation Project, Northwest Fisheries Science Center National Marine Fisheries Service (NOAA), Northwest Fisheries Science Center, http://www3.nwfsc.noaa.gov/recirc, Internet document dated Oct. 16, 2002, 3 pages.

NWFSC Water Recirculation Project: Data Acquisition and Web Display, Northwest Fisheries Science Center, http://www3.nwfsc.noa.gov/recirc/scripting.html, Internet document dated Oct. 16, 2002, 3 pages.

Thomas M. Scott and Michael B. Rust, *A Computer Automated Cold Water Recirculating System For Aquaculture Research*, copy of paper presented at Success and Failures in Commercial Recirculating Aquaculture Conference, Jul. 19-21, 1996, Virginia Tech.University.

Remote Measurement Systems, Case Studies—Fisheries/Aquaculture Remote, Measurement Systems Inc., http://www.measure.com/casestud-fish.html, Internet document dated Oct. 16, 2002, 4 pages.

Soreide, et al., *Mosaic access to realtime data from the TOGA-TAO array of moored buoys*, Internet document from web site Equatorial Pacific, dated Oct. 16, 2002, pp. 1-8.

Michael Franklin and Stan Zdonik, "*Data In Your Face*": Push Technology in Perspective, Sigmod Record, vol. 27, Issue 2, Jun. 1998, pp. 516-519.

A.D. McKinnon and C.W. Hubbard, *Automating Communications with and Developing User Interfaces for Remote Data Acquisition and Analysis Systems*, IEEE Transactions on Nuclear Science, vol. 44, No. 3, pp. 1062-1064, Jun. 1997.

Smart Plant Works: Outsourcing ASP-Style, undated, 4 pages.

The Aqua Trend Network—The New Standard in High Speed Ddata Management (Product Brochure), 2000, 4 pages, Hach Company.

WebHMI—Web-Based Real-Time Automation Software (Product Brochure), 2002, 4 pages, Iconics, Inc.

Wonderware Suite Voyager 2.0—Plant Intelligence Portal (Product Brochure), Jul. 2003, 5 pages, Invensys Systems, Inc.

Ingo Cyliax, "*Remote Internet Data Logging and Sensing*", Circuit Cellar Ink Magazine, Embedded, PC, PC/104 Quarter 104, Nov. 1997, pp. 53-59.

Sanz-Bobi, M.A., et al., "*Control and diagnosis of water chemistry in the water-stream and water make-up in a fossil fuelled power plant,*" Electrical Power & Energy Systems, vol. 16, No. 4, 1994, pp. 251-258.

Asakura, Y., et al., "*Structural Material Anomaly Detected System Using Water Chemistry Data,*" J. Nuclear Sci. & Tech., 29(11), Nov. 1992. pp. 1120-1126.

Igarashi, H., et al., "*Development of Water Chemistry Diagnostic System for BWRs Using Fuzzy Reasoning,*" J. Nuclear Sci. & Tech., 31(10), Oct. 1994, pp. 1023-1037.

Kneile, "*Wring More Information Out of Plant Data*" Chemical Engineering, Mar. 1995, pp. 110-116.

Remote Measurement Systems, "Posting Real-Time Measurement to the Web", Home Energy, Internet document from web site Posting Real-Time Measurements to Web Page, dated Oct. 16, 2002, pp. 1-5.

EPRI chemWORKS™ Users Manual vols. 1 and 2, 1995, Electric Power Research Institute, Inc. (EPRI).

Sensicore, the new math for water profiling (Product Brochure). May 2004, 4 pages, Sensicore, Inc.

International Search Report for PCT/US06/22736, Jan. 3, 2007, Sensicore, Inc.

* cited by examiner

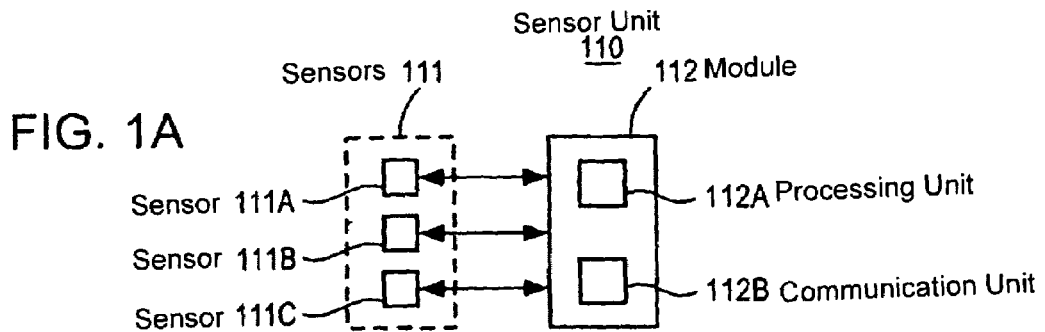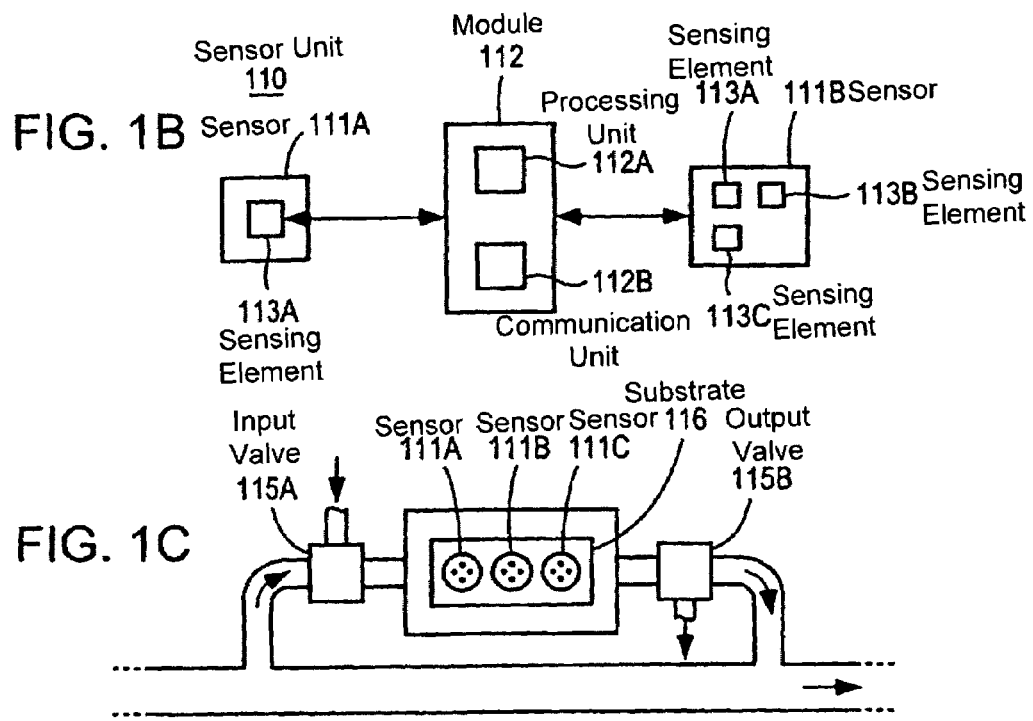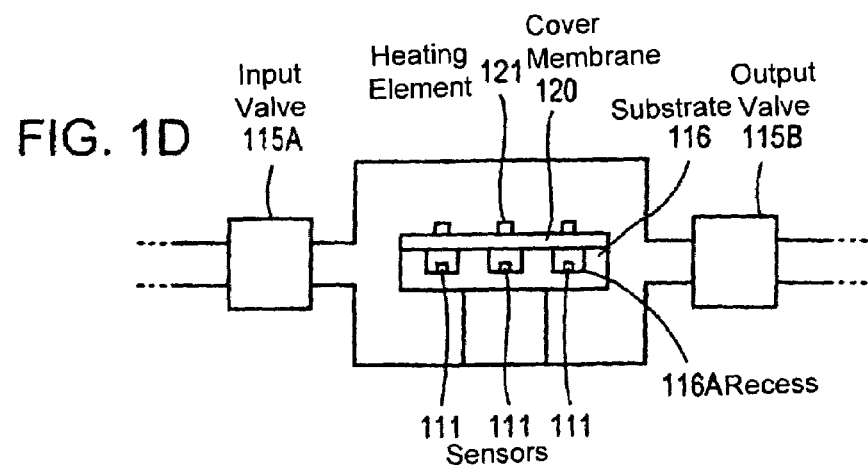

Measurement Frequency Table

Today's date: 24-Jun-2005

| Location ID | Location Name | Date of last Measurement (mm/dd/yyyy) | Location Measurement Frequency (days) | Next Measurement due in: (days) | Location Measurement Status |
|---|---|---|---|---|---|
| L1 | 114 Main | 20-Dec-2004 | 30 | -8 | Past Due |
| L3 | Fuller & Geddes | 23-Nov-2004 | 60 | -7 | Past Due |
| L2 | Plant#1 | 26-Oct-2004 | 90 | -6 | Schedule today |
| L4 | BankTwo-Plymouth | 10-Jun-2005 | 15 | -4 | Due |
| L5 | 454 Scio | 27-Dec-2004 | 30 | -3 | Due |
| L7 | Saline depot | 30-Dec-2004 | 30 | -2 | Due |
| L6 | McDonalds on State | 01-Dec-2004 | 60 | -1 | Due |
| L8 | Fire Department#11 | 02-Jun-2005 | 30 | 0 | Schedule today |
| L9 | 114 Main | 20-Dec-2004 | 30 | 1 | Due |
| L11 | Fuller & Geddes | 23-Nov-2004 | 60 | 2 | Past Due |
| L10 | Plant#1 | 26-Oct-2004 | 90 | 3 | Past Due |
| L3 | BankTwo-Plymouth | 10-Jun-2005 | 15 | 4 | Schedule today |
| L12 | 454 Scio | 27-Dec-2004 | 30 | 5 | Due |
| L14 | Saline depot | 30-Dec-2004 | 30 | 6 | Due |
| L16 | McDonalds on State | 01-Dec-2004 | 60 | 7 | Due |
| L15 | Fire Department#11 | 02-Jun-2005 | 30 | 8 | Due |
| L17 | 114 Main | 20-Dec-2004 | 30 | 9 | Past Due |
| L19 | Fuller & Geddes | 23-Nov-2004 | 60 | 9 | Past Due |
| L18 | Plant#1 | 26-Oct-2004 | 90 | 10 | Schedule today |
| L20 | BankTwo-Plymouth | 10-Jun-2005 | 15 | 10 | Due |
| L22 | 454 Scio | 27-Dec-2004 | 30 | 11 | Due |
| L21 | Saline depot | 30-Dec-2004 | 30 | 12 | Due |
| L24 | McDonalds on State | 01-Dec-2004 | 60 | 13 | Due |
| L23 | Fire Department#11 | 02-Jun-2005 | 30 | 14 | Due |
| L26 | 114 Main | 20-Dec-2004 | 30 | 15 | Past Due |
| L25 | Fuller & Geddes | 23-Nov-2004 | 60 | 16 | Past Due |
| L28 | Plant#1 | 26-Oct-2004 | 90 | 16 | Schedule today |
| L27 | BankTwo-Plymouth | 10-Jun-2005 | 15 | 17 | Due |
| L30 | 454 Scio | 27-Dec-2004 | 30 | 17 | Due |
| L29 | Saline depot | 30-Dec-2004 | 30 | 18 | Due |
| L32 | McDonalds on State | 01-Dec-2004 | 60 | 19 | Due |

*Fig. 8D*

SYSTEMS AND METHODS FOR FLUID QUALITY SENSING, DATA SHARING AND DATA VISUALIZATION

CROSS-REFERENCE TO RELATED APPLICATION

This application is related to, based upon and claims priority to U.S. Provisional Patent Application Ser. No. 60/689,257, filed Jun. 10, 2005, and entitled Systems And Methods For Fluid Quality Sensing, Data Sharing And Data Visualization, whose contents (including but not limited to the specification and drawings) are incorporated herein by reference.

The entire disclosures of U.S. patent application Ser. No. 10/840,628 entitled "Monitoring Systems and Methods for Fluid Testing", U.S. Patent Application Ser. No. 10/840,639 entitled "Fluid Monitoring Systems And Methods With Data Communication To Interested Parties," U.S. patent application Ser. No. 10/840,649 entitled "Fluid Treatment Apparatus with Input and Output Fluid Sensing," and U.S. patent application Ser. No. 10/840,650 entitled "Multi-Sensor System for Fluid Monitoring with Selective Exposure of Sensors", all filed May 7, 2004, are incorporated herein by reference.

BACKGROUND

1. Field of the Disclosure

The disclosure relates generally to sensor systems and methods for fluid monitoring. More particularly, the disclosure relates to sensor systems and methods for fluid (e.g., water) quality data gathering including on-line fluid quality monitoring by means of sensors with wired or wireless connections to a communications network (e.g., the Internet), for access and visualization of fluid quality data over the Internet via a graphical web-browser interface, and for sharing of such data via the Internet.

2. Background Information

The quality and surety of drinking water is of ever increasing importance throughout the world. Contaminants, such as toxins, biological agents, inorganic compounds and particulate matter that enter a contiguous water distribution system either naturally, or are purposely placed there as a terrorist act, have the capacity to diminish the quality of the water to an unacceptable level, and each member of the population, whether human or other life form, is at risk of exposure to water of such substandard quality. Water can become contaminated at its source, whether that be from wells, rivers, reservoirs or treatment plants, or can become contaminated once the water is introduced into a contiguous water distribution system. Regardless of its source or type, water quality degradation can have a significant detrimental health affect that can sometimes be seen quickly and often times is not recognized or detected for years or even decades.

Measures have been taken for monitoring the quality of drinking water including placing monitors at various points in the source water, in water treatment plants, and/or at selected distribution points of water distribution pipe networks within a region of a water authority, for instance. The selection, access to appropriate sites and acquisition/placement of water quality monitoring components and systems tend to be labor intensive and costly for a regional or multi-regional water authority to implement. This high cost and significant ongoing maintenance requirement for remote monitoring systems has severely limited the number of locations monitored and is the primary reason that most testing is performed on a low-volume basis by bringing "grab samples" of water back to a laboratory for testing. Several considerations are at issue: the density of testing (i.e., how many locations in a reservoir or within a city should be monitored to protect the population from exposure, e.g., each city block or within a 5-block, 10-block or 20-block area); the frequency of testing (e.g., whether taking a grab sample once a month for a given location is sufficient to protect the population); and the time delay in receiving "actionable" data about contamination that may already be affecting tens of thousands of people by virtue of the testing being done on a non-continuous basis.

Additionally, many water quality sensors create false positives, or false negatives, in determining substandard water conditions. These false positives can be expensive insofar as they require investigation and repair of a sensor node and could even result in the shut-down of a water distribution system section or, more commonly, an alert that disrupts a population's use of water. False negatives can be even more costly if hazardous conditions are not timely detected.

Further, the need for sharing of water quality measurements, particularly in real time, is of ever increasing importance. Not only do regional water authorities need real time measures of water quality to improve system performance, multiregional (e.g., county, province, state or national) water authorities desire original data whether in the form of raw data or analyzed results of the water quality in a particular water distribution region. This information can be used to assure compliance with water quality standards, for instance. This information is generally provided by the regional water authorities, which may not have sufficient incentives to provide completely candid reports. Also, in these uncertain times, real time awareness of possible or actual sabotage can be of critical importance, if only to provide assurance to the general population that the water supply is safe.

Thus, there is a need for improvements in sensing whether a municipal, industrial or even home water purification/treatment system is operating properly and providing water of a certain quality. This can be particularly important when a municipality places water treatment equipment in remote locations to selectively or more cost effectively treat water instead of treating the entire bulk water at the municipality.

Finally, there is a need to confirm the purity and surety of water sold as pure from a commercial water treatment system in order to verify manufacturers claims of providing pure water.

SUMMARY OF DISCLOSURE

Various embodiments of the present disclosure address these as well as other concerns raised by the state of the art.

A service provider receives fluid test data generated from multiple different entities and permits authorized users affiliated with the different entities, as well as others, to visualize information associated with that data to via the Internet using graphical computer interfaces at respective computers. The fluid test data can be gathered using portable sensor units equipped with GPS and wireless communication to transmit the fluid test data and geographical information to the service provider, or by stationary (e.g., permanent) sensors or by means of analyzed test results produced by laboratories or other $3^{rd}$ parties.

As another example, a graphical user interface is disclosed for monitoring fluid quality. The interface includes a geographical map, and a display of fluid test data that is overlaid on the geographical map, wherein the fluid test data was generated by a sensor unit. Contoured lines are overlaid on the geographical map to indicate equal concentrations of a fluid test parameter. A selection region is provided for user selection of fluid test parameters, and a graph region is used for displaying a graph of the selected fluid test parameters.

BRIEF DESCRIPTION OF THE DRAWINGS

The present disclosure will now be explained with reference to exemplary embodiments illustrated in the accompanying drawings to which the invention is not necessarily limited. Various advantages and other attributes of the invention will be identified or become apparent with respect to various specific embodiments, but not all embodiments within the scope of the present invention will necessarily include or have identified advantages or attributes. The scope of the invention should be determined based on recitations contained in the claims, and equivalents thereof, rather than reliance on advantages and attributes not positively recited in the claims. Further, although the term "invention" has been used in the singular, it should be recognized that more than one independent and/or distinct invention may be presented in the disclosure and claims.

FIG. 1A is a block diagram of an exemplary embodiment of a sensor unit in accordance with an embodiment of the present disclosure.

FIG. 1B is a block diagram of another exemplary embodiment of a sensor unit in accordance with another embodiment of the present disclosure.

FIG. 1C is an illustration of an exemplary embodiment of a sensor unit.

FIG. 1D is an illustration of another exemplary embodiment of a sensor unit.

DETAILED DESCRIPTION OF EXEMPLARY EMBODIMENTS

Figure 1J:
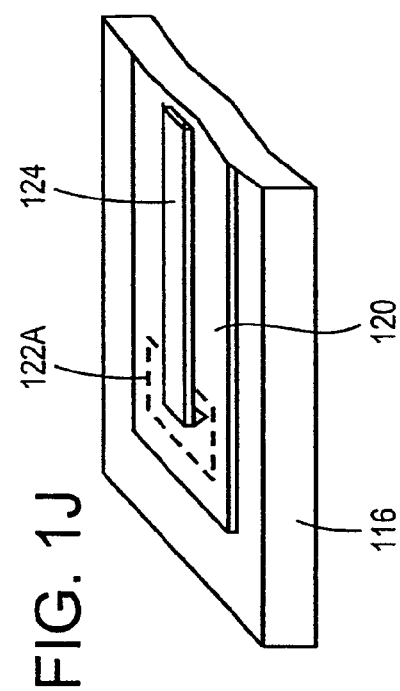
FIG. 1J is an illustration of another exemplary embodiment of a sensor unit.

For purposes of this document, the following should be understood. The term "water quality" generally relates to measures of various aspects of water or other fluids and fluids that tend to indicate the usefulness of or danger posed by a fluid including but not limited to the measure of various chemicals, chemical profiles, presence of biological agents and/or life forms, toxins, other organic and inorganic contaminants, and particulates, etc. For instance, although water distribution systems are a focus of several embodiments of the present invention, it is also possible that aspects of the present invention can be applied to monitor any fluid (gas or liquid) including those present in a distribution system, reservoir or feed source in need of monitoring. The term "confirm" should be understood to mean that additional evidence or support by another indication has been determined based on additional information, which can be of the same or a distinct type relative to the data leading to the original indication. "Distribution system" includes any system of fluid distribution (including air distribution systems such as, for example, air ducts), which in the case of water distribution, currently commonly manifest themselves as contiguous systems of pipes and/or systems of reservoirs, channels, pipes and treatment plants, but also can include less typical distribution channels such as container water, well water within a watershed or a water table, and even large bodies of water, oceans, rivers, streams and/or tributaries, or virtually anything wherein a fluid can flow from one point in the system to another, such as movement of water from one layer to another layer within a single body of water, a hallmark of which is the ability to identify the location of and communicate with sensor units within the water distribution system. Also, the phrase "same sample of fluid", "the fluid" and the like should be understood to mean any quantity of the fluid wherein the same or similar conditions are likely to exist. For example, for broad measures such as pH in a body of non-static water, all of a large pool or reservoir might be the same sample, whereas for detecting trace elements or alarming conditions, a water sample might mean only a few milliliters. The term "measuring" is not limited to embodiments wherein a numeric value or other analog or digital value is generated, but rather includes sensors and sensor elements that simply output a defined signal when a threshold (either an upper or a lower or both) is crossed. A sensor unit includes one or more sensors, sensor elements and/or sensor groups within a housing or located at a site, and includes processing and/or communication components. A sensor is a device designed to sense a parameter or parameters of a fluid and outputs a signal, typically to a processor. A sensing element is an element that forms part of a sensor and actually performs the measurement. The sensing elements of a sensor can be associated or coordinated in some fashion to perform monitoring and detection functions as a group, perhaps to determine a chemical profile of a sample. A sensor component is a generic term meaning any one of a sensor unit, sensor, or sensing element. A processing unit is a generic term meaning one or more processing units programmed at a software, firmware or hardware level, including, for example, ASIC (application specific integrated circuit). A processing unit can be multiplexed to multiple sensors or dedicated to a single sensor.

Sensors

Exemplary sensors can be selected to include any form of fluid measuring sensors, such as water quality measuring sensing elements including sensing elements for determining water temperature, water pressure, the presence or absence of any number of specific chemicals, chemical profiles and/or classes of chemicals such as for example and without limitation free chlorine ($Cl^-$), hypochlorous acid (HOCl) and hypochlorite ions ($OCl^-$), ion concentration, pH, carbon dioxide ($CO_2$), water hardness (e.g., $Ca^{2+}$), carbonate ($CO_3^{2-}$), monochloromine ($NH_2Cl$), dichloramine ($NHCl_2$), trichloramine ($NCl_3$), ammonium, nitrite, nitrate, fluoride, and/or chemical profiles, as well as determining water purity, clarity, color and/or virtually any other measurable or detectable parameter of interest with respect to water or any other fluid. Some such sensors are described in copending U.S. patent application Ser. No. 10/657,760 ("Method and Apparatus for Quantitative Analysis"), the entire disclosure of which is incorporated herein by reference. Such sensors can be used to monitor not only liquids, but also, with appropriate calibration, gases (e.g., air) as well. Such sensors can include one or more of, for example, electrodes and ion-selective membranes acting as ion-selective electrodes (ISEs), amperometric and potentiometric sensing elements that may or may not have electrode coatings on the electrode surfaces, conductivity sensing elements, temperature sensing elements, oxidation-reduction potential sensing elements, reference electrodes, oxygen sensing elements, immunosensors, DNA probes (e.g., hybridization assays with oligonucleotides) comprising appropriate coatings on electrode surfaces and a wide variety of optical sensors, to name a few. Other suitable sensor devices include those disclosed in U.S. Pat. No. 4,743,954 ("Integrated Circuit for a Chemical-Selective Sensor with Voltage Output") and U.S. Pat. No. 5,102,526 ("Solid State Ion Sensor with Silicone Membrane"), the disclosures of which are incorporated herein by reference.

Sensors for use in systems disclosed herein, such as those disclosed in copending U.S. patent application Ser. No. 10/657,760, U.S. Pat. No. 4,743,954, and U.S. Pat. No. 5,102,526, for example, can be fabricated using known lithographic, dispensation and/or screen printing techniques (e.g., conventional microelectronics processing techniques). Such techniques can provide sensors having sensing elements with micro-sized features integrated at the chip level, and can be integrated with low-cost electronics, such as ASICs (applications specific integrated circuits). Such sensors and electronics can be manufactured at low cost, thereby enabling wide distribution of such sensors to various entities, including private entities.

Exemplary sensors can be fabricated on silicon substrates or can be fabricated on other types of substrates such as, for example, ceramic, glass, $SiO_2$, or plastic substrates, using conventional processing techniques. Exemplary sensors can also be fabricated using combinations of such substrates situated proximate to one another. For example, a silicon substrate having some sensor components (e.g., sensing elements) can be mounted on a ceramic, $SiO_2$, glass, plastic or other type of substrate having other sensor components (e.g., other sensing elements and/or one or more reference electrodes). Conventional electronics processing techniques can be used to fabricate and interconnect such composite devices.

Also, a variety of other sensors, whether commercially available or not including those not yet developed, could be used within the system disclosed herein. While novel sensor units comprising various sensors are disclosed herein, other novel aspects of the present disclosure remain novel regardless of the form of sensor units. With regard to monitoring of gases such as air, any suitable sensor for detecting a target species can be used, such as, for example, electrochemical gas sensors including electrochemical sensors for detecting hydrogen cyanide as disclosed in U.S. Pat. No. 6,074,539, the entire contents of which are incorporated herein by reference.

Exemplary Monitor, Confirm and Report Systems

In one embodiment of the present disclosure shown in FIG. 1A, a system for monitoring water quality (or quality of any fluid) (330 in FIG. 3) can include a sensor unit 110 that includes a first sensor 111A and an associated processing unit 112A acting as a monitoring means for monitoring a fluid and generating a variable based on the content of a fluid. This processing unit 112A can be housed in a module 112 along with a communication unit 112B. This first sensor 111A either upon the detection of a quality in the fluid or by the measured or calculated variable associated with the fluid crossing a threshold, for instance, can generate a preliminary identifier if the variable is indicative of a detection condition. For instance, if the pH level (as the variable) or other water quality parameter rises too high or low, or the water pressure as measured by an incorporated pressure monitor drops below a threshold for instance, a preliminary identifier (e.g., a flag or a signal) is generated in this exemplary system. This preliminary identifier can trigger a second sensor 111B to begin measuring the same variable or a different variable, or to output a continuously measured result. The processing unit 112A can comprise a single processing unit or multiple processing units.

Alternatively, the second sensor 111B can be run in tandem with the first sensor 111A for testing the same sample of fluid a second time either using the same test or a different test that also is indicative of a detection condition. The results of the measures or tests are output from the processor as a confirmed result when they agree. The second sensor 111B and the processing unit 112A act as a confirming means for the first sensor or monitoring means 111A.

Alternatively, the second sensor 111B can be in the form of the first sensor 111A that is recalibrated for the second test.

Upon a positive result from the first sensor 111A in conjunction with the processing unit 112A (acting together as monitoring means) and a positive result from the second sensor 111B (or more sensors) in conjunction with the processing unit 112A (together acting as confirming means), the detection condition is communicated or reported by a communication unit 112B (acting as reporting means) to a remote communication device and/or a local indicator (e.g., a light or other form of alert on the sensor unit housing). Information regarding fluid measurement results can also be displayed on an optional display (e.g., located on the sensor unit housing). This form of sensor unit 110 thereby eliminates many false positives insofar as before a detection condition is reported, it is confirmed.

Also, more than one sensor can act as either the first and/or second sensor 111A, 111B to provide redundancy of tests or measures. In this way, if one sensor fails, another sensor acting in the same capacity acts as a back-up to reduce the chances of a false negative. Whether through detection of false positives or false negatives, or other means, a defective sensor or other sensor component can be deactivated by a processing means, for instance by simply not supplying power or not processing output from the defective sensor component.

As illustrated in the exemplary embodiment of FIG. 1A, the sensors in a sensor unit 110 can take the form of a first sensor 111A and a second sensor 111B and even more sensors 111C as circumstances warrant. Such sensors can collectively be referred to as a sensor group, which can also simply be referred to as sensor 111. Sensors of a sensor group may be physically configured together as a unit, but this is not necessary. For instance, the third sensor 111C can be provided to serve as part of the confirming means, thereby allowing the processing unit 112A to determine whether the detection condition has occurred based on a majority voting approach using data from the first sensor 111A, the second sensor 111B and the third sensor 111C, e.g., each sensor 111A-111B gets one vote or a weighted vote perhaps in the form of an analog or digital signal, and the condition indicated by a majority of such votes is reported to a remote communication device or local indicator. The third sensor 111C (or any number of additional sensors) can act as back-up sensors, or be used to further reduce false positives and/or false negatives using a majority voting technique. Such sensors can include, for example, electrodes and ion-selective membranes acting as ion-selective electrodes (ISEs), amperometric and potentiometric sensing elements that may or may not have electrode coatings on the electrode surfaces, conductivity sensing elements, temperature sensing elements, oxidation-reduction potential sensing elements, oxygen sensing elements, immunosensors, DNA probes (e.g., hybridization assays with oligonucleotides) comprising appropriate coatings on electrode surfaces and a wide variety of optical sensors, to name a few.

The sensors 111A-111C can each be made up of a single sensor element 113A, a plurality of sensor elements 113A-113C, perhaps for redundancy, or one or more sensor groups, as shown in FIG. 1B. The sensor elements 113A-113C can be of the same type or of different types to measure, for example, the same parameters for sake of redundancy and greater accuracy, or measure different aspects of a chemical or biological profile or signature. The first sensor 111A and/or the second sensor 111B can, for instance, can respectively comprise a sensing element 113A capable of measuring an ion content and a sensing element capable of measuring a chlorine content. More generally, the sensors 111A-111C can comprise at least one of an ion-selective sensing element, an amperometric sensing element, a potentiometric sensing element, a conductivity sensing element, a temperature sensing element, an oxidation-reduction potential sensing element, a chlorine sensing element, an oxygen sensing element, an immunosensor, a DNA probe and an optical sensor. The sensors 111A-111C can be provided on distinct substrates, or be provided on the same substrate 116, as shown in FIG. 1C.

The processing unit 112A and the communications unit 112B act as the reporting means for reporting a confirmed event based on processed data from the first and second sensors 111A, 111B, or any number of a plurality of sensors 111 in a sensor unit 110.

In one exemplary embodiment, each of the plurality of sensors 111A-111C is of the same type for monitoring the same parameters or profile of the fluid. In this way, if a first sensor 111A indicates false positives, the second sensor 111B would act to confirm or not confirm any detection event thereby reducing the number of reported false positives. Alternatively, the first sensor 111A may be of a more robust nature but perhaps lower sensitivity or have a broader range of detectable conditions, whereas the second sensor 111B might be more sensitive or of a limited detection range or of a special type to detect a specific substance (one-shot sensors) and under these circumstances might be invoked, for instance, only when the first sensor 111A generates a preliminary identifier indicative of a detection condition. For example, where the first sensor 111A has an array of sensing element of the types noted above, and generated a profile reading suggestive of cyanide, for example, a one-shot sensor that can specifically detect cyanide or detect smaller amounts of cyanide, can be activated or exposed. The second sensor 111B, being more sensitive or more be capable of more accurately identifying a given detection condition, would then be better able to confirm the existence of a detection event with greater certainty.

The second sensor 111B could have at least one characteristic such as greater sensitivity, more specific sensitivity, or be able to detect secondary traits of a suspected substance indicated by the preliminary identifier. In the later case there might be a plurality of second sensors 111B each associated with a given, more specific test or measure of the quality of the fluid, and activated as a group or individually based on the information contained in the preliminary identifier. The second sensor 111B could, however, be the same type of sensor as the first sensor 111A in certain embodiments.

Further, the second sensor 111B can be coupled to a mechanism to change the fluid or its environment prior to detection by the confirmation sensor. For instance, a single sensor 111A can be utilized and, upon generating a preliminary identifier, a recalibration solution can be injected by pumps, valves, microfluidics or other means, onto the sensor, wherein the recalibration solution has a known, constant parameter measurable by the sensor 111A to recalibrate the sensor 111A for a subsequent measurement. Alternatively, a reagent can be introduced into the fluid, the reagent being specific to the detection condition to change the nature of the fluid in a controlled fashion to assist in identifying the constituents of the fluid that is causing the detection condition. Enough recalibration fluid or reagent could be supplied to last the expected life of the sensor 111A, or be in the form of a replenishable supply.

For instance, as illustrated in FIG. 1C, a fluid control device such as a valve 15A is located on the input side of a senor unit 110. The valve 115A could then toggle between allowing fluid from the distribution system into the sensor unit 110 and allowing a calibration fluid into the sensor unit 110. On the output side of the sensor unit 110, a similar fluid control device such as a valve 115B can be used to remove the calibration fluid as waste, if introducing it into the monitored fluid raises potential concerns or the output fluid control device can be omitted if allowing the fluid in the sensor unit 110 to rejoin the fluid in the distribution system does not raise concerns.

The single sensor 111A may be thereby recalibrated by exposure to recalibration agent or the like, but alternatively can be simply electrically recalibrated by normalizing its response based on background conditions.

Figure 3:
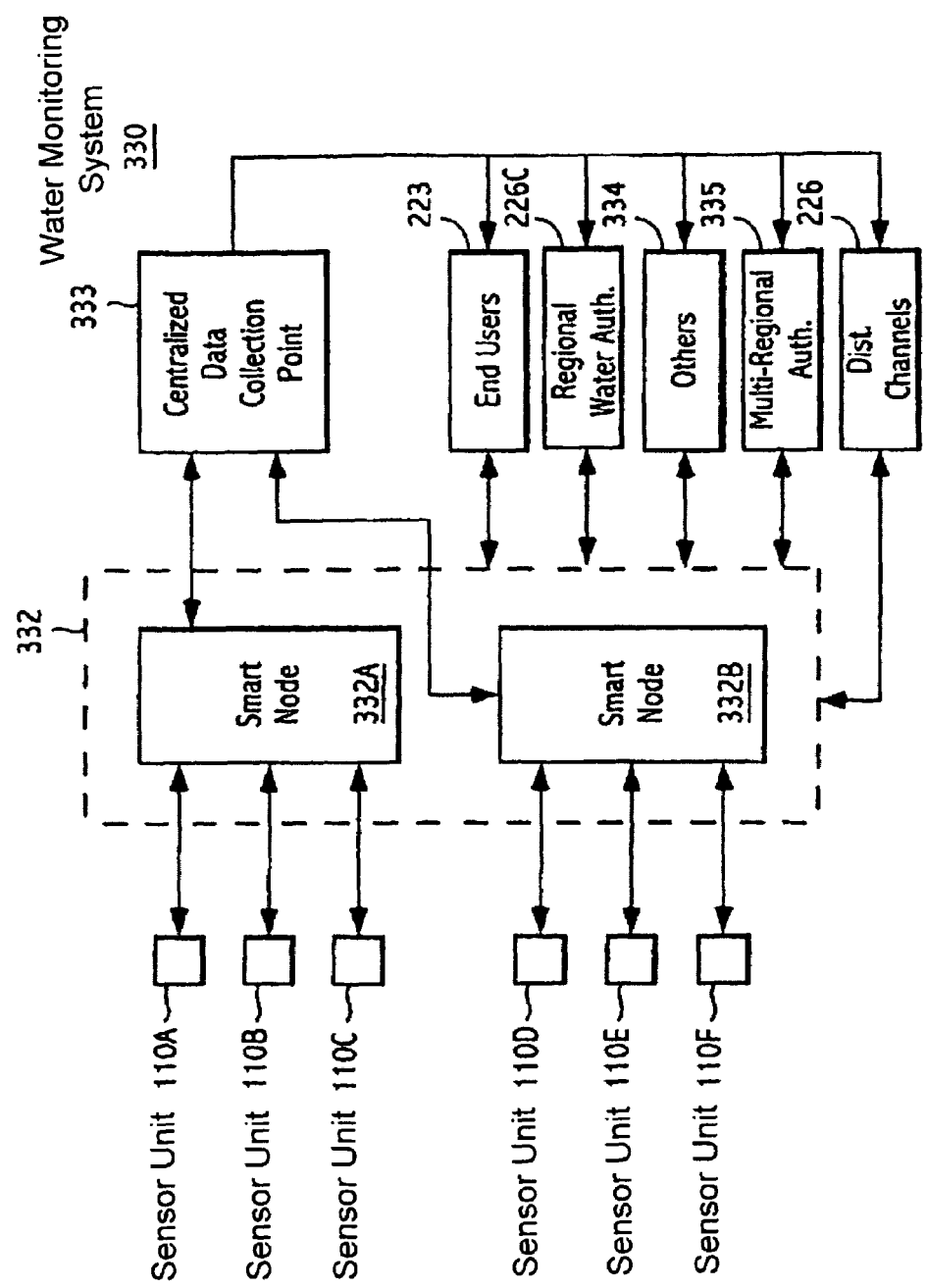
FIG. 3 is a block diagram of an exemplary data collection network, data distribution network and data analysis network in accordance with aspects of the present disclosure.

As perhaps easier to understand with respect to the fluid monitoring system of FIG. 3, one sensor can be used to calibrate another sensor. More specifically, in a network situation, a new sensor placed into the system could be used to calibrate older sensors that might have been subject to calibration drift over time. The old and new sensors would detect the same fluid either in the fluid distribution system or as reagents or calibration solutions, and the new sensor readings would be used to adjust or calibrate the older sensor. The sensors ought to be neighboring, or relatively remote, as long as the fluid being used is substantially the same in relevant ways, e.g., has the same pH, is taken from a small sample or a sample likely to have the same or uniform characteristics. The recalibration sensor merely has to be measuring a parameter that is similar enough to the sensor to be recalibrated to make the recalibration effective.

The recalibration sensor and the sensor to be recalibrated can communicate through any suitable means for reporting, such as described, for example, in the different embodiment disclosed herein, to a recalibration circuit. The recalibration circuit may be in the form of programming in a computer at a centralized location, such as the smart nodes 332 or centralized data collection points 333 as shown in FIG. 3, or a circuit or ASIC processor units in a module 112 such as disclosed in the embodiments of FIGS. 1 and 2. The recalibration circuit would have received, either through human input or by any suitable automatic means including the registration of a new or replacement sensor, an indication that the newer sensor, generally, would be the recalibration sensor, assuming that calibration drift of older sensors is a problem being addressed.

Further, once one sensor is recalibrated it can be used to calibrate the next in a network, for instance, to create a domino effect for recalibration of sensors measuring fluid having a relatively uniform measurement characteristic. For instance, an individual pipe with multiple sensors spaced along it can sequentially recalibrate the next sensor at a rate equal to fluid flow through the pipe.

The sensors 111A-111C can be any combination of the above and there may be a multiplicity of individual sensors, some or all of which may comprise a plurality of sensing elements. For instance, a sensor (e.g., sensor 111B in FIG. 1B) can have a plurality of sensing elements 113A-113C to detect multiple parameters within the fluid. Only three sensing elements 113A-113C are illustrated in FIG. 1B, but more than three could be employed. In this way, a sensor 111A can be used to identify chemical signatures or profiles within a fluid (e.g., potable water).

Figure 1E:
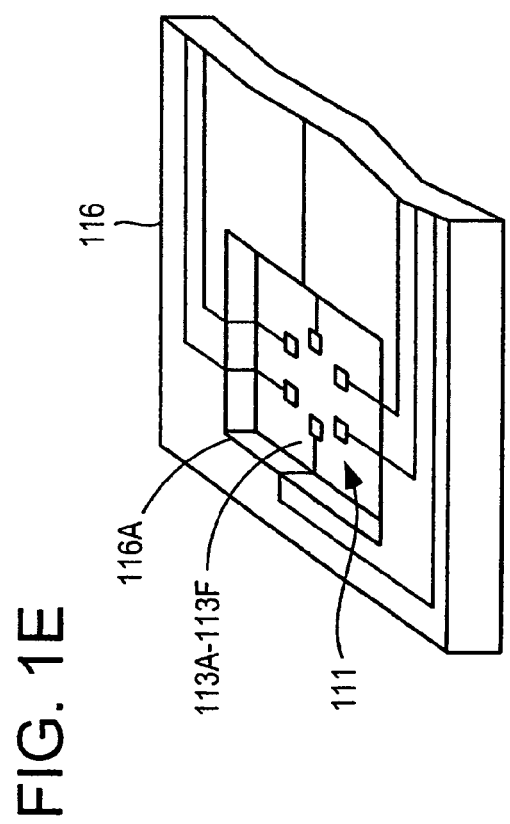
FIG. 1E is an illustration of another exemplary embodiment of a sensor unit.

A sensor 111A, such as shown schematically in the example of FIG. 1E can be made up of individual sensing elements 113A-113F. These sensing elements 113A-113F can be designed to identify different ranges of parameters within a fluid, specific chemicals or substances (e.g., compounds, contaminants) or identify different possible water quality measures, as tailored to the specific expected needs of the water quality monitoring system. Together, such sensing elements 113A-113F can provide a chemical profile of a fluid or can provide data indicative of fingerprints of particular substances (e.g., compounds, contaminants) or classes of substances (e.g., compounds, contaminants). The sensing elements 113A-113F may be mounted on a recessed surface, as shown in FIGS. 1D and 1E or they may be mounted on a non-recessed surface. The sensing elements 113 shown in the recesses 116A of FIG. 1D do not necessarily form a profile on the surface, as shown for emphasis in FIG. 1D, but may instead be co-planar with the surface. Electrical connections are mounted or formed on a substrate 116 in any or many known ways to connect the sensing elements 113A-113F to a processing unit 112A.

Whenever a plurality of sensor components (e.g., 111A-111C, 113A-113F) are incorporated into a sensor unit 110, they may each have a separate processing unit 112A and/or communication unit 112B, or may share common such components via a multiplexer or the like to reduce costs and communication overhead (bandwidth, power consumption, etc.). For instance, ASIC (applications specific integrated circuits) can be utilized to develop sensor units 110 of efficient design. These ASICs can be on a common substrate, or multiple substrates coupled together through electrical connections.

One or more sensors 111 can provide indications of event conditions on a number of bases, including one or more out-of-range events where measured parameters or profiles within a fluid exceed or deviate from a particular range and/or threshold either preprogrammed or downloaded into the sensor unit 110. The sensor units 110 can also provide detection of water profile parameters for comparison against water profile parameters either downloaded into the sensor units 110 or at smart nodes 332 or centralized data collection points 333, as explained in greater details with reference to FIG. 3, below. The detection of chemical fingerprints, signatures or profiles would be coupled to a database of potential chemical profiles for positive identification of even complex contaminants including biological agents and chemical toxins, for example. In this regard, such a database of potential chemical profiles can be stored locally (e.g., on-chip) in a memory interfaced to the processing unit 112A, or can be stored at one or more remote locations for on-line access by the processing unit 112A and communication unit 112B. In either case, the database of potential chemical profiles can be updatable, and in the case of the local memory, the database of potential chemical profiles can be downloaded intermittently into the local memory. Suitable pattern recognition techniques can be used to compare data generated by the sensor unit(s) 110 with the database of potential chemical profiles to generate a potential identification event if there is a potential match with one or more stored chemical profiles.

Physical events, such as a breakage of a pipe might be detected through a pattern of sensor units 110 reporting readings that deviate from historic norms, for example, reduced water pressure compared to historic norms, thereby identifying the exact location or proximate location of the breakage. Also, temperature sensors could be utilized to normalize and scale temperature dependent detection mechanisms but also may be utilized to determine when water distribution systems are at risk of breakage through freezing temperatures.

The sensor unit 110 includes processing and communication units 112A and 112B. The communication capability of the sensor units 110 can include hardwired communication circuits wherein the unit is literally physically connected by wires to other communications devices or communication systems such as telephone lines, satellite or wireless communication devices, etc. The communication unit 112B may also impose information on a carrier for existing power lines within the building or even the power grid of a region. The imposed information signals would then be picked up by local communications devices for long-range communication over telephone lines, private or public networks, cellular communication networks, SMS (short message service) networks, satellites, etc. Additionally or alternatively, the communication unit 112B of an individual sensor unit 110 can include short-range wireless capabilities for communication with local alert and/or long-range communication devices such as telephones, private or public networks, cellular communication networks or satellite devices that may preexist or be installed for communication with a sensor unit 110. Such short-range wireless devices include communication devices utilizing unregulated spectrums using existing protocols such as Bluetooth. Alternatively, wireless LAN protocols such as dictated by IEEE Standard 802.11 (b) or 802.11 (g) could be used, as could long-range wireless devices for transmission to relatively distant stations such as at receivers located at the headquarters of regional water authorities. Other alternatives include communication devices 112B which utilize a preexisting cellular network or wireless networks such as those used by alarm systems. The manner of communication might be dictated by external factors including availability, cost, robustness, efficiency, etc.

A network of sensor units 110 as described herein can be configured to communicate with a central communication device, e.g., a server, and/or sensor unit 110 can communicate with each other as a distributed network, using communication components known in the art. In this way, for example, a first sensor 111A can generate a preliminary identifier if it measures a water quality variable indicative of a detection event (e.g., low chlorine in a potable water system) and can trigger a neighboring second sensor 111B via the distributed network to make a confirmation measurement.

Finally, or in addition to, the communication unit 112B can include on-site alerts such as optical (indicator lights), audible alerts (e.g., alarm sounds), tactile (e.g., vibration of the unit) or can be interfaced to an appropriate control valve for simply shutting off the supply of fluid upon the detection of emergency events, for instance.

Packaging and Location

The sensor units 110 can be packaged and located in a variety of ways. For instance, they can be placed at the shut off valve located at the introduction of water supply into a house, business, industrial site or government site, for instance. Alternatively, they can be placed at each individual faucet or selected faucets where it is likely that the end user 23 might drink water or otherwise consume or cause fluids to be consumed. For instance, water filtration devices adaptable for attachment at the end of a faucet can be adapted to incorporate a sensor unit 110 and include both communication devices that communication with distant locations as well as integrally housed alerts either of an optical, audible or tactile nature. Also, sensor units 110 can be located at any desired points in a municipal water distribution system.

Filter Package Monitors

Figure 1H:
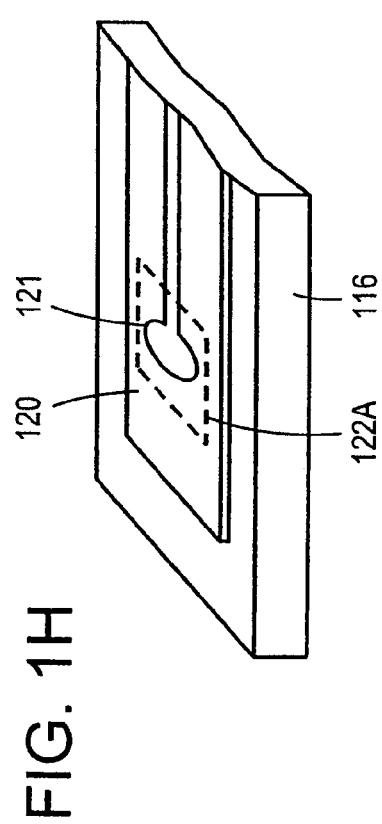
FIG. 1H is an illustration of another exemplary embodiment of a sensor unit.
Figure 1F:
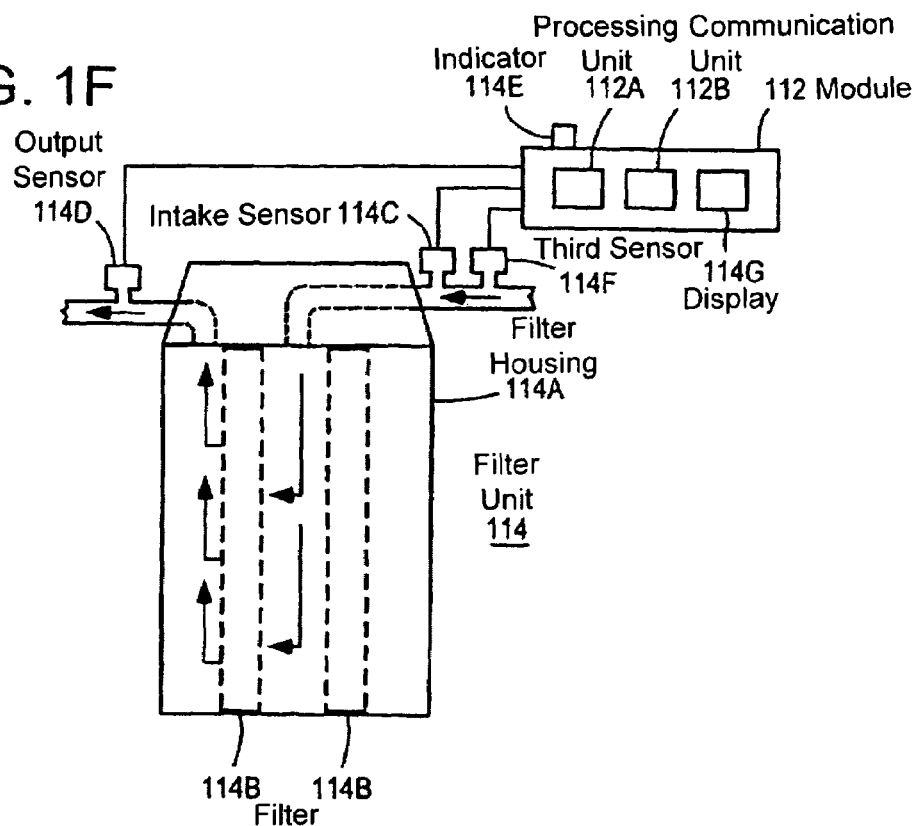
FIG. 1F is an illustration of another exemplary embodiment of a sensor unit.

One exemplary embodiment of the present invention combines a water filter and/or water treatment device with one or more sensor units 110. As illustrated in FIG. 1F, a system for filtering and monitoring a fluid includes a filter unit 114. The filter unit 114 includes a filter housing 114A for holding a filter 114B. A first, intake sensor 114C is configured to be exposed to fluid that enters the filter unit 114 (pre-filtering fluid, or more generally, pre-treating fluid). A second, output sensor (post-filtering fluid) 114D is configured to be exposed to fluid filtered by the filter 114B (post-filtering fluid, or more generally, post-treating fluid). The first, intake sensor 114C can include a plurality of sensors 111A, 111B, 111C, etc., each of which can have one or more sensing elements 113A, 113B, 113C, etc., as can the second, output sensor 114D, such as described above. The individual sensors 111A, 111B, 111C, etc., can act as the monitoring and confirming means for each sensor 114C, 114D, depending on how they are connected and used by a processor 112A, or the intake or output sensing 114C, 114D can act as respective monitoring and confirming means (the roles being interchangeable) for fluid quality measures that are not effected by the filter 114B.

For instance, the first, intake sensor 114C can include an ion-selective sensing element capable of measuring an ion content and a chlorine sensing element capable of measuring a chlorine content. Likewise, the second, output sensor 114D can include an ion-selective sensing element capable of measuring an ion content and a chlorine sensing element capable of measuring a chlorine content. Moreover, each sensor 114C and 114D can comprise additional sensing elements, e.g., electrical conductivity and/or other sensing elements, capable of generating a suite of measurements that can provide particular measurements, which can be combined to generate a fluid-quality profile. For example, the sensors 114C and 114C can comprise at least one of an ion-selective sensing element, an amperometric sensing element, a potentiometric sensing element, a conductivity sensing element, a temperature sensing element, an oxidation-reduction potential sensing element, a chlorine sensing element, an oxygen sensing element, an immunosensor, a DNA probe and an optical sensor.

The filter unit 114 can further include a processing unit 112A coupled to the first and second sensor units 114C, 114D, the processing unit 112A being configured to compare measurement data generated by the first and second sensor units 114C, 114D.

The filter unit 114 can also include a communication unit 112B, either as part of or separate from the processing unit 112A, but coupled to the processing unit 112A. The communication unit 112B can be configured to communicate measurement results (e.g., raw and/or processed data) generated by the processing unit 112A to a remote communication device in the exemplary embodiment of FIG. 1C. It should be noted too that the processing unit 112A can be in the form of a first processing unit and a second processing unit, wherein the first processing unit is arranged with and coupled to the first sensor 114C, and wherein the second processing unit is arranged with and coupled to the second sensor 114D. The first and second processing units can be coupled together to achieve the desired measurement and comparison functions. Also, as with other embodiments described herein, sensor units 110 (whether or not packaged with a filter) can be monitored by a water treatment provider for the purpose of guaranteeing or certifying the quality of filtered and/or otherwise treated water. For example, a private water treatment company or a municipality can provide on-line monitoring of water filtration/treatment equipment at a delivery point (e.g., a home or business), and as part of its service, can guarantee or certify the quality of filtered and/or otherwise treated water. The water filtration/treatment equipment can be provided and/or installed by the monitoring entity or by a different entity. Further, one or more sensors placed at the water intake of a filter/treatment unit can be used to predict how long a treatment element (e.g., filter element) is expected to last based on loading capacity of that element and the amount of contaminants present in the intake water as measured by the sensor(s), and this information can be communicated on-line to the water treatment provider by any suitable method as disclosed herein.

As for packaging, the first and second sensor 114C and 114D can be attached to the filter housing 114A, but the filter 114B that filters the fluid can be replaceable without necessarily replacing the first and second sensors 114C, 114D depending on the particular embodiment. The sensors 114C, 114D can be designed to last the life of the filter unit 114, or be separately replaceable or replaceable with the filter 114B. In the latter case, it might be expedient to have the first and second sensor units 114C, 114D attached to or embedded in the filter 114B, such as shown in the exemplary filter unit 114' illustrated in FIG. 1G. In this regard, an appropriate interface, such as a waterproof plug, can be provided to couple the sensors 114C, 114D to the processing unit 112A.

In this way, the processing unit 112A is configured to generate an identifier to indicate a replacement condition for a filter 114B to be placed in the filter housing 114A based upon the comparison of the measurement data from the first and second sensor units 114C and 114D. An indicator 114E (e.g., a simple light, with or without a label, or an audible indicator) that indicates the replacement condition for the filter might be included as attached to or part of the filter housing 114A for instance, and/or the communication unit 112B might communicate the replacement condition to a remote communication device. Optionally, a display 114G can be provided for displaying information such as water quality measurements, date of last filter change, and/or remaining filter life (based on known loading specifications of the filter 114B and measurement data obtained by the sensors 114C and 114D).

In still other variations, a third sensor unit 114F configured to be exposed to the fluid that enters the filter housing 114A can be employed, wherein the third sensor 114F is coupled to the processing unit 112A. The processing unit 112A would be in this embodiment configured to operate in conjunction with the first sensor 114C to monitor the fluid, generate a variable based on said monitoring, generate a preliminary identifier if the variable is indicative of a detection condition, and operate in conjunction with the third sensor 114F to determine whether the detection condition has occurred based on new data. As explained above, this monitor and confirm function can be carried out with sensors 111 configured within the same sensor unit 110, but the raw data can be communicated to a central location for this processing, and the central location can then be instructed whether to carry out the confirmation function.

As with other embodiments, this embodiment can include a communication unit 112B configured to report the detection condition to a remote communication device if the processing unit 112A confirms that the detection condition has occurred, and/or provide raw data and/or processed data to a remote communication device. Additionally or alternatively, the processing unit 112 might be configured to generate a sensor alert identifier if the third sensor unit 114F provides a measurement reading that differs by a predetermined amount from a contemporaneous measurement reading of a same type provided by the first sensor unit 114C. This configuration might serve as an indication that the first sensor unit 114C may be faulty. The first sensor unit 114C could then be deactivated by the processing unit 112A.

As with other embodiments disclosed herein the first and second sensor units 114C and 114D can include an ion-selective sensing element capable of measuring an ion content, a chlorine sensing element capable of measuring a chlorine content and a conductivity sensing element capable of measuring electrical conductivity, for example. More generally, the sensors 114C and 114C can comprise at least one of an ion-selective sensing element, an amperometric sensing element, a potentiometric sensing element, a conductivity sensing element, a temperature sensing element, an oxidation-reduction potential sensing element, a chlorine sensing element, an oxygen sensing element, an immunosensor, a DNA probe and an optical sensor.

Figure 1G:
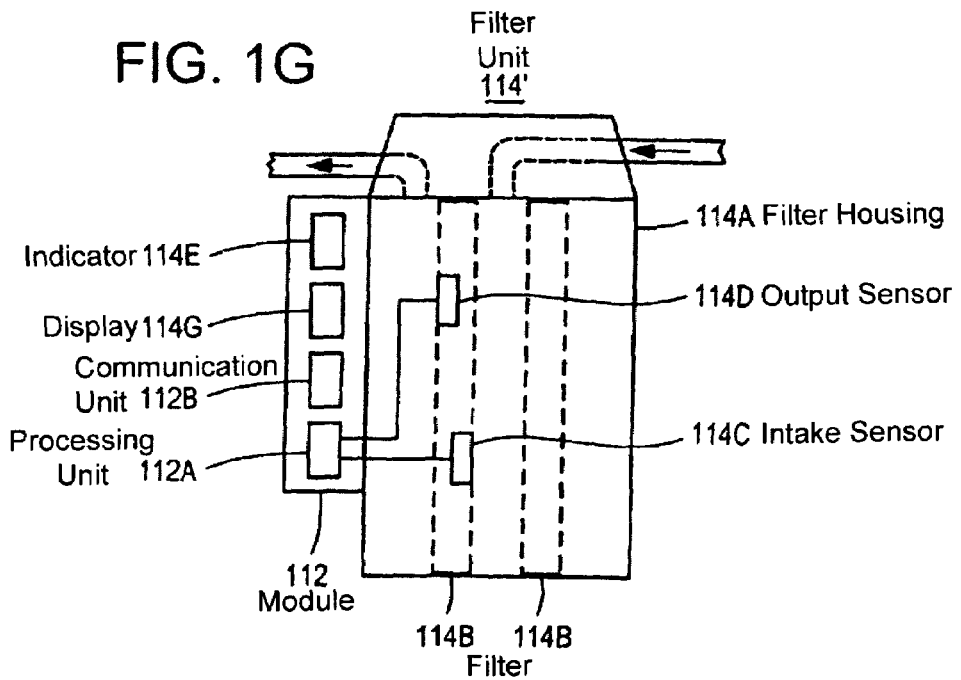
FIG. 1G is an illustration of another exemplary embodiment of a sensor unit.

As also with other embodiments of the present invention, the module 112 can be attached to the filter housing 114A as shown in FIG. 1G, or can be configured as a stand-alone unit coupled to the sensors 114C, 114D via electrical (wired or wireless) connections, wherein the module 112 could be mounted on a wall or plugged into a power outlet. Of course, the processing unit 112A can be in the form of a first processing unit connected to the first sensor unit 114C, and a second processing unit connected to a second sensor unit 114D. The first and second processing units can thereby be configured to compare measurement data generated by the first and second sensor units 114C and 114D.

The processing unit 112A, however physically configured, could be configured to communicate with a communication unit 112B and to instruct the communication unit 112B to report the detection condition to another communication unit if the processing unit 112 confirms that the detection condition has occurred and/or raw data, in this exemplary embodiment.

Although the examples described above have referred to a filter unit 114, the filter unit 114 could be any suitable fluid-treatment device such as, for example, a water-softening device, a distillation device, or a reverse-osmosis or membrane filtration device, media filtration device, or any combination thereof, including or filter housing and/or a filter.

Multiple Sensors with Selective Exposure

Figure 1K:
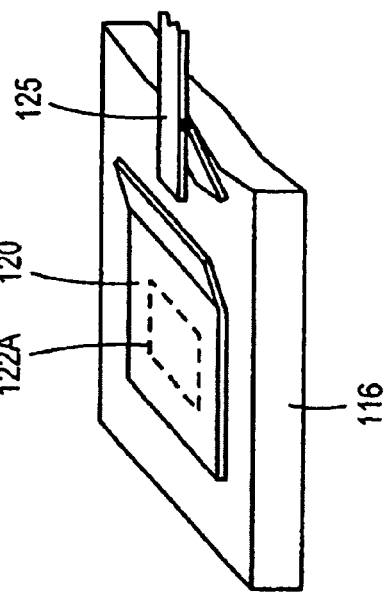
FIG. 1K is an illustration of another exemplary embodiment of a sensor unit.
Figure 1I:
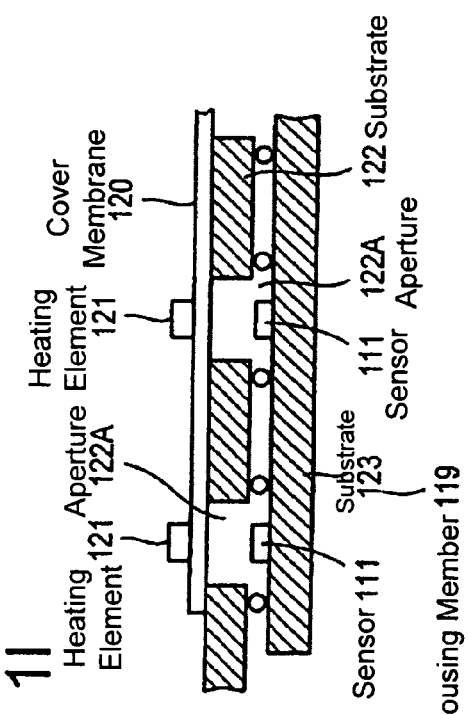
FIG. 1I is an illustration of another exemplary embodiment of a sensor unit.

With reference to FIG. 1D, a multi-sensor apparatus for monitoring a fluid can include a substrate 116 and a plurality of sensors, each of which can include one or more than one sensing element attached to or formed in or on the substrate 116. In FIGS. 1D, 1E and 1I individual sensors are identified by reference numeral 111, and individual sensing elements are identified by reference numeral 113, for brevity. Each sensor 111 is configured to be exposed to a fluid. Also, a mechanism (discussed below) for selectively exposing individual sensors of the plurality of sensors 111 to the fluid is provided in this embodiment. As with other embodiments at least one of the sensors 111 can include a plurality of sensing elements 113 and at least one of the sensors 111 can included both an ion-selective sensing element capable of measuring an ion content and a chlorine sensing element capable of measuring a chlorine content, for instance. More generally, at least one of the sensors 111 can comprise at least one of an ion-selective sensing element, an amperometric sensing element, a potentiometric sensing element, a conductivity sensing element, a temperature sensing element, an oxidation-reduction potential sensing element, a chlorine sensing element, an oxygen sensing element, an immunosensor, a DNA probe and an optical sensor.

As illustrated in FIGS. 1D-1E, the sensors 111 can be formed in recesses 116A. Any mechanism for forming the recesses 116A can be employed, including lithographic patterning and etching processes to produce recesses on the surface the substrate 116. The substrate 16 alternatively can be formed as a first substrate 122 comprising a plurality of apertures 122A extending therethrough, and wherein each sensor 111 is disposed on a surface of a second substrate 123, as shown in FIG. 1I. The second substrate 123 is bonded to the first substrate 122 such that each sensor 111 faces a respective aperture 122A, of the first substrate 122, using for example a flip-chip process. Forming the sensors 111 in recesses 116A can be advantageous in embodiments involving mechanisms for selective exposure of multiple sensors 111 as this can protect the surfaces of the sensors 111; however, it is not necessary to form the sensors in recesses in selective exposure embodiments.

As noted above, a mechanism for selectively exposing individual sensors 111 to the fluid can be provided. For example, as illustrated in FIGS. 1D, 1H and 1I, a cover membrane 120 (or multiple cover membranes, one for each sensor 111) can be attached to a surface of a substrate 116, 122, the cover membrane 120 covering the plurality of sensors 111, in the recesses 116A, or below the apertures 122A. A plurality of heating elements 121, for example, can be attached to the membrane 120 at positions proximate to respective sensors 111. Each heating element 121 can be selectively operable to generate an opening in the membrane 120 thereby allowing a particular sensor 111 positioned proximate to a recess 116A or aperture 122A to be exposed to the fluid. As an alternative to using heating elements 121 to selectively expose a sensor 111, any suitable mechanisms which serve to dissolve the membrane or physically remove or tear of at least a portion of the membrane 120 can be used, such as shown in FIG. 1J by a conceptually illustrated mechanical perforator 124 or FIG. 1K by a conceptually illustrated mechanical gripper or scraper 125. The embodiments of FIGS. 1J and 1K illustrate in a generic way any number of mechanical means for selectively removing the membrane 120. In addition, any suitable actuation mechanism(s) can be used enable the mechanical perforator 124 or the mechanical gripper or scraper 125 to be positioned adjacent to a given sensor 111 and to selectively expose that sensor 111. For example, the sensors can be configured along a line or in a two-dimensional array on the substrate 116, and one or more actuators can be used to provide relative linear motion in one or two directions between the substrate 116 and the mechanical member 125, 125. As another example, the sensors 111 can be arranged along the circumference of a circle, and one or more actuators can be used to provide relative rotational motion between the substrate 116 and the mechanical member 124, 125.

As with other embodiments disclosed herein, the substrate 116 can be a silicon substrate or can be another type of substrate such as, for example, ceramic, glass, $SiO_2$, or plastic. An exemplary multi-sensor apparatus can also be fabricated using combinations of such substrates situated proximate to one another. For example, a silicon substrate having some sensor components (e.g., sensing elements) can be mounted on a ceramic, $SiO_2$, glass, plastic or other type of substrate having other sensor components (e.g., other sensing elements and/or one or more reference electrodes). Conventional electronics processing techniques can be used to fabricate and interconnect such composite devices. Each sensor 111 can have one or more corresponding reference electrodes, the reference electrodes being located either on the same substrate as one or more sensors 111 or on or more different substrates. For example, reference electrodes can be fabricated on one or more ceramic, $SiO_2$, glass, or plastic substrates (or other type of substrate), wherein a sealed fluid reservoir is provided in the substrate for a given reference electrode. Alternatively, multiple sensors 111 can share one or more common reference electrodes, the common reference electrode(s) being located on the same substrate as a sensor 111 or on one or more different substrates. Providing separate reference electrodes for each sensor 111 can be beneficial since the performance of reference electrodes can degrade with use. By providing selective exposure of reference electrodes associated with individual sensors 111, sensor performance can be enhanced because fresh reference electrodes can be provided when a new sensor is activated. A reference electrode can be exposed using the same exposure system as a sensor 111 or using a different exposure system.

The membrane 120 can be made of any suitable material such as a polymer material (e.g., polyester or polyimide) for instance and the membrane 120 may be attached to the substrate 116, 122 via an adhesive or may be attached to the substrate 116, 122 by a heated lamination process. The sensors 111 may be lithographically produced (e.g., using known microelectronics processing techniques), dispensed or screen printed, for example, on a recessed or non-recessed surface of the substrate 116.

A multi-sensor apparatus can enable carrying out a confirmation function as discussed above by allowing the processing unit 112A to selectively expose a desired sensor in response to a measurement by another sensor indicative of a detection condition. The processing unit 112A can trigger a power circuit to direct power to a heater 121 to expose the desired sensor 111.

Figure 1L:
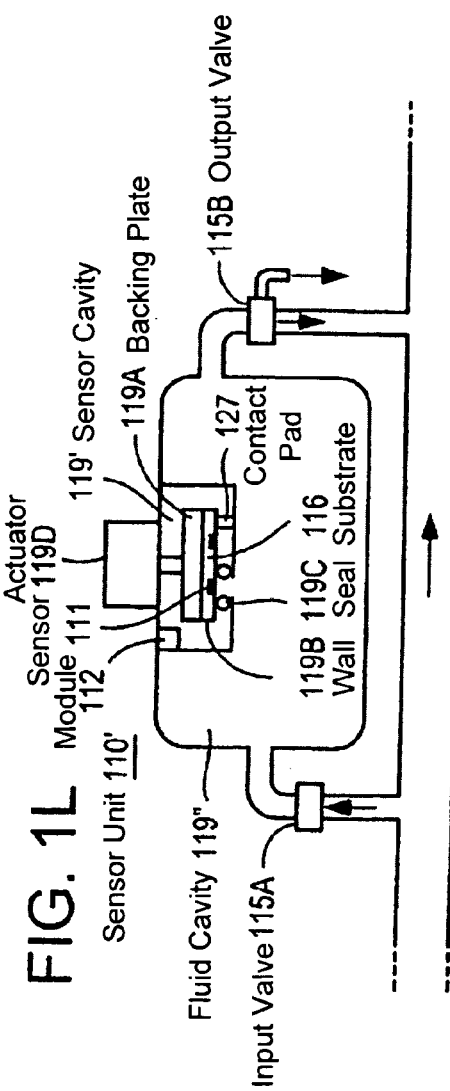
FIG. 1L is an illustration of another exemplary embodiment of a sensor unit.

Another exemplary embodiment for selectively exposing sensors 111 is illustrated in FIG. 1L. As shown in FIG. 1L, a sensor unit 110' is connected to a fluid source via an input valve 115A and an output valve 115B. The sensor unit 110' comprises a housing member 119 with a wall 119B to provide a sensor cavity 119' and a fluid cavity 119". A substrate 116 is provided on a backing plate 119A in the sensor cavity 119' adjacent to an aperture in the wall 119B to allow a sensor 111 to be exposed to a fluid. A seal 119C, such as an o-ring, arranged adjacent to the aperture and positioned between a surface of the substrate 116 and a surface of the wall 119B of the housing member 119, to seal the substrate 116 against the housing wall 119B. An actuator 119D moves the backing plate 119A and the substrate 116 to selectively locate an individual sensor 111 to a region of the aperture such that the particular sensor 111 is exposed to the fluid. The substrate 116 is preferably flat to allow for a good seal, but the invention is not so limited. As discussed previously, sensors 111 can be formed on a recessed or non-recessed surface of the substrate 116. To minimize the potential for fluid leakage into the sensor cavity 119', the valves 115A and 115B can be actuated to partially or substantially drain the fluid cavity 119" before selectively exposing a new sensor 111 with the actuator 19D.

Figure 1M:
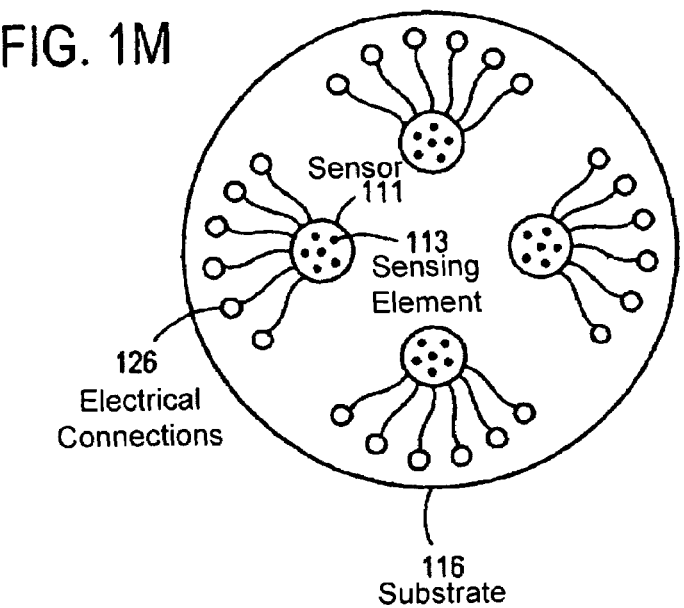
FIG. 1M is an illustration of another exemplary embodiment of a sensor unit.
Figure 1N:
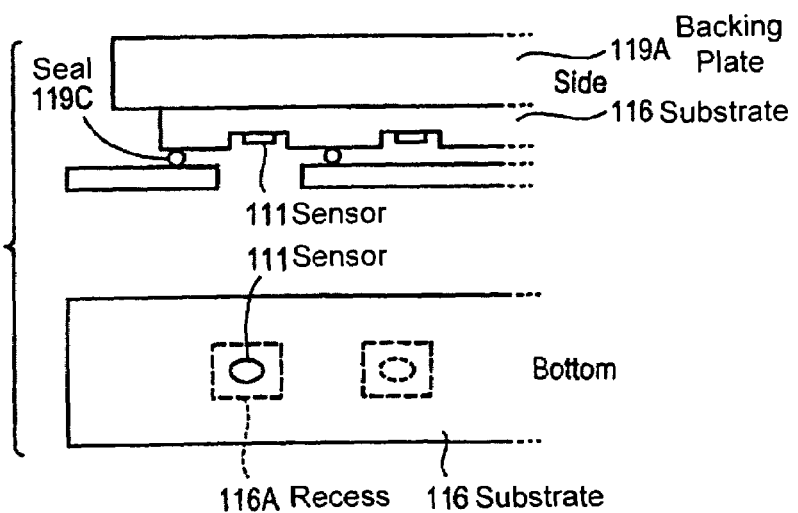
FIG. 1N is an illustration of another exemplary embodiment of a sensor unit.

The sensors 111 can be lithographically produced, deposited or screen printed on a recessed or non-recessed surface of the substrate 116, and might be formed at the circumference of a circle so as to allow the actuator 119D to be a simple carousel mechanism using rotational motion as shown in FIG. 1M, or can be formed in a staggered or straight line as shown in FIG. 1N, or in a two-dimensional array, for instance, and the actuator 119D can provide for a linear motion in one or more dimensions. The substrate can be in the form of substrate 116 with recesses 116A as shown in FIGS. 1N and 1E, or can be in the form of the flip-chip bonded substrate 122, 123 shown in FIG. 1F.

In view of the above, it will be apparent that carousel or linear motion embodiments can be used in conjunction with sensors 111 covered by at least one membrane 120 attached to a surface of the substrate 116 (e.g., FIGS. 1J and 1K), in which case a mechanical member 124, 125 selectively displaces or perforates the at least one membrane 120 in a region proximate to an individual sensor 111 to allow the particular sensor 111 to be exposed to a fluid. In this regard, a configuration similar to that illustrated in FIGS. 1L and 1M (or 1N) can be used. The actuator 119D can provide relative motion between the substrate 116 (mounted on backing plate 119A) and the mechanical member 124, 125 to allow the mechanical member 124, 125 to selectively displace the at least one membrane 120. The seal 119C and housing 119 may not be necessary in embodiments involving a membrane 120.

In the embodiments in which motion of the sensors 111 is designed to occur, electrical connections 126 could be configured to align with a contact pad 127 or pads to assure electrical connection between the sensors components 111, 113 and the processor 112A.

Distribution of Sensor Elements

Figure 2:
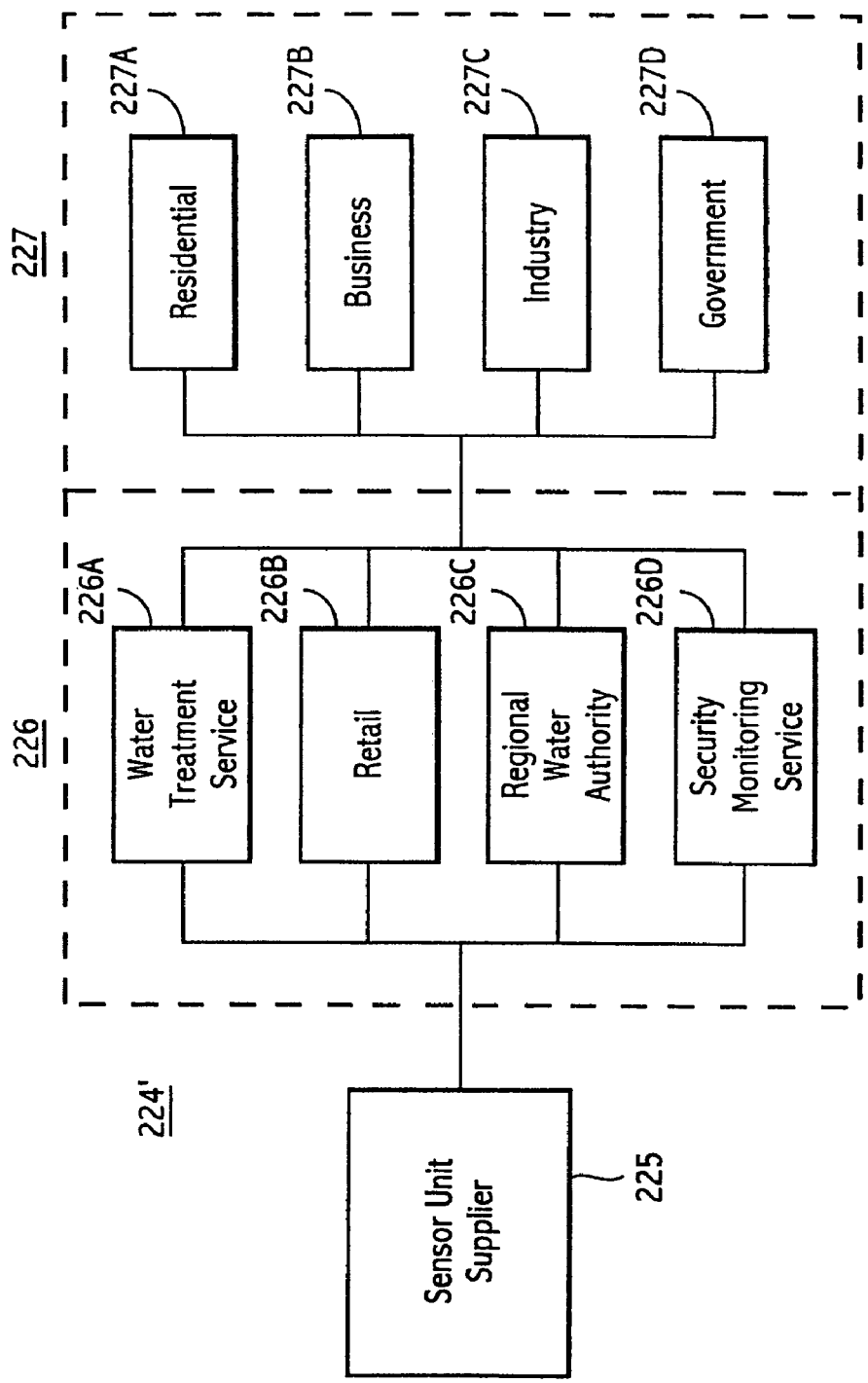
FIG. 2 is a block diagram of an exemplary sensor unit supply chain in accordance with aspects of the present disclosure.

Unlike some prior systems which required the regional water authority to install water quality measuring devices at various points within the water treatment plants and/or within a water distribution network, the present inventors have devised a mechanism wherein the distribution of sensor units can utilize pre-existing commercial distribution systems 224, such as illustrated in the exemplary embodiment shown in FIG. 2. For instance, a sensor unit supplier 225 (e.g., an original equipment manufacturer, reseller or wholesaler) can supply or arrange to have supplied sensor units 110 to pre-existing product distributors 226, which might include among others water treatment services 226A, such as Culligan Water Treatment Services, Ecco Water Systems, Millipore Corporation, and GE Specialty Materials, for example. These water treatment services 226A provide equipment and/or consumable supplies for treating water such as softening agents, filtration devices, filters, etc. to residential locations (e.g., houses, apartments, mobile homes, etc.) 227A, businesses 227B, industrial plants 227C and/or government facilities 227D. The water treatment services 226A provide sales, distribution and installation of the sensor units 110 through preexisting commercial distribution systems 224, thereby minimizing the cost of establishing supply chains of sensor units 110 to end users 227 at residential locations 227A, businesses 227B, industrial plants 227C and government facilities 227D, for example, or any location that would want or use the services of a water treatment service 226A, for example. Alternatively or additionally, the government regional water authority can be utilized as an installer of sensor units at the water authority's existing sensor locations and/or additional locations, and/or can also be utilized as a distributor of sensor units to homes, businesses, industrial plants, and government facilities, wherein monitoring of the sensor units can be carried out by another entity other than the regional water authority.

For instance, water treatment services 226A can receive sensor units 110 from a sensor unit supplier 225 for installation at the sites of the end users 227. The water treatment service 226A can sell the sensor units 110 as an added value to their overall water treatment service, as explained in more detail with reference to FIG. 3, below. Water treatment services 226A thereby act as sales and distribution networks for the installation of sensor units 110 at the end users 227. Additionally, because water treatment services 226A often install the equipment they are selling, leasing or otherwise conveying to the end user 227, this installation can include installation of the sensor units 110, and can further include establishing communication between the sensor units 110 and centralized data collection points such as the water treatment service 226A, smart nodes 332 and/or a single centralized data collection point 333 within a water monitoring network of a geographic or political region or regions, as explained with reference to FIG. 3, below. The water treatment service 226A can thus carry out on-line monitoring of intake water and treated (e.g., filtered) water and, as mentioned previously, can also utilize such monitoring to guarantee or certify the quality of treated water at end-user delivery points 227A-227D.

Alternatively, the sensor unit supplier 225 can supply sensor units 110 or cause them to be supplied directly to the retail outlets 226B (e.g., retail outlets in physical buildings or retail outlets provided through Internet websites, or both) or through wholesale outlets to retail outlets 226B. The end users 227 would then obtain sensor units 110 directly from retail outlets 226B for self-installation or end-user assisted installation. Hence, the retail outlet 226B provides the sales and distribution mechanism, whereas the end user 227 provides installation of the sensor units 110 at points of end use of the water in the water distribution system. The end user 227 would then establish or facilitate establishment of communication with a monitoring network 330. In some instances, the sensor unit 110 can include a cellular communication device with its own unique identification code. The end user 227 can simply turn on the cellular communication device and either enter the end user's location or address, or allow the cellular communication device to be located through triangulation if that capability exists within a particular cellular system. Of course, this mechanism could be employed regardless of how the sensor unit 110 was distributed.

Another form of preexisting commercial distribution system 224 includes regional water authorities 226C which, in the regular course of their activities, installs water meters and the like at the locations of end users 227, whether residential 227A, businesses 227B, industrial plants 227C or government facilities 227D. The sensor units 110 would simply be installed by the regional or multi-regional water authority 226C or its contractors. In this circumstance, there may not be an actual sale or other conveyance of the sensor unit 110 to the end user, who may not even be aware of the installation. Meter manufacturers can incorporate sensor unit capabilities into standard meters for selective activation by the regional water authority 226C, by the meter manufactures or another entity interested in providing data from end-point locations within a water distribution system. Here it can be seen that the invention can be used in conjunction with other fluids, such as natural gas, if there is a need or a need develops.

Additionally or alternatively, home security, home (e.g., utility) monitoring, and health monitoring services 226D can provide sales, distribution and installation of sensor units 110 as part of or as value added to the offered monitoring services. For instance, home security and health monitoring services 226D, as well as generalized home monitoring services which may include monitoring the usage of utilities, can add water quality monitoring capabilities as part of their services. The sales, distribution and installation of sensor units 110 would then use the same network these services have established to sell, distribute and install other equipment to perform other home and health monitoring functions.

As should be appreciated by the above, the sensor unit distribution system 224 for distributing sensor elements 110 utilizes one or more pre-existing commercial distribution systems 226 to sell, distribute and install sensor units 110 at the location of the end user 227. Virtually any product distribution system reaching residences 227A, businesses 227B, industrial plants 227C and/or government facilities 227D (or any locations where water is used by end users in a water distribution system) can be used to also distribute sensor units 110, perhaps as added value services or products. The thus distributed sensor units 110 can form a water monitoring network 330 specific to the particular pre-existing product distribution system 226, or sensor units 110 distributed by a variety of pre-existing product distribution systems 226 form a larger water monitoring network 330, or a mixture wherein certain data gathered by sensor units 110 distributed by a particular pre-existing product distribution system 226 would be proprietary to the particular pre-existing product or service distributor 226 (e.g., data related to water treatment equipment performance), but other data (e.g., data related to water quality within a water distribution system) would be provided to a water quality monitoring network 330. In this way, a larger and perhaps more distributed panel of sensor units 110 can be distributed and installed at relatively little cost to the water authorities, for instance.

With reference to FIG. 3, various aspects of the present disclosure including data collection, centralized or distributed data analysis and data distribution will be explained by way of an exemplary water monitoring system 330. In the exemplary water monitoring system 330, various sensor units 110A-110F at sites A-F are connected to the water quality monitoring system 330 by communication links as identified above with reference to the details of the sensor units 110. While six sensor units 110A-110F are shown in FIG. 3, many more are contemplated and the drawings should not be relied upon for judging orders of magnitude or the number of sensor units 110, smart nodes 332 or centralized data collection points 333.

The sensor units 1110A-110C, for instance, are connected to a smart node 332A (a node that has data processing power), whereas other sensor units 110D-110F may be connected to a separate smart node 332B or the same smart node 332A as warranted by various factors involving the network and water authorities, including the bandwidth of communication devices, the appropriateness of distributing processing an analysis of data, etc. The smart nodes 332 can have a relationship to the region or authority of regional water authorities 226C, for example.

The sensor units 110 may provide raw data, or just confirmed detection events to smart nodes 332 and/or directly to a centralized data collection point 333. The double-sided arrow lines in FIG. 3 indicate the flow of data up the hierarchical network 330, and data and inquiries down the hierarchical network 330, there being contemplated two-way communication in some embodiments. In certain embodiments, only communication going up the hierarchical chain is necessary.

The smart nodes 332 may process the raw data to monitor, identify and confirm detectable events in the water quality. Alternatively, the sensor units 110 can provide monitoring, identifying, confirming and reporting functions to the smart nodes 332 or centralized data collection points 333. Whether the smart nodes 332 process raw data or rely upon the sensor units 110 for confirmed data, the smart nodes 332 having received data from a variety of sensor units 110A-110F at a variety of sites 110A-110F can aggregate and further process such data to determine historical water quality measures, overall quality measures, trends and multipoint measures of a regional water distribution pipe system. The introduction point or source of possible contaminants, water main breaks, freezing pipes, etc., can be traced by analysis of the multipoint data gathered at smart nodes 332 or centralized data collection points 333 by mapping techniques based on the locations of the sensor units 110 within a water distribution system and the measure and/or reported events from the distributed sensor units 110.

The data collection can run in real time, and can continuously, or intermittently (e.g., periodically at pre-set time intervals) monitor fluid quality, or upon inquiry, or operate based on stored data at the sensor sites 110A-110F, depending on the data storage and communication capabilities of the sensor units 110. Real-time data has obvious advantages and it should be noted that most types of sensor units 110 contemplated above measure in real time (whether continuously, periodically or upon inquiry), rather that taking samples and testing the samples at a later time.

Additionally, the smart nodes 332 may periodically or at the command of an operator inquire as to measured data from the sensor units 110 as communication protocols or information needs might dictate. The centralized data collection as represented by the smart nodes 332 and the centralized data collection point 333 can be conducted over private or public networks (e.g., VPN, WAN, the World Wide Web including the Internet), dedicated telephone lines, cellular networks, or virtually any other form of communication. For instance, telephone land-lines and telephone wireless networks can be utilized for a call-up by the sensor units 110 for periodic interrogation by the smart nodes 332 or centralized data collection point 333 of the sensor units 110. Additionally, other communication protocols can be used including communications over a pre-existing power grid by a super-imposed carrier over a power line using known or future protocols and techniques. Further, acoustic waves carried by water in the water distribution system can be utilized for information transmissions. Other communication mechanisms can be utilized independently or in combination, including fiber optics, satellite communications and virtually any communication protocol or mechanism capable of transmitting raw and/or analyzed data between the sensor units 110 and the smart nodes 332 and/or centralized data collection points 333.

Additionally and/or alternatively, the sensor units 110D-110F can communicate to smart nodes 332 and/or centralized data collection points 333 through other entities such as water treatment services 226A, home monitoring (security and utility) services and/or health monitoring services 226D, retail outlets 226B, and/or regional water authorities 226C, which would then convey data to smart nodes 332B, as illustrated in the exemplary embodiment shown in FIG. 3.

With respect to data distribution, once the data has been gathered and analyzed, raw data, analyzed data and aggregated data can be distributed, whether from smart nodes 332 that may be regional and/or that may be specific to regional water authorities, or to centralized data collection points 333 that may be multi-regional in nature. The types of data can be categorized as data containing user identifiable information and aggregated data, which may or may not contain user identifiable information.

Data containing user identifiable information is useful for end users 227 for a variety of reasons. For instance, for sensor units 110 that include a sensor 111 or sensor element(s) 113 or sensor groups positioned after a water treatment device such as a water softener or filter 114, data relating to a parameter indicating a water quality detection event can be utilized by the end user 227 to inform him or her that filters and/or water treatment chemicals need to be replaced or replenished as the situation dictates. This can be done at the sensor unit 110 by indicators or the like, or through communications from smart nodes 332 or centralized data collection points 333. The end user 227 may also be interested in the performance of the local regional water authority 333C to serve as a check upon the performance of the regional water authority 226C insofar as the end user 227 may question the regional water authority 226C when the water quality has been reduced or changed.

Raw and analyzed data from the smart nodes 332 can be provided to regional water authorities 226C for determining compliance with water quality standards and as internal checks on the performance of the regional water authority 226C. Additionally, raw and analyzed data from smart nodes 332 and/or centralized data collection points 333 can be supplied to multi-regional water authorities 335 such as national water authorities to determine compliance with appropriate water quality standards by regional water authorities 226C and as determinations of the overall health of the multi-regional water supply to detect the presence, persistence and extent of contaminants in the multi-regional water supply so as to determine or trace the origin and extent of problems within the water supply. Additionally, the information can be supplied back to preexisting commercial distribution systems 224.

For instance, water treatment services 226A might be interested in determining the water quality of water leaving water treatment devices installed at the location of end users 227 and may be interested in the water quality of the water entering the water treatment devices, so as to alert end users 227 of the need for replenishing chemical supplies and/or replacing filters, or automatically providing the end user 227 with such supplies, or to alert the end user 227 of problems with the water supply, particularly those not correctable by the water treatment devices, as the terms of any agreement between the water treatment service 226A and the end user 227 may dictate. Such alerts can be provided in a variety of ways, such as, using local indicator (e.g., a light, audible alarm, or other form of alert on the sensor unit housing), displaying information on a display (e.g., a display located on the sensor unit housing), making a telephone call to the end user, or sending an electronic message (e.g., e-mail, pager message, SMS, etc.) to the end user, or any combination of these approaches. Moreover, if potentially dangerous water quality conditions are detected, an alert can also be sent to the regional water authority. For example, if an identification event (e.g., relating to a potentially dangerous condition) is detected through comparison of sensor data with a database of potential chemical profiles, a corresponding alert can be sent to both the end user and the regional water authority. Also, depending upon the condition identified, a suitable control valve(s) can be operated to shut off the water supply to the end user as discussed previously.

Further, where water treatment devices (e.g., filters) are distributed to be associated with sensor units, water treatment services can guarantee or certify the quality of water treated by the water treatment devices as an additional service to end users. Moreover, customers can be billed per unit of water treated by the water treatment devices, either in place or, or in addition to, being billed for the water treatment devices and/or consumables themselves.

With respect to retail outlets 226B, the retail outlet 226B can use the data to prompt end users 227 to purchase additional filters and/or chemicals and/or replace filtration and treatment devices based on a measure of the water quality either entering and/or exiting such devices.

The raw and analyzed data can also be provided to home monitoring and health monitoring services 226D for the benefit of informing the end users 227 as to the quality of the water entering the domain of the end user 227.

In addition to the foregoing entities 226A-226D, 335 that might be interested in the quality of water at the location of the end user 227, other entities may be interested in the quality of water reaching end users 110. For instance, water quality watch groups may be interested in aggregated data to determine trends in the water quality to rate and impose pressure on regional and multi-regional water authorities 226C, 335. Government entities may be interested in determining the viability of the water distribution infrastructure both on a regional and multi-regional scale. Academics may be interested in the data to determine global trends in water quality. Real estate sales facilitators may be interested in identifying water quality as one factor among many factors that might be used in a home owner's decision to buy or sell an individual house within a particular region. Government agencies such as the U.S. Center for Disease Control, Environmental Protection Agency, Department of Homeland Security, and hospitals may be interested in the data to alert the public and/or determine the origin and spread of disease, toxins or other issues of health having origins in the water supply that might concern a community or a nation. Aggregated data can be used to determine trends, and/or user identifiable data may be used to pinpoint particular sources of problems in regional water distribution networks or multi-regional water distribution networks. The underlying theme is that the water monitoring system provides a mechanism wherein various types of information concerning water quality can be shared and/or sold to a variety of interested parties on exclusive or non-exclusive bases by a party that can be relatively neutral and independent.

Consideration for End Users and for Access to Data

Insofar as end users 227 are asked to install or permit the installation of sensor units 110 capable of communicating data outside the domain of the end users 227, some consideration to the end user 227 would seem appropriate in some circumstances. For instance, the end user 227 may view as consideration the ability of the sensor unit 110 and/or water quality monitoring system 330 of which his or her sensor unit 110 is part to alert him of potential hazards that may not otherwise be available. For instance, to obtain the function of having a local indicator provide information about water quality, the end user 227 might have to agree to share information with a water quality monitoring system 330. Alternatively or additionally, the end user 227 might agree to obtain the benefit of analysis that are not detectable via the processing power of a individual sensor unit 110 at a price point the end user 227 is willing to pay. Hence, the consideration for the communication of data to a water quality monitoring system 330 would be the value added to sensor units 110 a price point that the end user 227 is willing to pay.

Additionally, the end user 227 would likely be aware or be made aware that the communicated information is to the benefit of the overall community. It would appear that the end user 227 would have a small threshold in the way of privacy concerns insofar as the volume of water use is already monitored at the end user location and the end user 227 imparts no private or personal information upon the quality of the water and therefore the information developed by the sensor units 110.

Additionally or alternatively, the sale or other conveyance of the sensor unit 110 can be conditioned upon the agreement by the end user 227 for the transmission of data to smart nodes 332 or centralized data collection points 333. Further, sale of the equipment, subscription of monitoring or water treatment services 226A and other subscription based services can provide consideration to the end user 110 as well as lend/lease, can be condition upon providing the communication link and the data provided by the sensor units 110.

Additionally, water authorities 226C can require the installation of sensor units 110 as part of services such as the supply of water or other services generally provided by local governments. Finally, the sensor units 110 may be required to be installed by the end user 227 or be permitted by the end user 227 to be installed by regulation of government.

As consideration for access to both raw and analyzed data, those wishing to access the data can do so by subscription base payments either of a periodic nature (e.g., monthly and/or yearly payments), fully paid-up licenses, fees or per individual reports or a combination thereof. Additionally, fees could be based upon the report of any particular detected event or based on the number of detected events per report. Aggregated data reports can add value by providing historical data, comparison data or other added value imparted by the intelligence and data bases of the reporter service or entity, such that the raw data, the individually end user identifiable data, and the aggregated data can be analyzed by informed individuals and/or through algorithms to provide enhanced value to the quality of the data being reported. Compensation can take the form of payments by entities capable of assisting the end user 227 as part of consideration for any such referral or identification of prospective end users 110 in need of assistance.

Measurements with Portable Sensor Units

Figure 4:
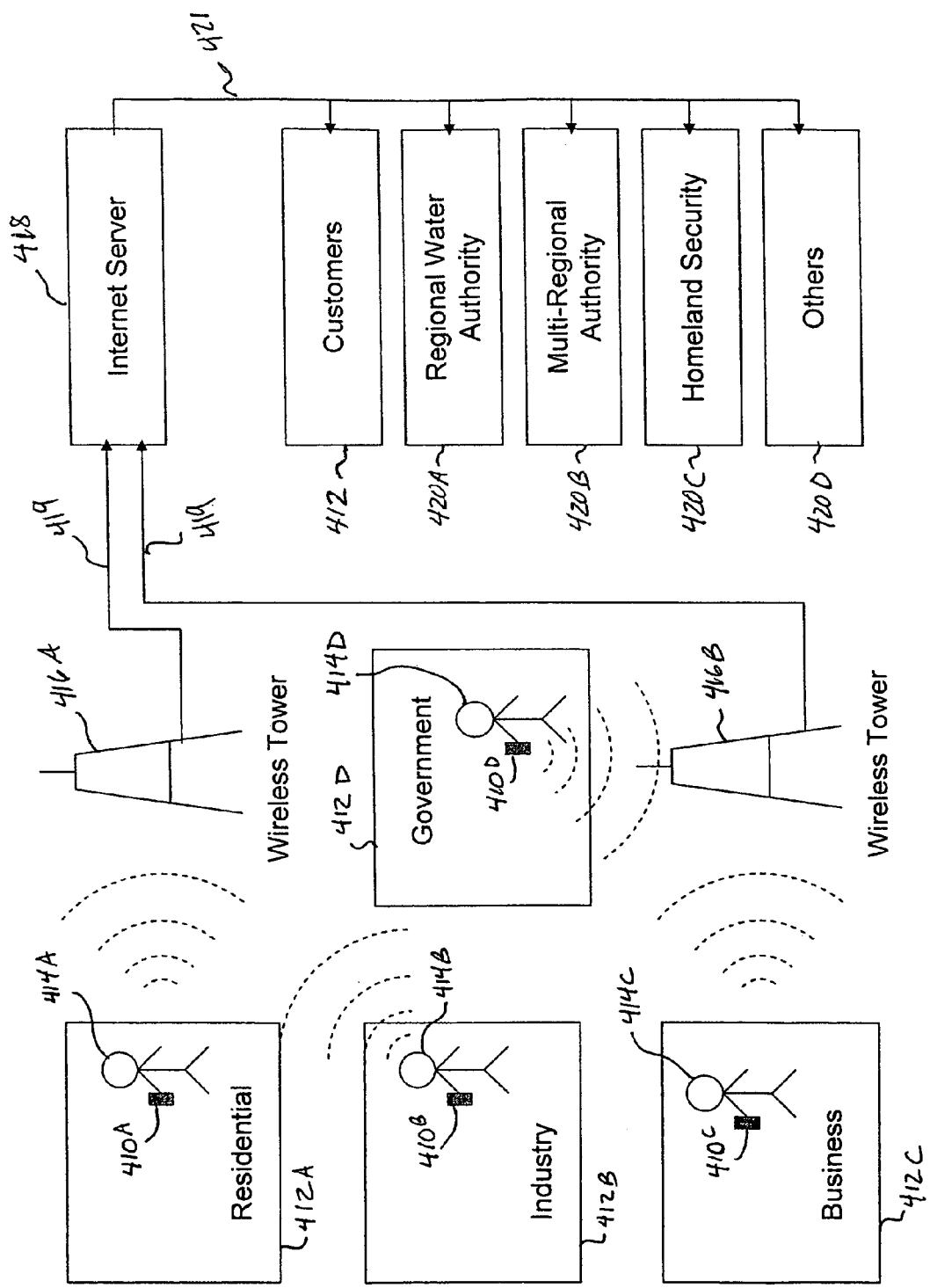
FIGS. 4-11G illustrate further exemplary embodiments.

According to another aspect of the invention, a method and system for monitoring fluid quality using portable sensor units having wireless communication capability is provided. With reference to FIG. 4, fluid quality data can be measured using portable sensor units 410A-410D at different locations corresponding to different points of fluid delivery. The portable sensor units 410A-410D can be handheld units, for example, such as those such as described in copending U.S. patent application Ser. No. 10/657,760 ("Method and Apparatus for Quantitative Analysis"), the entire disclosure of which is incorporated herein by reference. The portable sensor units 410A-410D can have any desired combination of various types of sensors such as disclosed in U.S. patent application Ser. No. 10/657,760 and/or as described elsewhere herein.

The different locations are controlled by separate entities 412A-412D, for example, residential entities, industrial entities, business entities and/or government entities, such as described elsewhere herein. For example, residential entities can include private homes, apartment buildings, and the like. Industrial entities can include industrial plants for power generation or manufacturing, for example. Business entities can include restaurants, retail outlets, drycleaners, and a host of other businesses. Government entities can include military installations and government research laboratories, for example. Fluid quality data (e.g., data obtained from potable drinking water from a water distribution system or well) can be obtained from locations of any combination of such entities 412A-412D, or from a single type of such entities, e.g., from businesses such as restaurants or drycleaners. The measurements are carried out by supply entities or service entities 414A-414D, who can be private or public entities. For example, a supply entity can be sales entity (including employees thereof) who sells water treatment products, such as water softening agents and/or soaps to restaurants and/or drycleaners. As another example, a service entity can be a water treatment company (including employees thereof) who services water treatment equipment located at the separate entities 412A-412D, a public water authority (including employees thereof) that reads and inspects water meters, or a public health entity (including employees thereof such as public health officials).

The portable sensor units 410A-410D are configured to establish wireless communication with one or more wireless transceivers 416A-416B (e.g., wireless towers). Raw fluid quality data and/or processed fluid quality data can be communicated from the portable sensor units 410A-410D to the wireless transceivers 416A-416B. Raw fluid quality data and/or processed food quality data can then be communicated from the wireless transceivers 416A-416B to a centralized data collection system 418 (e.g., an internet server) via suitable communication channels 419 (e.g., existing wireless, wired, optical networks, power-grid networks, or combinations thereof). Raw fluid quality data and/or processed fluid quality data and/or fluid quality measures derived therefrom can then be communicated to interested parties 420A-420D other than the separate entities 412A-412D via any suitable communication channel 421. For example, such interested parties can include a regional water authority 420A, a multi-regional authority 420B, the Department of Homeland Security 420D, and/or a host of any other interested entities 420D. In addition, the raw fluid quality data, and/or the processed fluid quality data and/or the fluid quality measures can also be communicated to the separate entities 412A-412D themselves (shown as box 412 for convenience), who are the original customers served by the supply or service entities 414A-414D. Other aspects relating to the processing, sharing and communication of data with interested parties as disclosed elsewhere herein can also be utilized to process, share and communicate data obtained from portable sensor units 410A-410D.

The sensor units 410A-410D can be equipped with global positioning system (GPS) devices for identifying the location of each of the portable sensor units 410A-410D. Alternatively, location information of each of the portable sensor units 410A-410D can be determined using triangulation from several wireless transceivers 416 that are in communication with a given sensor unit 410A-410D, if this service is provided by the wireless service provider. In this manner, both location data and water quality data can be obtained and communicated in real time to provide a map of water quality information at a given time (or times) at various locations of a water distribution system. Moreover, such information can provide information on the time evolution of water quality information over a geographic area encompassing a water distribution system.

In addition, data (including raw and/or processed data) obtained with such portable sensor units 410A-410D can be used in connection with fingerprinting algorithms, such as described elsewhere herein, for example, to determine contaminants and contamination states based upon comparing measurement data from a sensor unit or units 410A-410D to a database of "fingerprints" of contaminants or classes of contaminants. The database can be located at the centralized data collection system 418, for example, and/or such fingerprint information can be stored in the portable sensor unit, which can also be configured to provide a caution or alarm indication depending upon a measurement reading, such as described elsewhere herein, for example. Such fingerprints can be empirically determined, for example, by exposing the suite of different types of sensors of a sensor unit to a known contaminant and mapping the response of each of the sensors of the suite, the combined readings from the suite of sensors providing the fingerprint of the contaminant. To the extent that various contaminants of a class of contaminants may provide similar fingerprints, a fingerprint may also be associated with a class of contaminants. The fingerprint information in the database can also be tabulated to account for historical chemical information associated with a particular geographic site or sites (e.g., a given site may be known to have a certain chemical history that affects fluid quality measurements, such as water quality, in a particular way) such that whether or not a given reading can be viewed as matching the fingerprint of a contaminant can be based in part upon site-specific information of the geographical location from where the measurement was taken. Stated differently, adjustments can be made to a "fingerprint" to account for site-specific geographical information. Similarly, the fingerprint information can be tabulated to account for seasonal variations in fluid quality. For example, there can be seasonal variations in the water chemistry, and such variations can potentially affect the fingerprint of a contaminant or class of contaminants. Thus, adjustments can be made to a "fingerprint" to account for seasonal variations as well.

Moreover, information from multiple portable sensor units 410A-410D can be used to map the dispersion of a contaminant through a fluid distribution system (e.g., potable water distribution system), such as described elsewhere herein. Such information can be combined with known flow information of the fluid distribution system to determine the source of the contamination.

Such a data gathering and information sharing approach using portable sensor units has an advantage of not requiring modifications to any existing water distribution infrastructure or private water treatment infrastructure in order to gather and communicate water quality data. Rather, portable hand-held sensor units can be utilized by sales people or service technicians in connection with new and/or existing sales businesses and/or service businesses without the need for any modification of a customer's equipment. Moreover, given the large numbers of such existing sales or service entities, and given the low cost of portable sensor units as disclosed herein and in copending U.S. patent application Ser. No. 10/657, 760, water quality data can be obtained from large geographic areas encompassing complex water distribution systems with relative ease and minimal cost. Such information can be shared with a variety of interested parties such as water authorities, local and regional police departments, and national government agencies such as the Department of Homeland Security with minimal investments in capital and time by such agencies and their officials.

Any suitable technique or combination of techniques known to those of ordinary skill in the art can be used to very the authenticity and/or integrity of the data acquired and transmitted by the portable sensor units 410A-410D. For example, any suitable technique can be used to verify that the identity of a present user is an authorized user of the device.

Data Gathering, Access, Analysis and Visualization

Figure 5:
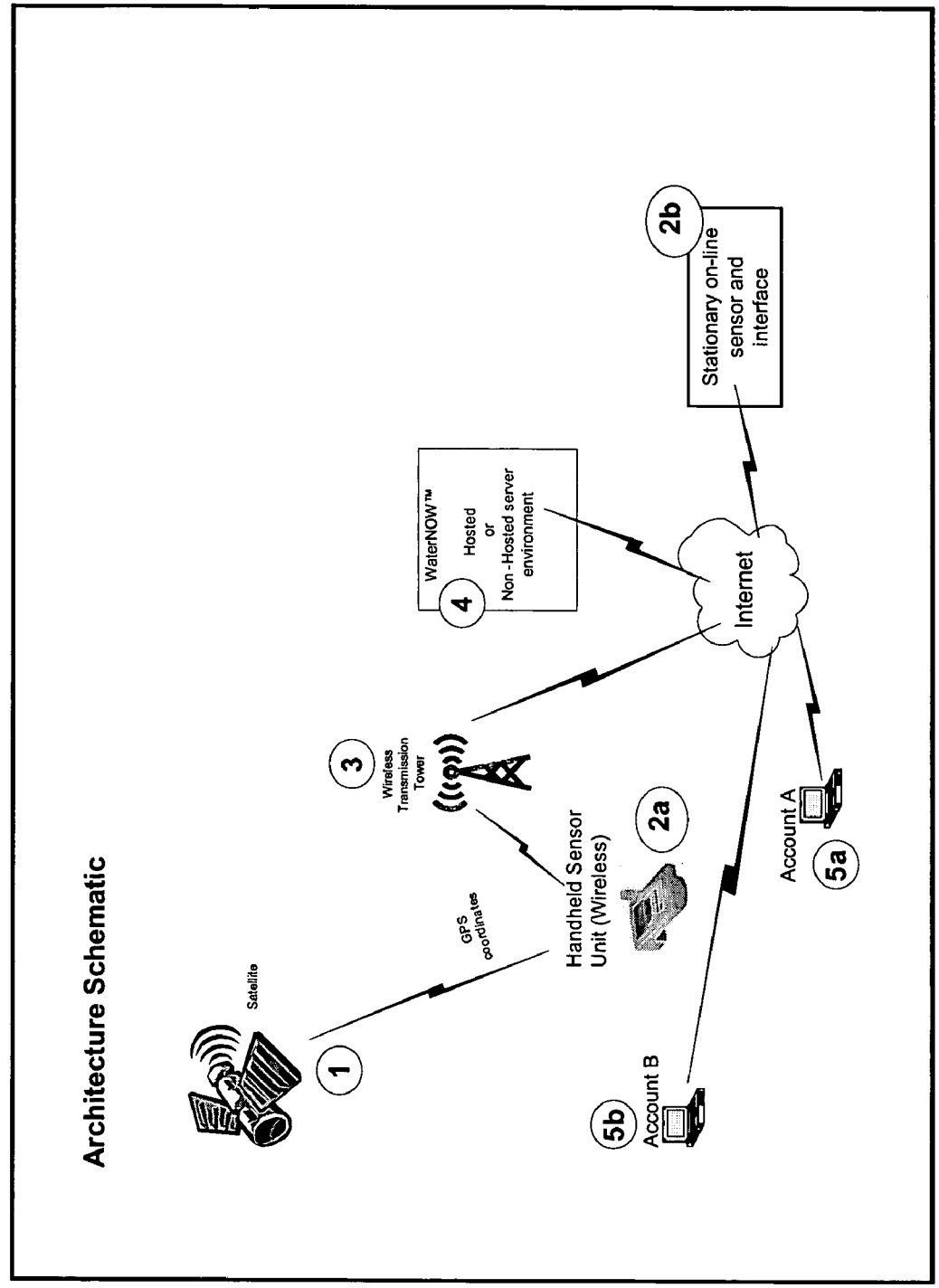

According to another embodiment, a system and method are provided which allows a computer system of a service provider to receive fluid test data (e.g., water test data associated with potable water) generated from multiple different entities and which permits authorized users affiliated with the different entities, as well as others, to visualize information associated with that data to via the Internet using graphical computer interfaces at their respective computers. FIG. 5 shows a schematic illustration of an exemplary system architecture in this regard. A computer system controlled by a service provider (e.g., Sensicore) is connected to one or more communication networks as well as the Internet using any suitable communications technologies and is equipped (programmed) with suitable software to be able to receive fluid test data from portable handheld sensor units 2a (via wireless tower 3) and/or wired or wireless stationary on-line sensor devices 2b via the communication network(s). The sensor units 2a and 2b can be equipped with a "confirm" capability as described elsewhere herein, if desired. Fluid test data can also be received by or uploaded to computer system 4 from other data systems or resources as will be described below.

Fluid test data refers to data associated with any measurable fluid property including but not limited to physical properties (e.g., temperature), chemical properties (e.g., presence of organic and/or inorganic chemical species), biological properties (e.g., presence of cryptosporidium, ecoli, etc.) and radiological properties (e.g., presence of radium, tritium, etc.). Fluid test data can be obtained using sensing methods such as described herein and can provide measures of fluid quality.

The handheld sensor units 2a are equipped with GPS units that cooperate with satellites 1 to thereby provide geographic location information of test locations as well as fluid test data to the computer system 4. The handheld sensor unit 2a also transmits its unique identifier (e.g., ID number) that has been registered with the computer system 4 along with its measurements. The geographic locations of stationary sensor unit 2b is also known or can be determined as described elsewhere herein, and this information can either be transmitted along with test results and its identifier to the computer system 4, or the location information can be stored on the computer system 4 and looked up when test data is received along with a unique identifier for the stationary sensor 2b.

As will be described further herein, an authorized Account A (first user 5a) can be authorized by a first entity (e.g., a municipal water authority) to access aspects of first fluid test data from the computer system 4 via the Internet using a graphical computer interface at a computer operated by first user (Account A). For example, first fluid test data may be that obtained by the wireless handheld sensor 2a, which is under the control of the municipal water authority. Similarly, an authorized Account B (second user 5b) second user can be authorized by a second entity (e.g., an industrial plant or power utility) to access aspects of second fluid test data from the computer system 4 via the Internet using a graphical computer interface at a computer operated by the second user (Account B). For example, the second fluid test data may be that obtained by the stationary sensor 2b, which is under the control of the industrial plant. In this regard, separate entities provide their fluid test data to the computer system 4 controlled by the service provider (an entity different from the first and second entities), and the first and second entities can control access to data generated by their respective sensors by accessing the software of computer system 4 through graphical interfaces at their respective computers.

As described further below, the computer system 4 permits Account A to visualize first information associated with the first fluid test data overlaid on a geographical map displayed on the graphical computer interface (e.g., a web browser) of Account A's computer. In this regard, the computer system 4 can provide either a hosted environment (e.g., act as an application service provider as known in the art such that Account A needs primarily only a suitable web browser) or a non-hosted environment wherein appropriate software issued by the service provider is run on Account A's computer to access computer system 4. Account B is similarly permitted to visualize data authorized by the second entity. It is also contemplated and desirable that various entities will grant authorization to visualize generated by them to others beyond themselves, such as government health organizations or security organizations such as the Department of Homeland Security.

One mechanism for selling such fluid monitoring and data access/visualization services is by providing a product and service combination comprising one or more sensor units (such as portable handheld sensor units having wireless communication and GPS, or stationary on-line sensor units as described elsewhere herein) as well as access to a hosted or non-hosted web-based service. A hosted web-based application service is further described herein and is referred to in FIGS. 5 and 6 as WaterNow™. Various options can be used for pricing the service. For example, the web-based application service can be provided for a monthly fee (or annual fee) without limitation on the number of test results communicated to the service and without limitation regarding access to features or time logged in. Also, the sensor units can be sold, leased or provided for free with a contract for monthly service (or annual service) for a given contract time period. Alternatively, a service fee can be charged based on service bundling wherein the price of the service depends on the level of service features purchased. As an example, a service package could be provided with or without extended "reporting" capabilities, such as those designed to meet requirements of the EPA or state government agencies. Packages sold with such extended reporting capabilities can be provided at a higher price. As another alternative, services can be sold on a test-number basis, e.g., a user is billed based on the number of test results communicated to the service. Also, a combination of such approaches can be used, e.g., a monthly service fee for a given feature package with otherwise unlimited uploading of test results and time logged in to the service.

As discussed elsewhere herein, it may be appropriate to pay some consideration to the entity in exchange for access to data generated by their sensors. One example is to provide a lower monthly service fee to the entity if data sharing is granted. Another example, may be to provide service without cost for some period of time based on an entity's commitment sharing of data generated by a given entity's sensor(s). Other approaches may also be used. Also, the service provider and a given entity can agree in a service agreement that the service provider retains a right to share data generated from the entity's sensor unit and loaded into the service provider's computer system even after the entity ceases to utilize the service provider's services.

Moreover, it will be appreciated that any suitable commercial or other product distribution channel as described elsewhere herein can be used to sell sensor units and monitoring services including the data access and visualization services to customers including software distribution chains, for example.

Figure 6:
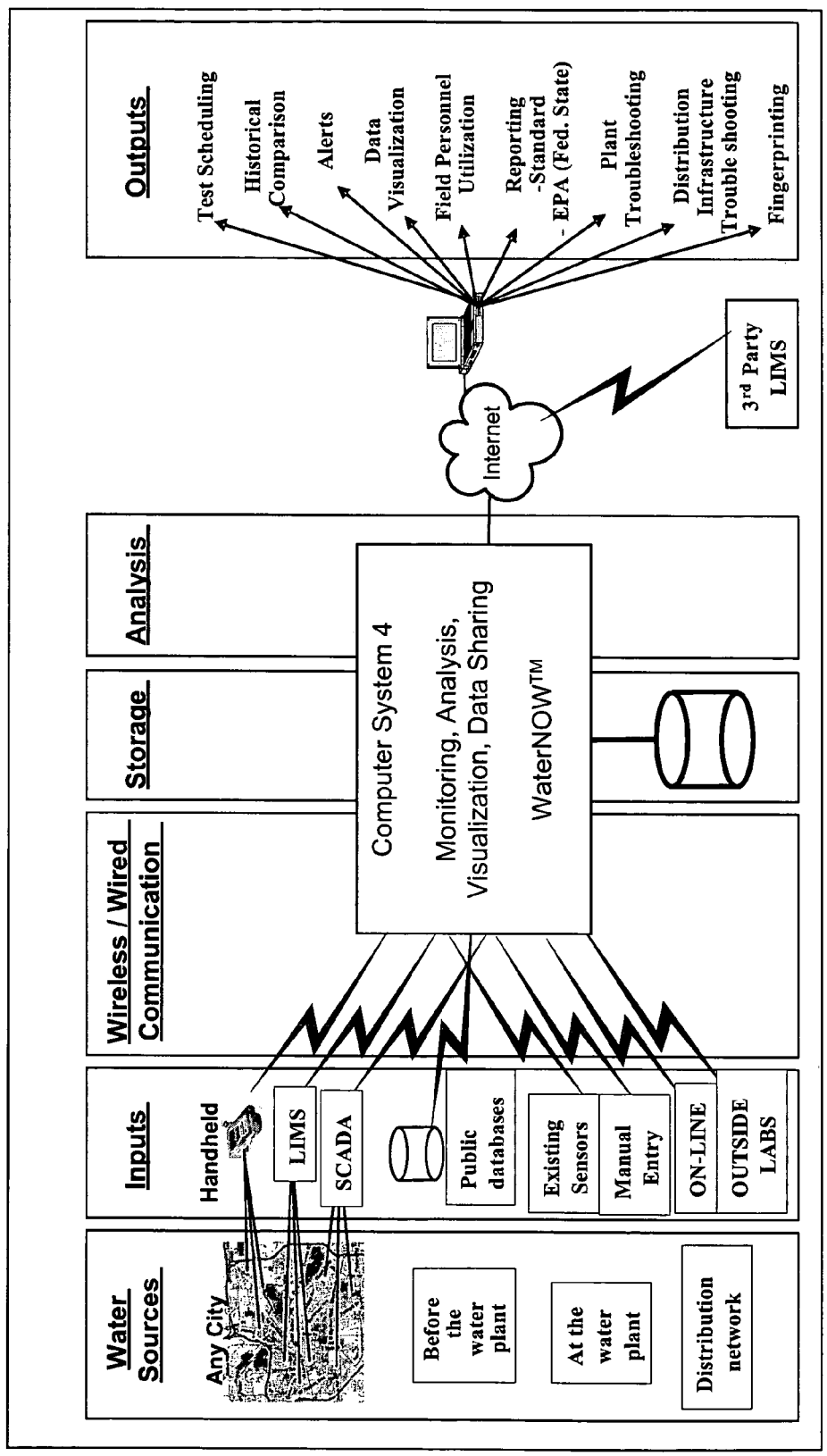

As illustrated in FIG. 6, fluid test data received by computer system 4 need not come solely from sensor units such as portable handheld sensor units or other on-line stationary sensor units with either wired or wireless communication capability. Rather, fluid test data can also come from laboratory information management systems (LIMS) which are systems that store data which can be submitted (e.g., uploaded) electronically to computer system 4. A LIMS might be associated with an internal chemistry laboratory of a municipal water authority or could be that of an independent contracting laboratory. Fluid test data can also be provided by a supervisory control and data acquisition (SCADA) system; for example, such data might be that generated from on-line sensors inside a physical power plant or other industrial plant).

Data might also come from public databases such as those controlled or maintained by the Environmental Protection Agency. Such data need not be restricted to fluid test data but can also include, for example, medical data associated with diseases statistics in a given geographic area, weather data for a given geographic area, or historical environmental data (e.g., of Superfund sites). Such data can also be visualized by authorized users and can assist in understanding how water quality may be impacted by other environmental circumstances, and how water quality may be impacting public health.

Data might also come from existing sensors such as other sensors placed in the field by municipalities (e.g., sondes) or any other suitable on-line sensor such as those described elsewhere herein (e.g., those placed in businesses and residences).

Data might also be input to computer system 4 by manual entry based on a wet chemistry analysis by a laboratory from a "grab sample" taken in the field. Data from outside laboratories (e.g., independent contracting laboratories) can be provided to computer system 4, for example, by manual entry, uploading of spreadsheet data, or electronically from the laboratory's LIMS system.

In any of the above-noted possibilities, the data can be communicated to the computer system 4 via wired and/or wireless communication over suitable networks including the Internet. This data is then stored and analyzed using software at computer system 4, and is ultimately shared with others such as authorized users, third party LIMS, municipal water authorities or other municipal agencies (e.g., local health departments and police departments), and/or government agencies in a manner that allows powerful visualization of single-entity data or shared data. Among the outputs and/or benefits that are provided directly or indirectly to such users are test scheduling (e.g., to assist a municipal water authority in adhering to test schedules governed by EPA rules), providing historical comparison of single-entity or shared data (e.g., historical changes in such data), alerts for out-of-bound or alarm conditions, data visualization, decision making for efficient utilization of field personnel, reporting (e.g., according to standards for the EPA, state or local requirements), plant trouble shooting, troubleshooting of water distribution infrastructure (e.g., broken pipes), and fingerprinting of contaminants or classes thereof (such as described elsewhere herein and as known in the art).

Figure 7:
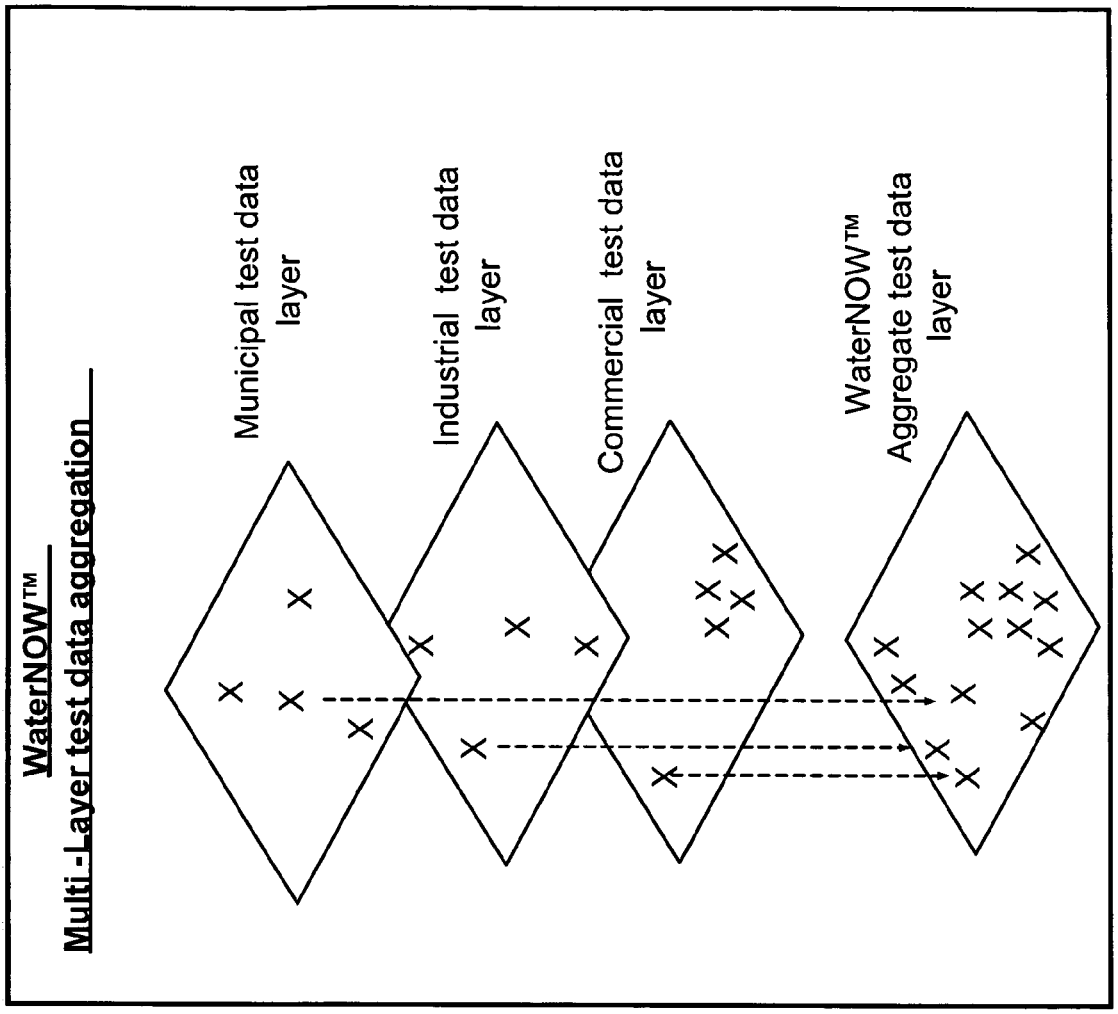

It will be apparent from the discussion above that by obtaining fluid test data from multiple different types of entities (municipal entities, industrial entities, commercial (business) entities, the software (WaterNOW™) implemented on computer system 4 can aggregate data from various layers of entities make all or only some of that data available to all or only some authorized users depending upon the preferences of the entities as specified by the entities when their WaterNOW™ accounts are set up. This aggregating of data in multiple layers is illustrated in FIG. 7. When an administrator for a given entity establishes a WaterNOW™ account (e.g., via a web browser by accessing Sensicore's website), the administrator can specify who, if anyone, the fluid test data generated by that entity will be shared with.

Exemplary aspects of a web-based graphical interface (also called a graphical computer interface) displayed on a display screen of a computer system operated by an authorized user will now be described in connection with the WaterNOW™ system referred to previously. The term "graphical computer interface" includes within its scope a collection of hierarchical interactive screen displays (or pages) linked together in a manner that allows navigation between those pages, and may be either hosted or non-hosted (in the former, the requisite software resides primarily on the service provider's computer system 4, but software routines to facilitate navigation and interaction can exist on the user's computer as well; in the latter, the requisite software exists primarily on the user's computer). It will be appreciated that the drafting of appropriate software structures to implement the techniques described below is within the purview of one of ordinary skill in the art based upon a description of the pages presented below. For example, any suitable languages such as HTML, XML, JAVA, etc. can be used in this regard.

Figure 8A:
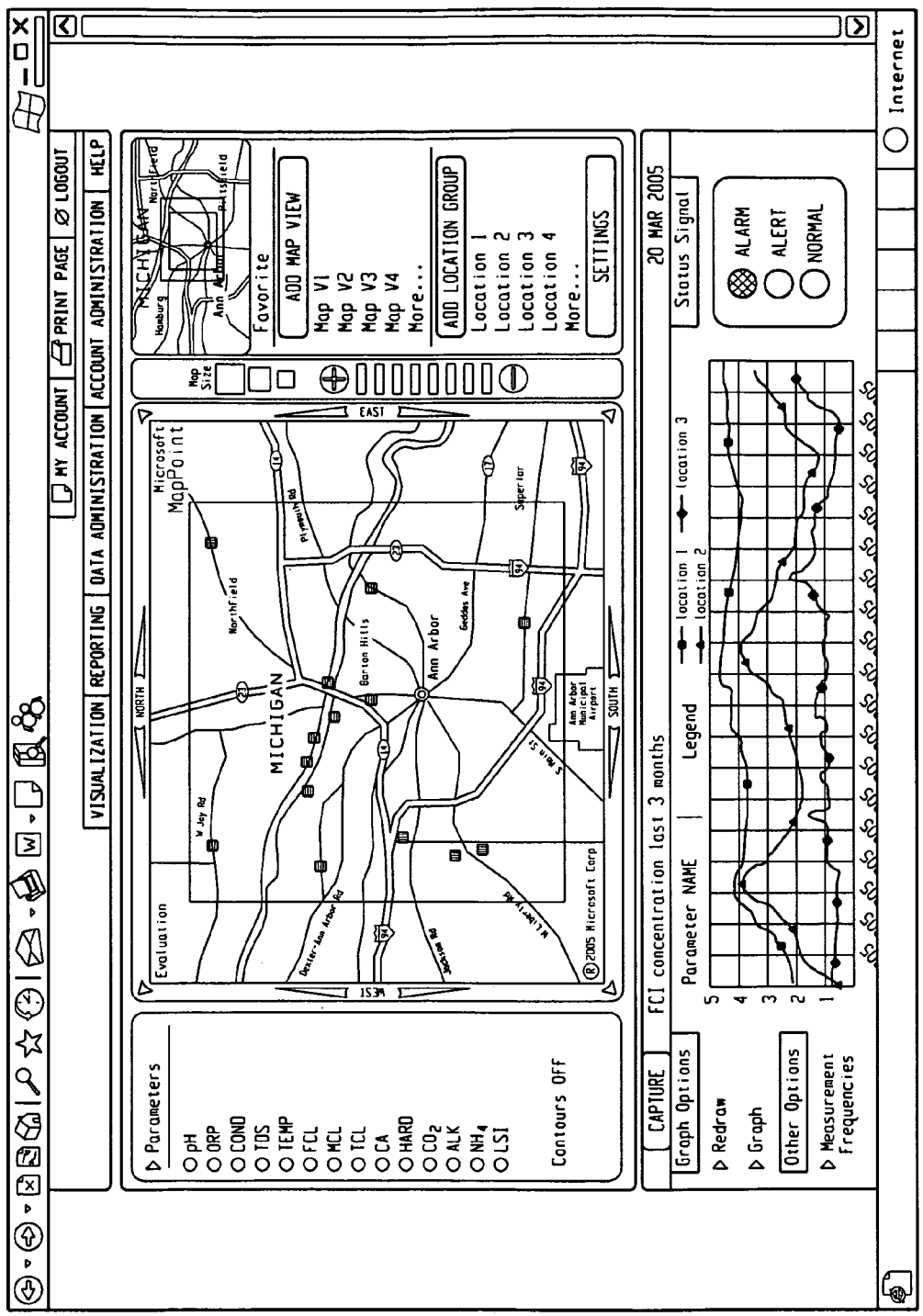

In the present example, it is assumed that an entity has purchased the WaterNOW™ service, and an administrator has created a user account for an authorized user (the administrator can be the authorized user, for example). It is also assumed that the user has been granted permission to observe information associated with fluid test data from one or more sensors are or have been in use over some time frame in some geographical area, such as handheld wireless sensors with GPS. These aspects will be further-discussed below. After the user has "logged in" to the service by inputting a username and password in a conventional manner, a page such as that shown in FIG. 8A is displayed. This main page has tabs across the top such as VISUALIZATION, REPORTING, DATA ADMINISTRATION, ACCOUNT ADMINISTRATION, and HELP. Also, a map is displayed of a given geographic area (whose boundaries are specified by the administrator during account setup). Shown on the map are squares associated with fluid test measurements which the user is authorized to see. The map is interactive in a manner commonly encountered with various web-based applications such that the user can zoom in or out and can shift the map to different locations. At the left of the screen shows various fluid test parameters that can be selected by the user by "clicking" on them with a computer mouse as such clicking is known in the art. At the bottom of the screen is displayed a graph of selected parameters for selected locations. The locations displayed in the graph can be selected by clicking on the map or by clicking on locations listed at the right of the screen. Clicking the CAPTURE button allows capturing the graph displayed so that it can be exported to a report or other software package, for example. When different parameters and/or locations are selected, the graph can be redrawn by clicking on "Redraw". Also, other graphing options can be obtained in a new window (a new screen that pops up) by clicking on "Graph".

Figure 8B:
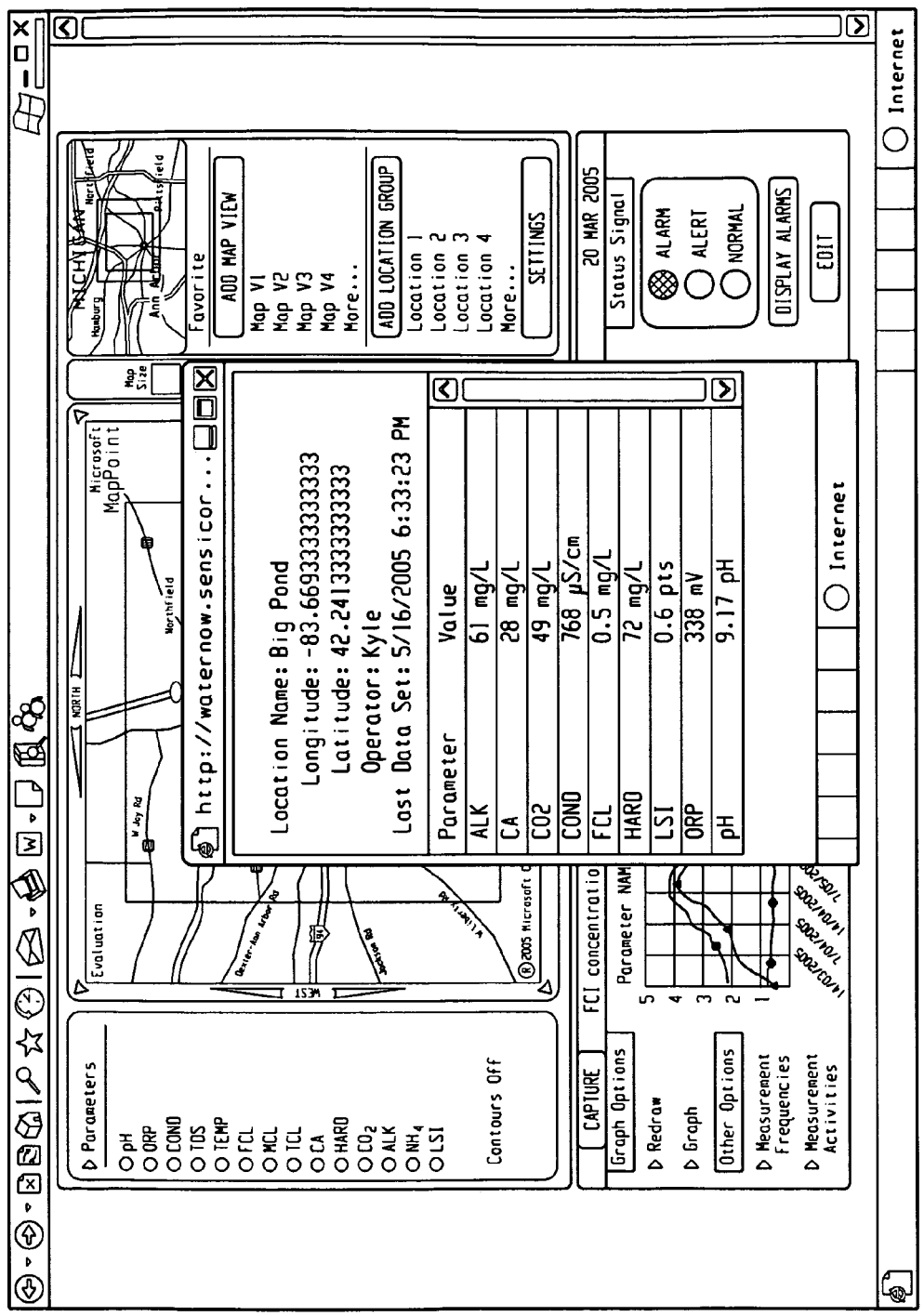
Figure 8C:
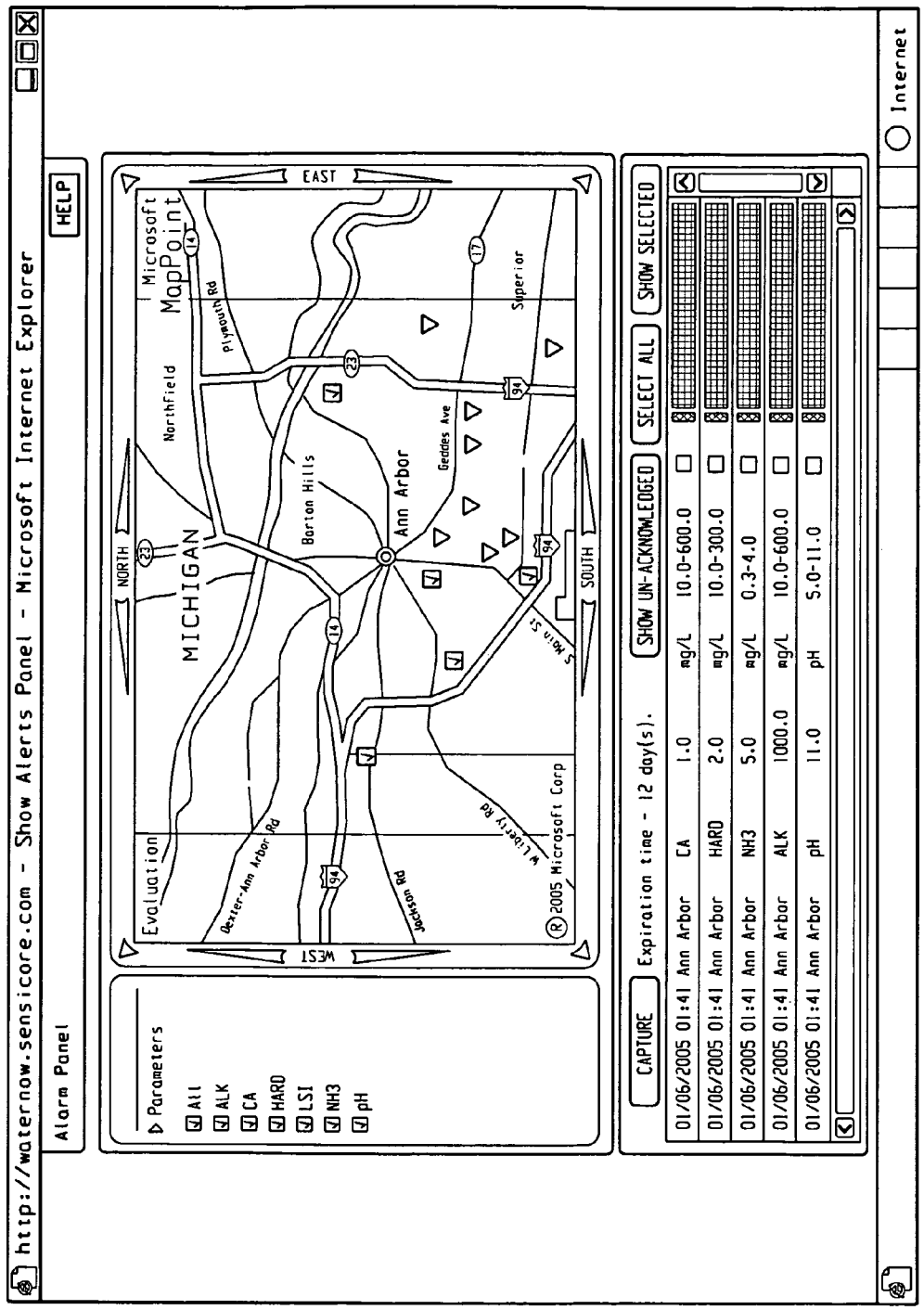
Figure 8E:
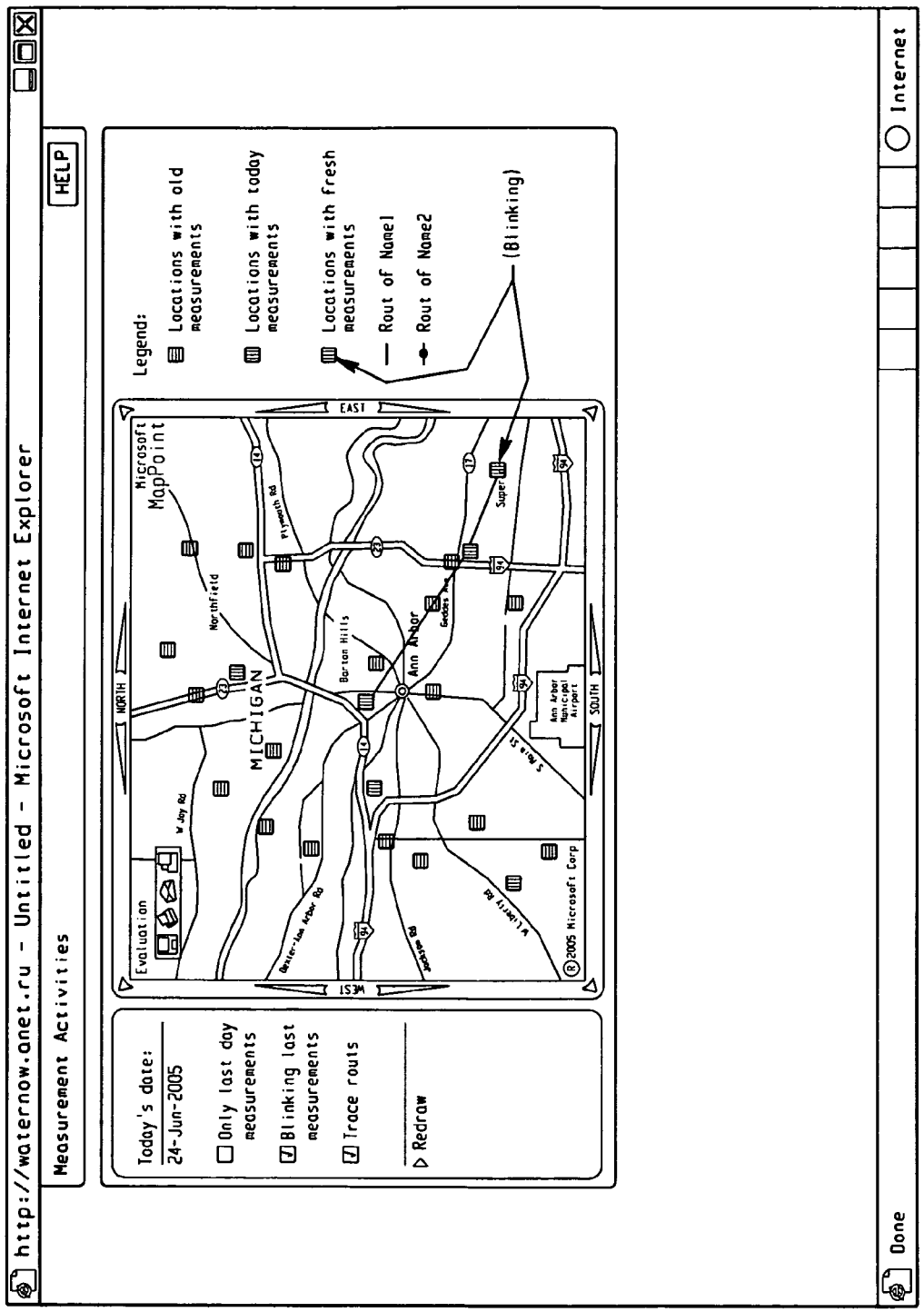
Figure 8F:
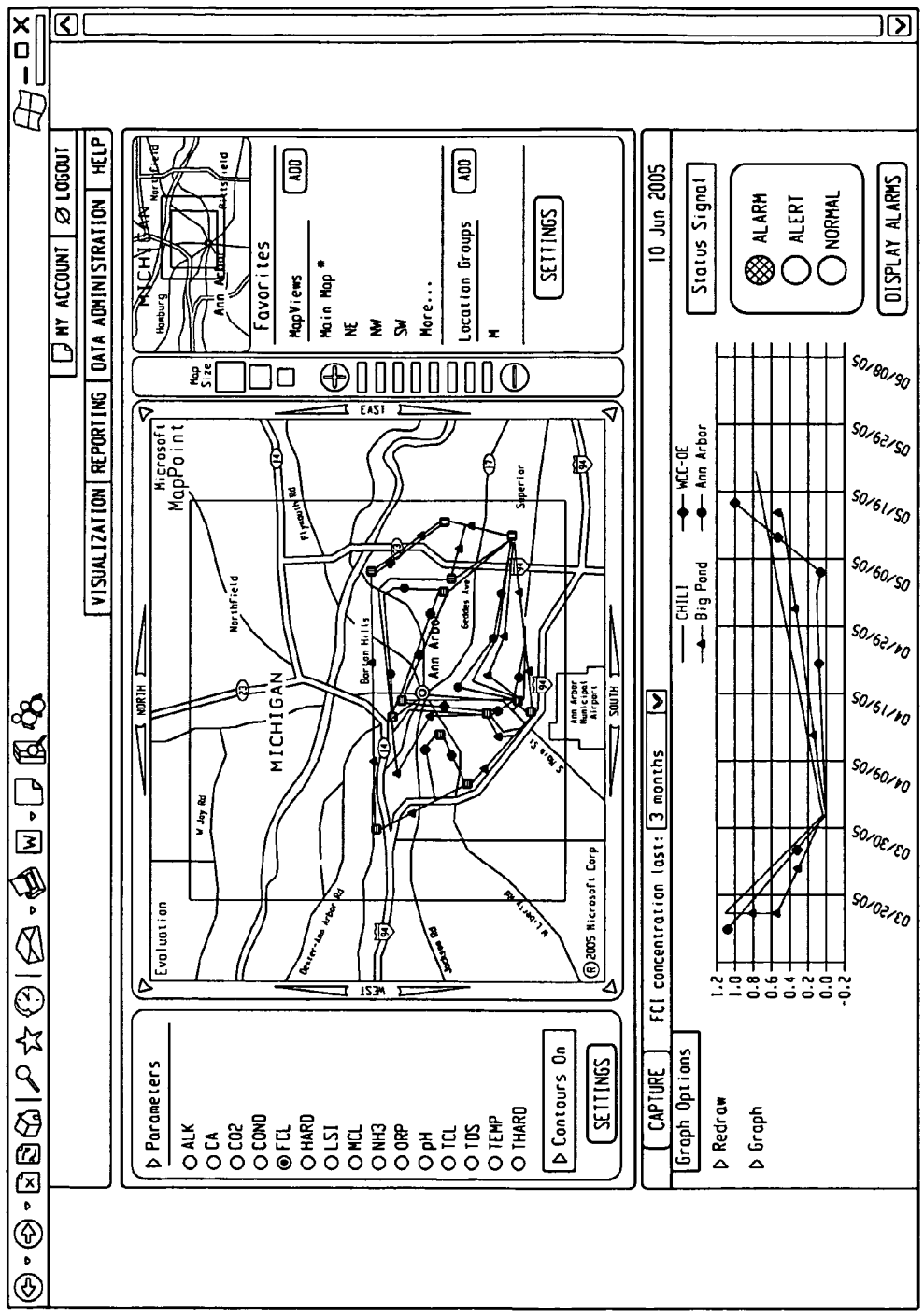
Figure 8G:
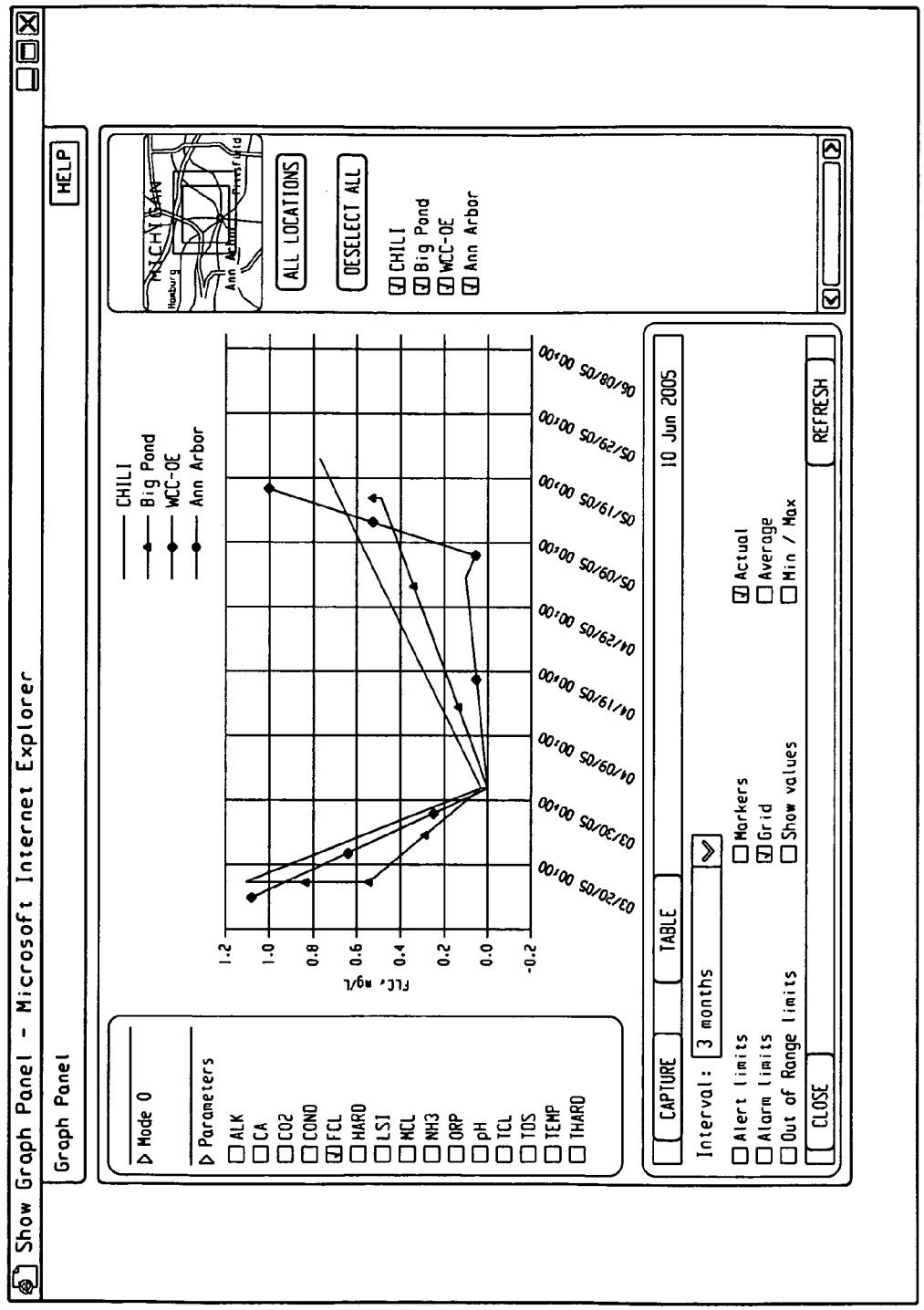
Figure 8H:
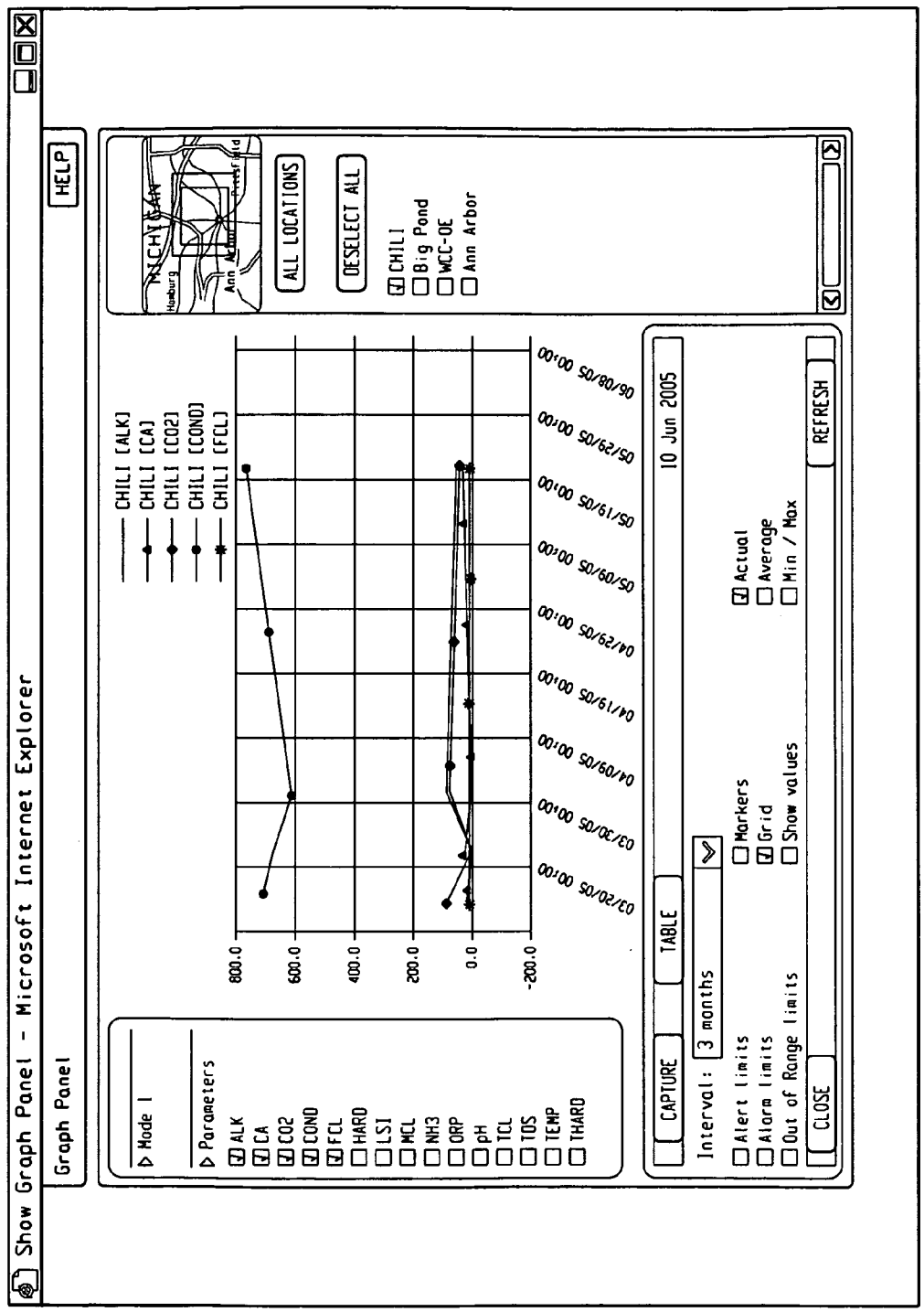

In this regard by clicking on "Graphs" shown in FIG. 8A, a new screen such as that shown in FIG. 8G is displayed. FIG. 8G shows an option at the top left referred to as "mode". "Mode 0" is displayed by default and corresponds to a graph of one selected parameter for multiple locations. Clicking the "mode" link causes "Mode 1" to appear, as shown in FIG. 8H, which corresponds to a graph of multiple selected parameters for one location. Different parameters, of course, can be selected by the user, and in addition, functionality can be provided to allow the user to further define other types of desirable graphing options.

In addition to viewing conventional measurement data, the software that implements the graphical computer interface system can also provide advanced analysis functions. For example, a user can specify that a real-time Langelier saturation index known to those of ordinary skill in the art be calculated and displayed. Moreover, the software can include functionality that allows a user to mathematically define new parameters based on suitable combinations of measured parameters (e.g., combinations using functions such as addition, subtraction, multiplication, division, powers, trigonometric functions, logarithmic functions, etc.). In this way, further analysis of measured data can be provided (e.g., a difference between free chlorine (FCL) and oxidation reduction potential (ORP) can be generated in real time). In addition, such combinations of parameters, or rates of change of such parameters (or rates of change of measured parameters) can be used to define suitable alarm and/or alert conditions (i.e., alert and/or alarm conditions can be defined statically and dynamically). Moreover, as described elsewhere herein a database (e.g., proprietary) of chemical fingerprints based on empirical responses of multiple parameters to known contaminants or classes of contaminants can be included in the analysis capability of the software, and observation of a parameter set indicative of a contaminant fingerprint can be used as a basis for an alert notification or an alarm notification.

In addition, by clicking on a particular square on the map, a window such as shown in FIG. 8B will appear, which provides specific information about the location selected, for example, longitude and latitude (e.g., as determined by GPS), the operator of the sensor, the date and time of the last test, and a listing of the values for the selected parameters from the last test.

As noted previously, handheld sensor units such as those described elsewhere herein can be used to make fluid tests. The fluid test data associated with a given measurement can be initiated by a suitable push-button stroke and/or navigating a suitable menu on the display of the sensor unit. When the measurement is completed it can be "accepted" by a suitable menu navigation and/or push button stroke. When accepted, the measurement result is automatically transmitted via wireless communication to the computer system 4 (see FIG. 5) along with the handheld sensor unit's unique identifier. If a wireless communication is not currently available, the measurement can be stored in the handheld unit until a wireless link is established.

As described elsewhere herein, alert and alarm thresholds can be chosen and entered into the graphical computer interface (as discussed further below), and alarm and alert events that are generated from data based on those thresholds are stored by the computer system 4 and can be accessed by a user by clicking on the ALARM or ALERT buttons at the bottom right of the screen shown in FIG. 8A. The NORMAL button can also be selected to view data within normal ranges. If the ALARM button is clicked, for example, a page such as that shown in FIG. 8C is displayed. This page includes a map such as described previously as well as a table at the bottom of the screen listing dates and times, locations, parameters, measured parameter values, and normal ranges for the selected parameters for alarm conditions that were recorded. A graphical "gauge" of the various normal ranges, alert ranges, and alarm ranges can be viewed in bar graph format at the bottom right of the screen. A user can "acknowledge" an alarm condition by clicking the check box to the left of the bar graphs at the bottom of the screen, and doing so allows the user to enter a description of the conditions associated with the alarm (e.g., to explain that a malfunction occurred and that a true alarm condition did not occur). By clicking on the box SHOW UN-ACKNOWLEDGED, a user can view alarm conditions that have not been acknowledged/explained.

Another option that can be selected from the main page (e.g., shown in FIGS. 8A and 8B is "Measurement Frequencies". Clicking on this selection brings up a page such as shown in FIG. 8D, which displays a schedule of tests that have been done and/or need to be done and/or are past due (e.g., to allow a user to check whether an entity such as a municipality has met its government testing schedule requirements). These testing schedules can be set up by the administrator during initial account setup and can be edited by an administrator or other user with proper authorization.

Another option that can be selected from the main page (e.g., shown in FIGS. 8A and 8B is "Measurement Activities". Clicking on this selection brings up a page such as shown in FIG. 8E, which displays a map of test locations with boxes color and/or shape coded according to the age of most recent tests at selected locations. Also, a feature (click box at left) can be selected wherein the most boxes associated with the most recent measurements (or those within a recent time frame such as 10 minutes) blink. Also, a feature can be selected wherein lines are automatically drawn between boxes to trace the routes of tests carried out by a given field testing individual with a given handheld unit (e.g., to geographically trace the progress of a given field testing individual to ensure that suitable progress is being made over the course of a day).

Another option that can be selected from the main page (e.g., shown in FIGS. 8A and 8B is "contours" by clicking the "Contours Off" button, thereby activating contours to "On" which redisplays the map but with contour, such as shown in FIG. 8F. FIG. 8F shows a display of the map with colored contoured lines to indicate equal concentrations of a selected parameter and then outlining hot spots, for example, areas in a municipality that have low free chlorine concentrations. An advantage is that such contours provide the ability to see a parameter-concentration distribution for an entire area using one chart, instead of having to process multiple charts to gain a similar appreciation for the distribution.

Figure 9A:
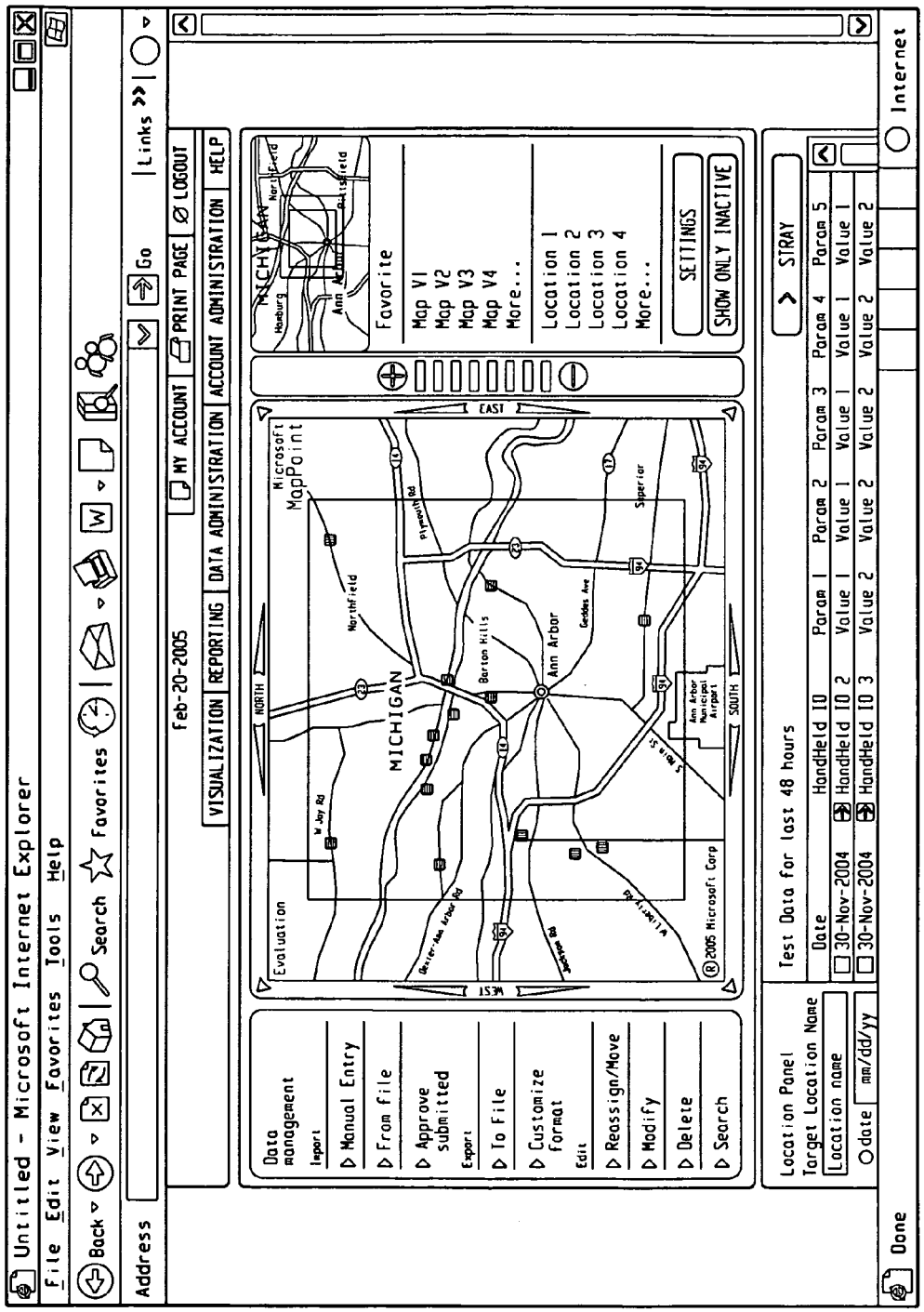
Figure 9B:
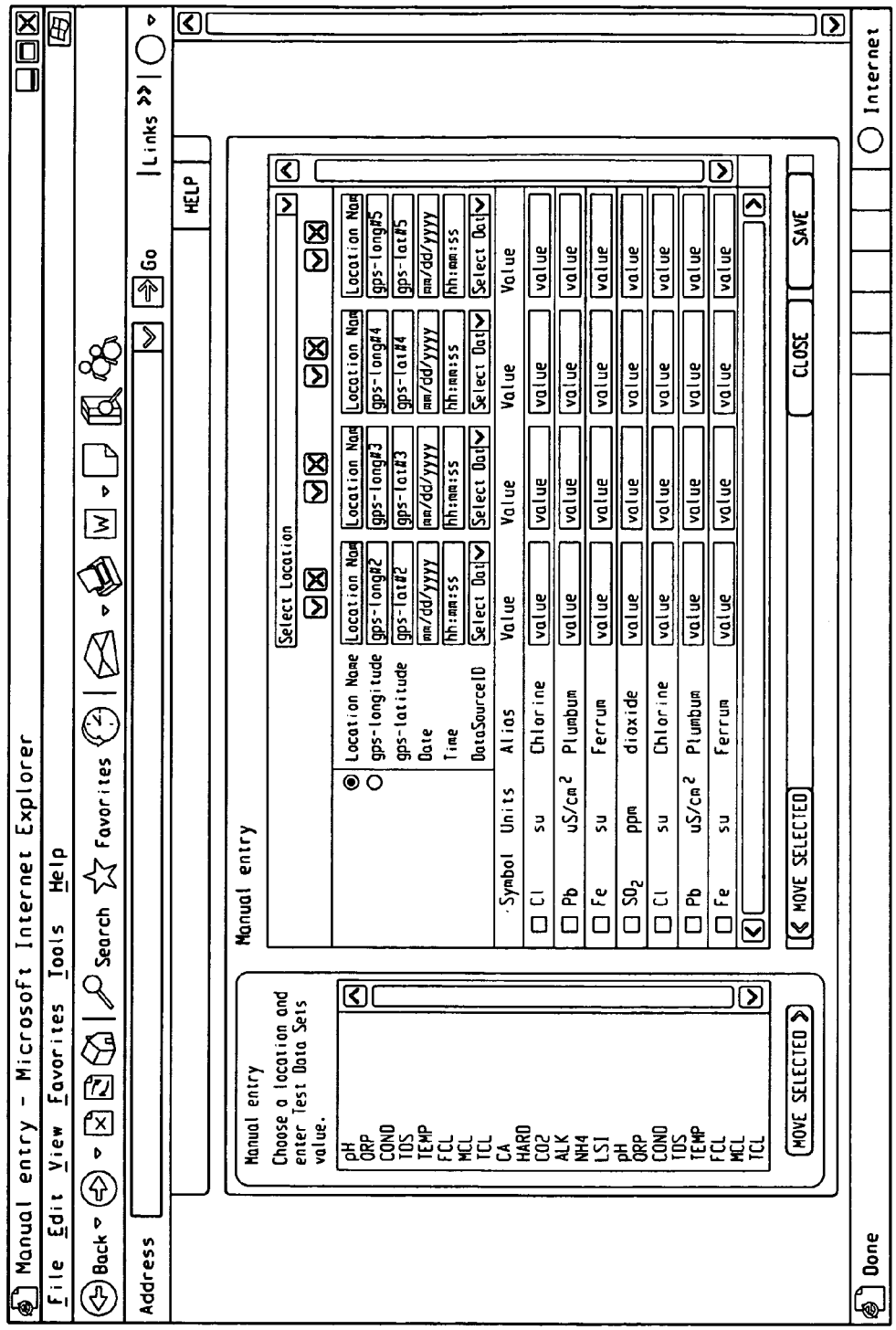

Referring back to the main page shown in FIG. 8A, if the DATA ADMINISTRATION link at the top of the page is clicked, a screen such as shown in FIG. 9A is displayed. This page also displays a map as well as data from various handheld devices associated with the logged in user's permissions. Clickable options present in this page include importing data by manual entry and/or by uploading from a file (e.g., a spreadsheet). An example of a manual entry screen that appears when the "Manual Entry" link is clicked is shown in FIG. 9B. This screen might be used for example, if the field tester also obtains a grab sample at the same time an electronic measurement is done and later has that sample tested by conventional wet chemistry. For an administrator or user with appropriate permissions, a link to "approve" the manually submitted data is provided. Also, data can be exported in a conventional manner by clicking "To File" and choosing a preexisting format in the screen that appears, or by clicking "Customize Format" and specifying a desired format in a screen that appears.

Figure 9C:
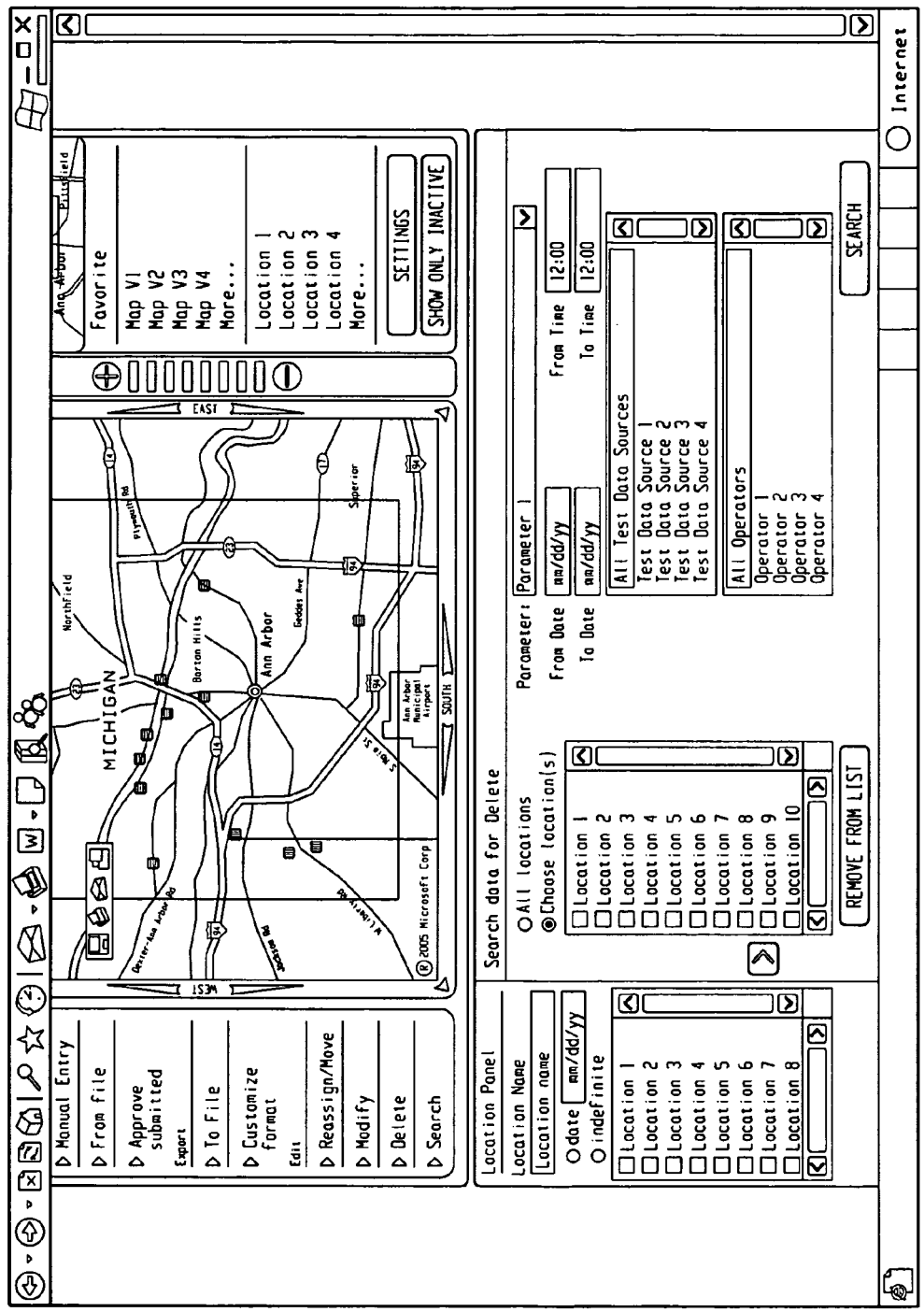
Figure 9D:
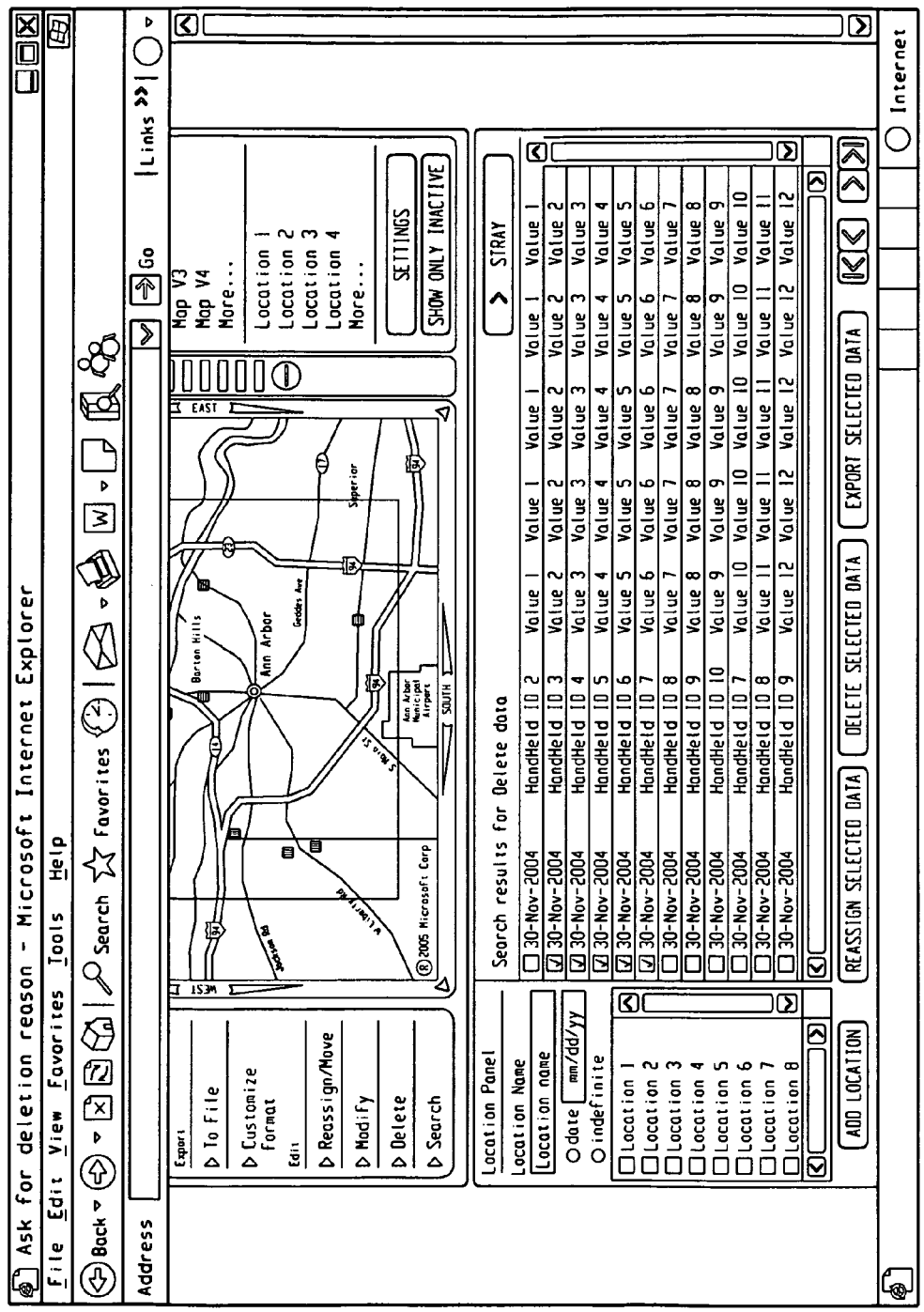
Figure 9E:
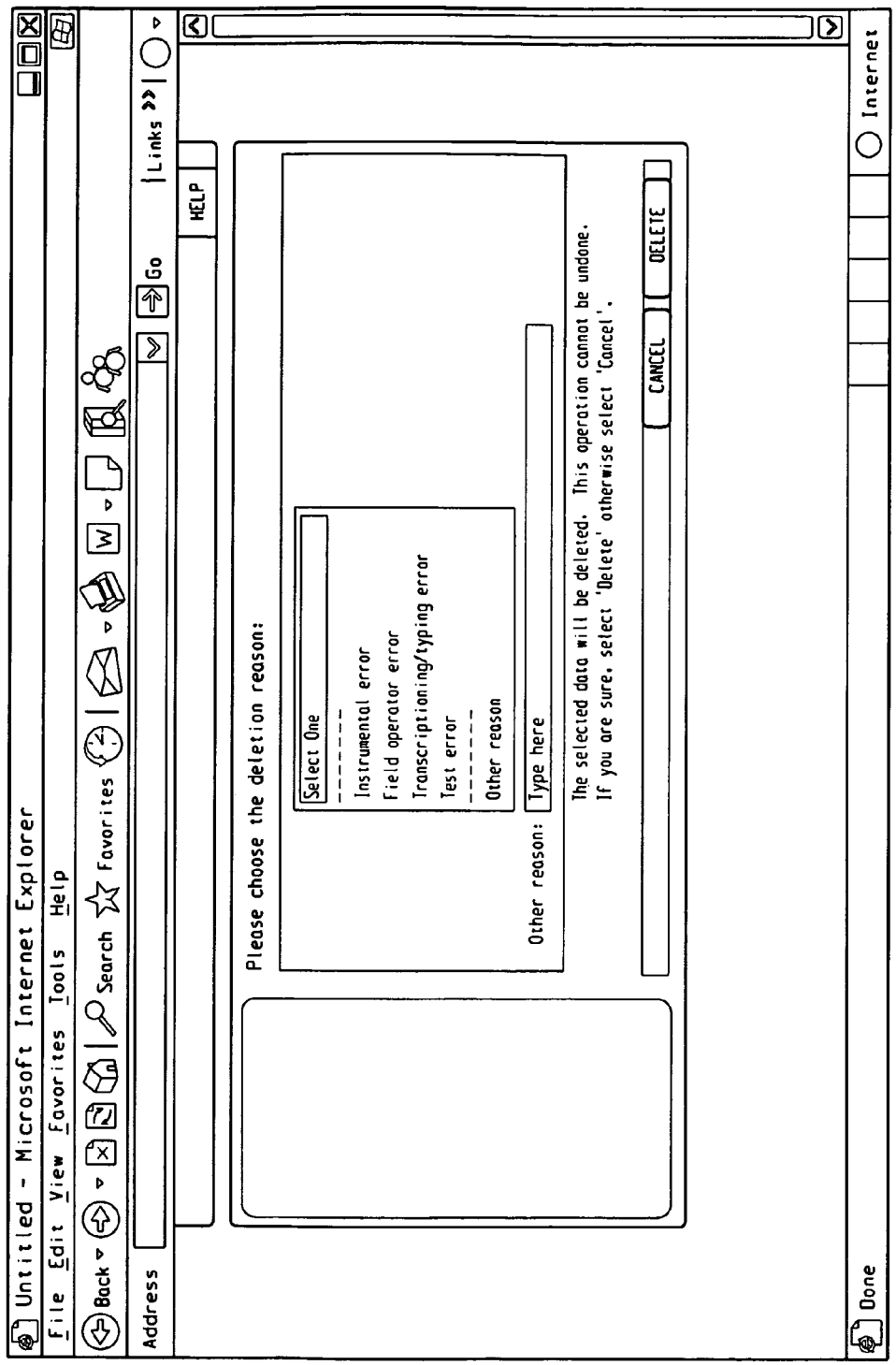

Also, if the user has appropriate permission, data can be edited by selecting one of the links labeled "Reassign/Move", "Modify", "Delete", or "Search" shown in FIG. 9A. For example, if "Delete" is selected, a screen such as that shown in FIG. 9C appears. First, the user searches for the data to be deleted by selecting some appropriate data aspects, such as shown at the bottom of the screen, and clicking SEARCH. This will bring up a list of search results such as shown in the screen shown in FIG. 9D, certain ones of which can be manually selected by clicking the check box(es) at the left, and by clicking DELETE SELECTED DATA. As shown in this page, data can also be reassigned to a new location (e.g., if there was a previous location error for some reason) at this point, and data can also be exported at this point as well. Clicking the DELETE button brings up a page such as shown in FIG. 9E, which prompts the user to specify the reason for the deletion by selection or by adding other comments. This feature can be used to ensure the integrity of the data in the database by requiring explanations for certain actions as well as approval by an administrator. A similar screen hierarchy can be used for location "reassignments".

Figure 9F:
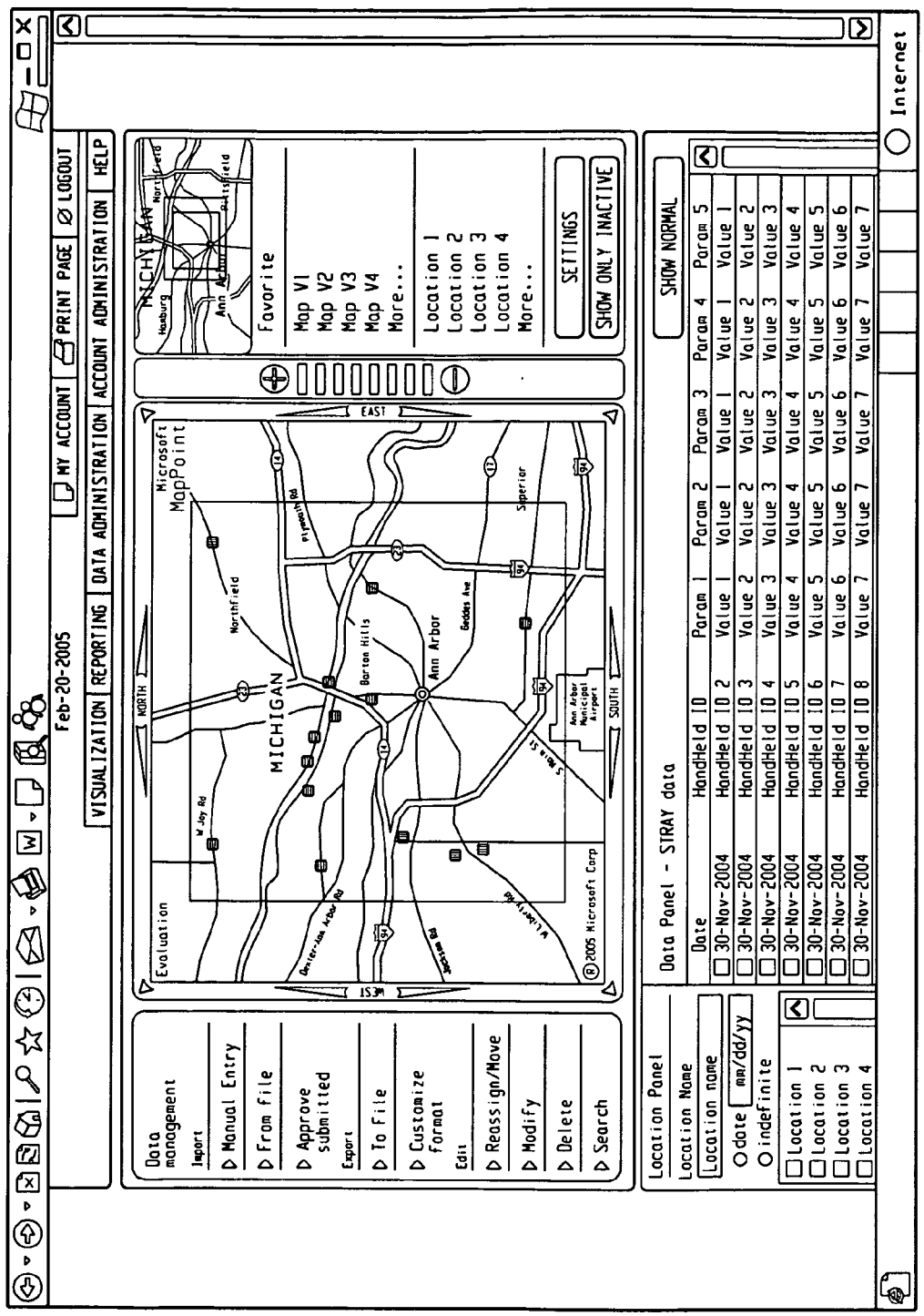

In the screen shown in FIG. 9A "STRAY" data can also be view by clicking on this link. Stray data refers to data that is obtained at a location outside the geographical region specified for a given handheld sensor unit, this region being specified by an account administrator at the time of setup or later edited. Specifying such geographic boundaries can be useful because municipal water authorities for example, have geographic boundaries to their authority. Thus, specifying geographical limits on where a given sensor unit should be able to take measurements provides another check on the integrity of the data obtained. Clicking this button brings up a screen such as shown in FIG. 9F, which provides a user the opportunity to view such stray data and which provides an administrator, for example, for the opportunity to reassign the location of such data if it is determined by some means that a "stray" designation is mistaken. This reassignment can be carried out, for example by, by clicking on (e.g., highlighting) certain results in the table shown in FIG. 9F, dragging those results to the map above with the computer mouse, and "dropping" the results onto a specific location on the map by releasing a mouse button. Such "drag and drop" operations can also be used in general across all data administration tasks for creating and updating data sets.

Figure 10A:
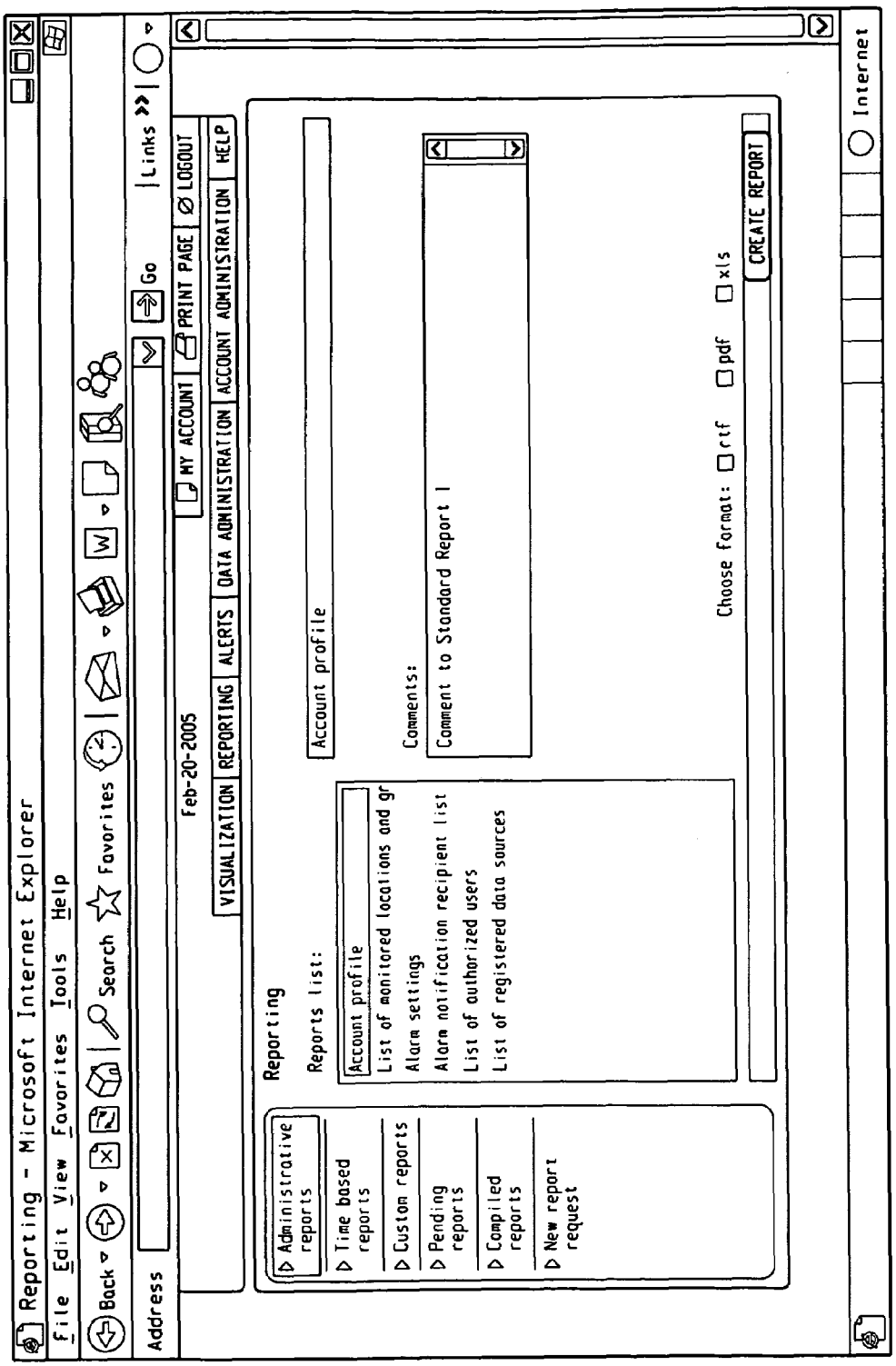
Figure 10B:
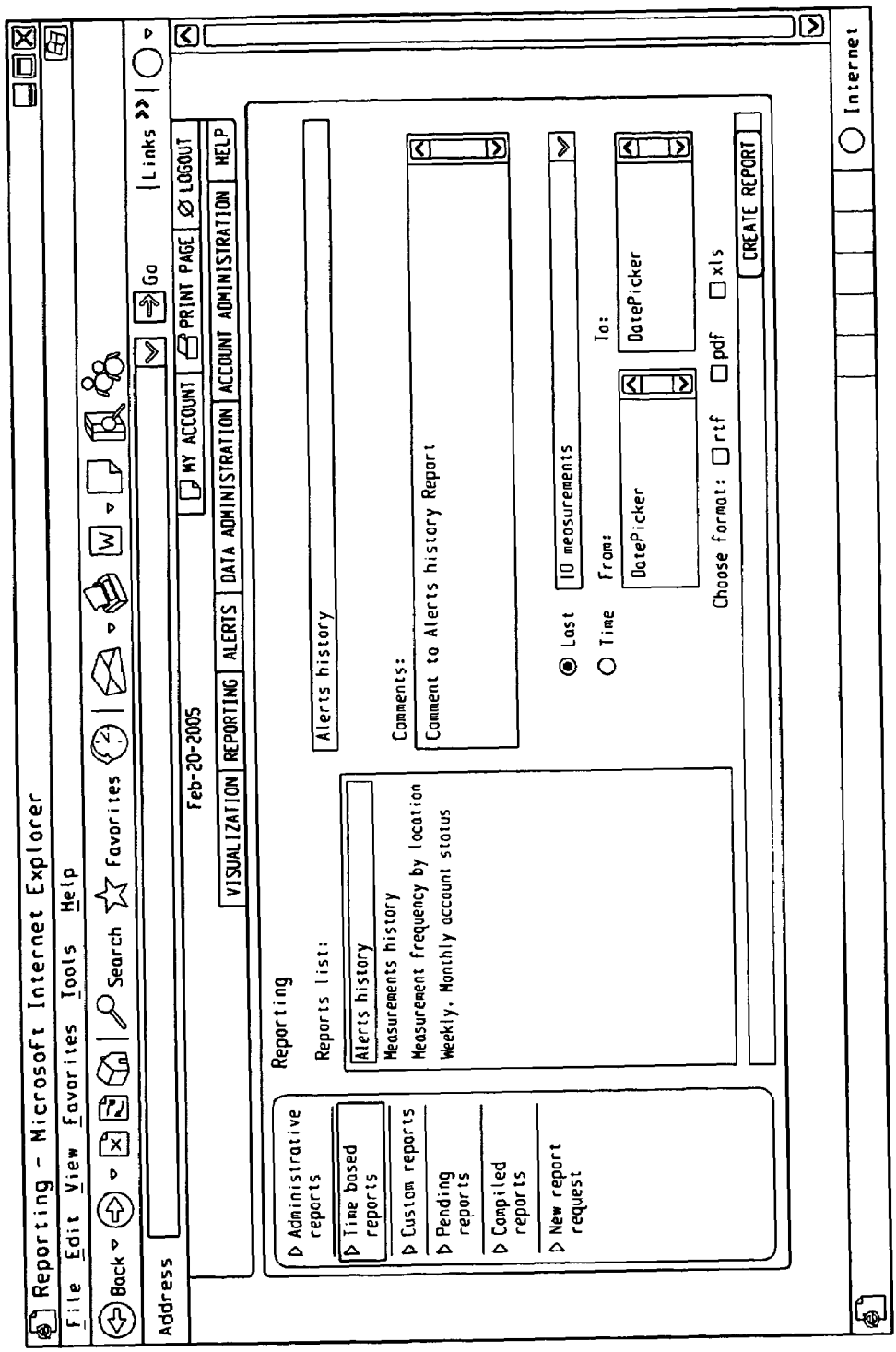
Figure 10C:
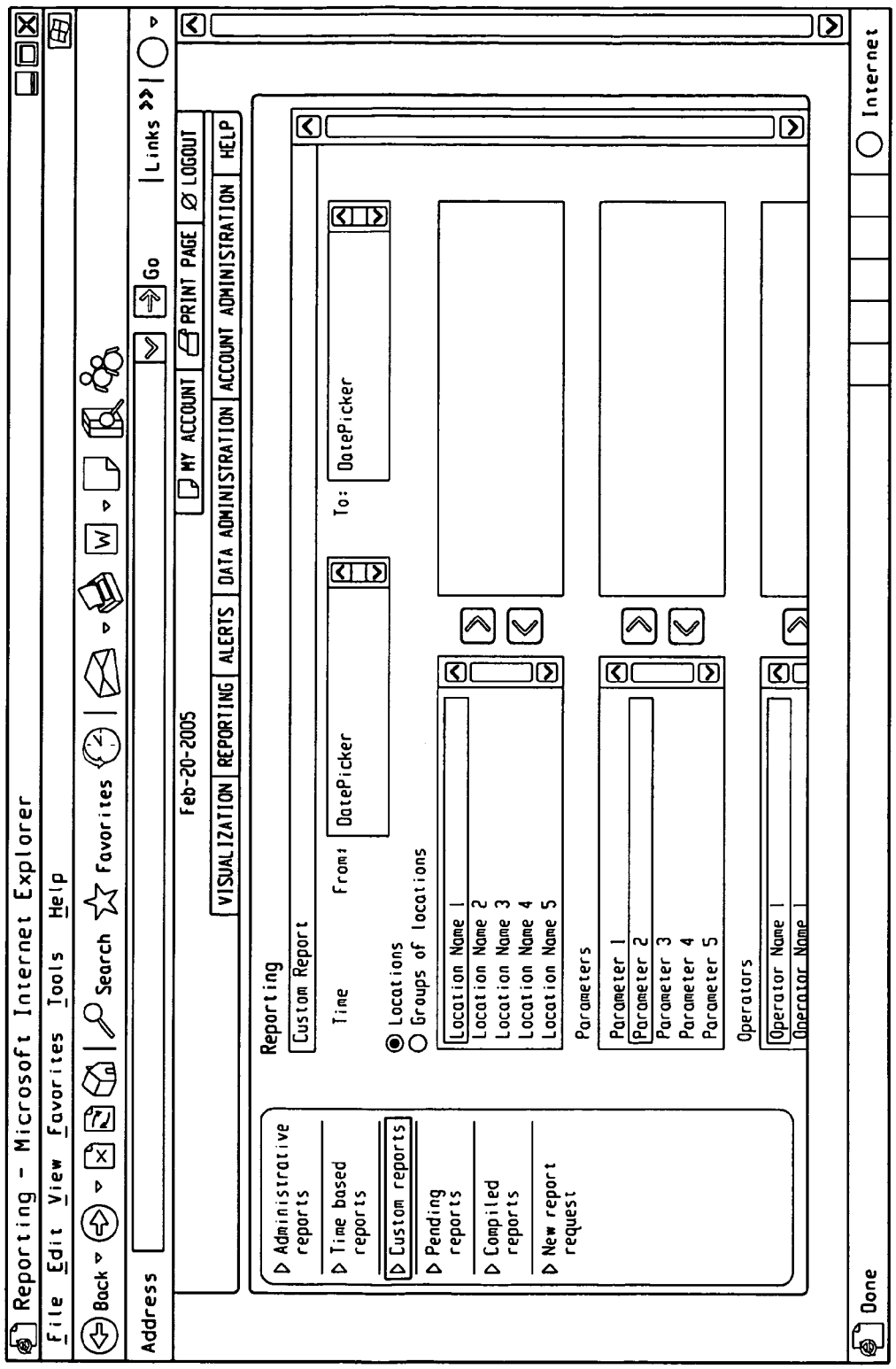

Referring back to the main page shown in FIG. 8A, if the REPORTING link at the top of the page is clicked, a screen such as shown in FIG. 10A is displayed. Clicking the various options at the left of the page (e.g., Time Base Reports, Custom Reports, etc.) returns other screens such as shown in FIGS. 10B and 10C which allow specifying types of reports desired.

Figure 11A:
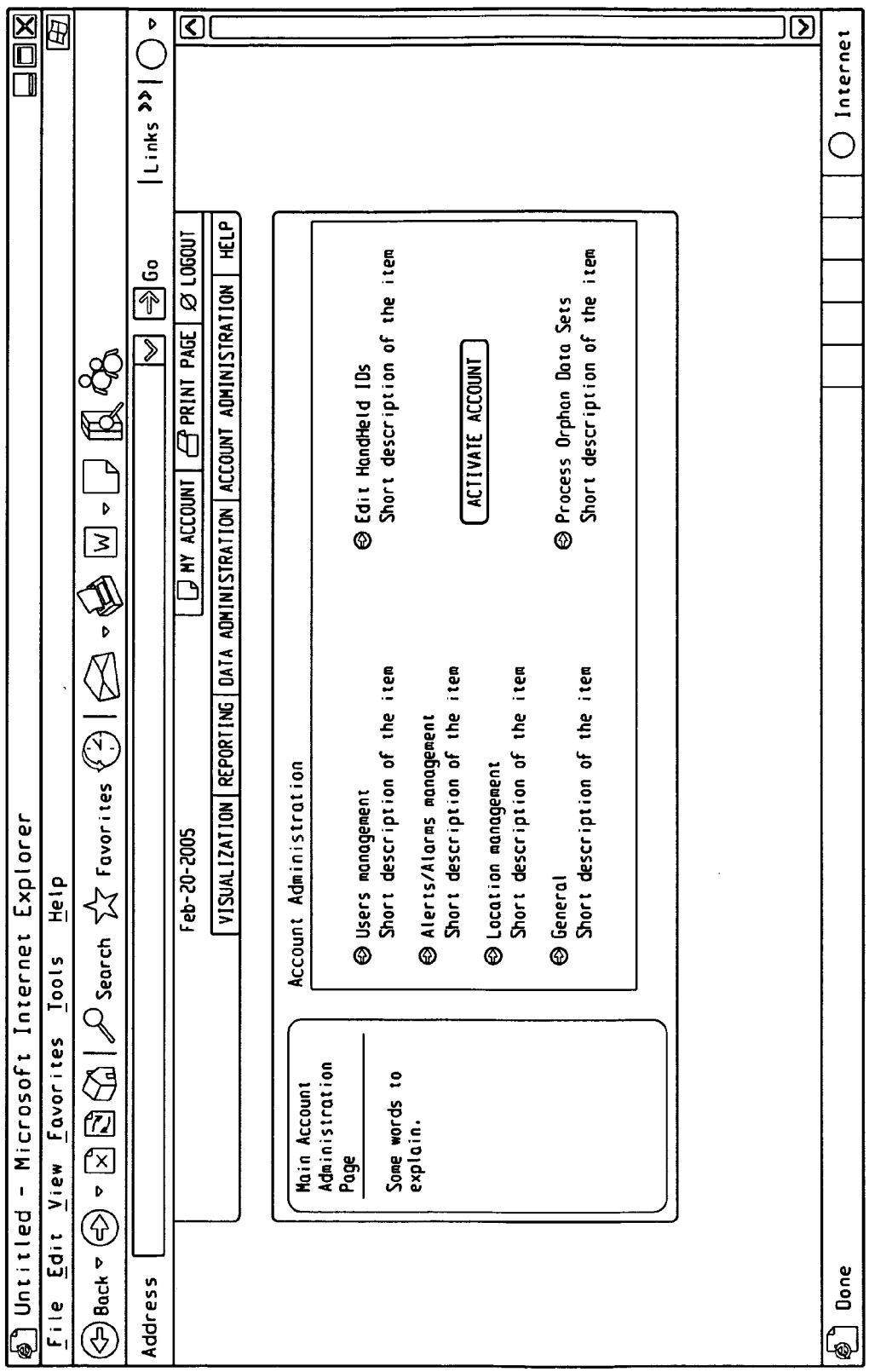
Figure 11B:
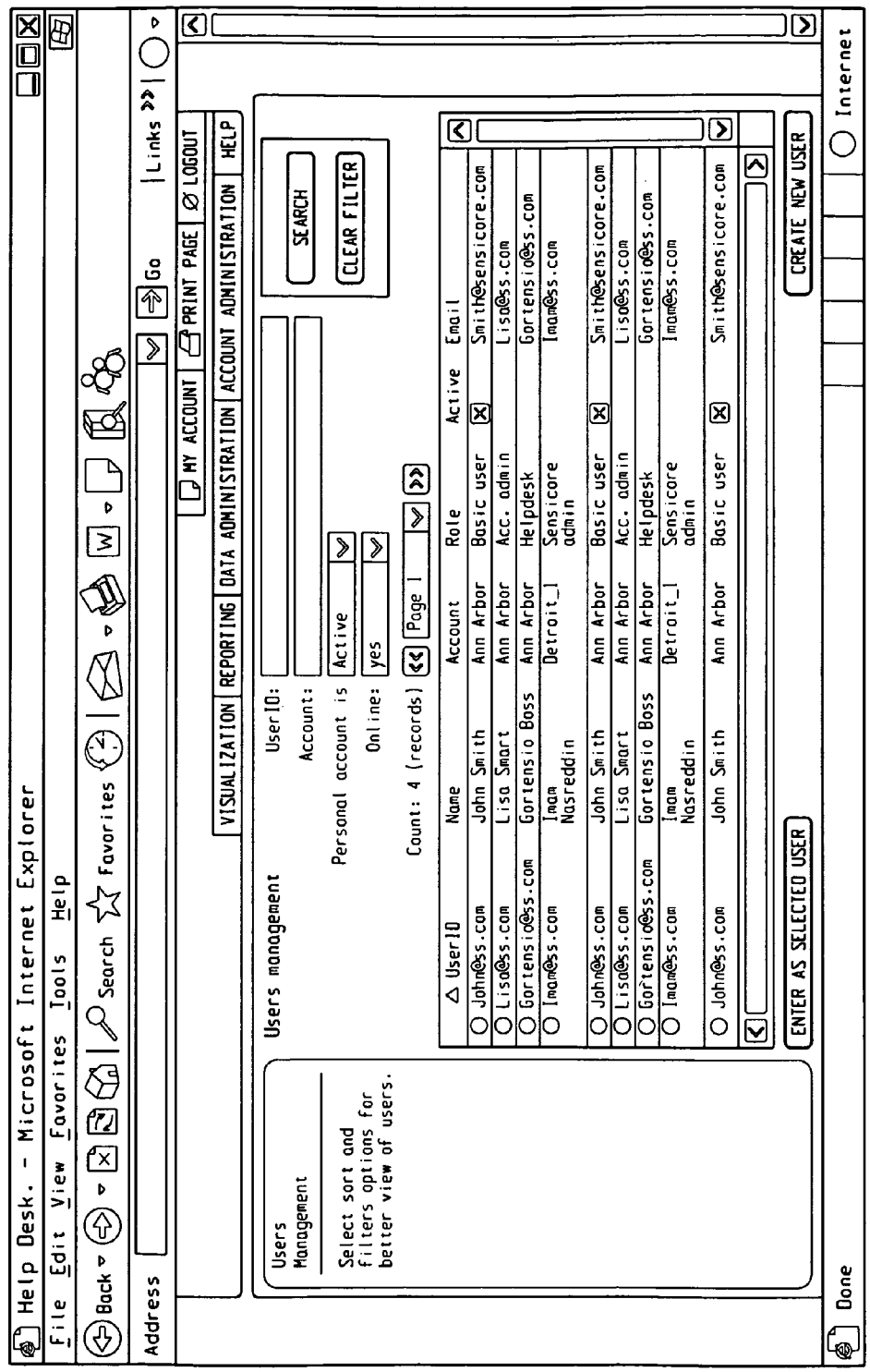
Figure 11C:
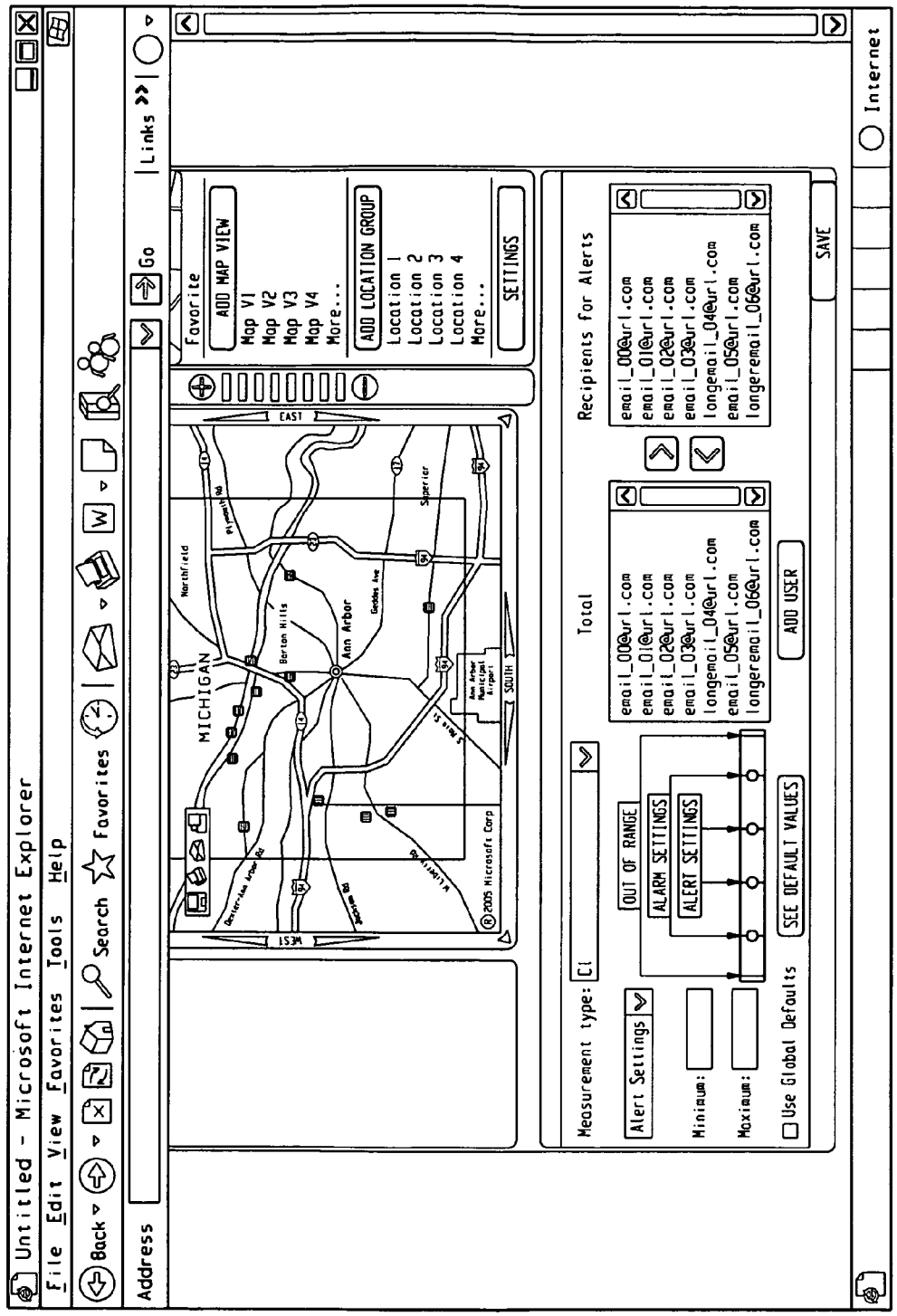
Figure 11D:
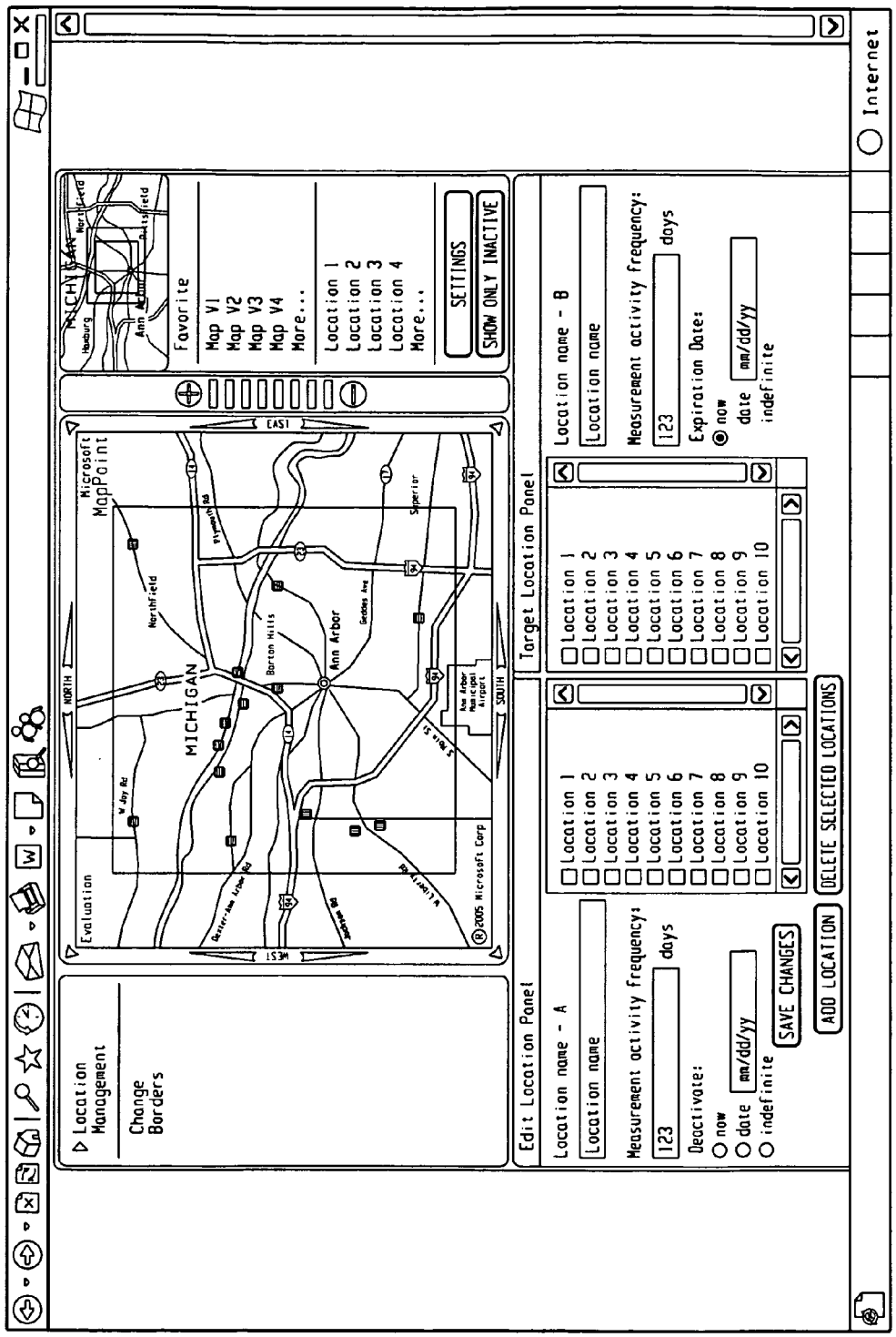
Figure 11E:
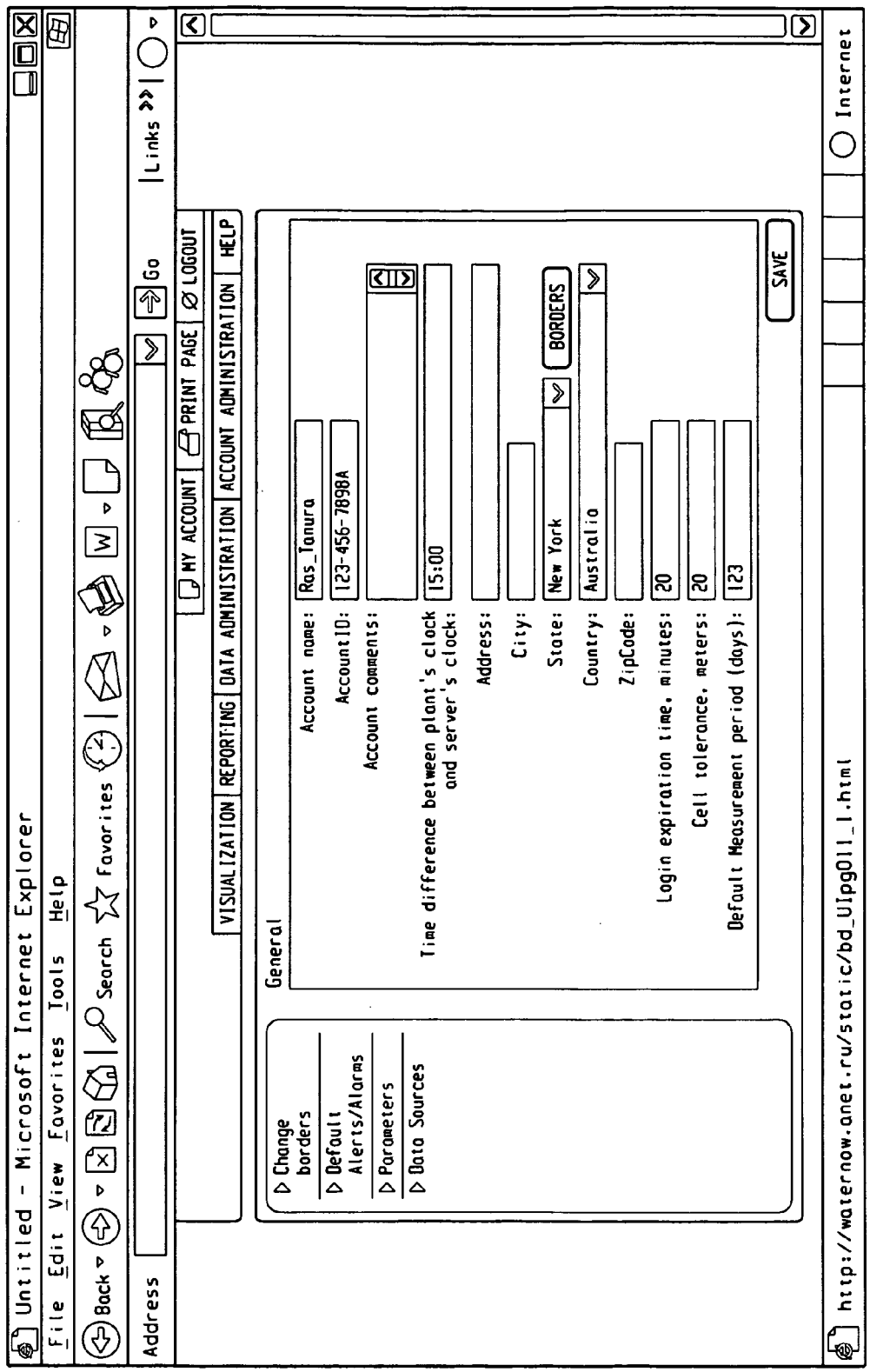
Figure 11F:
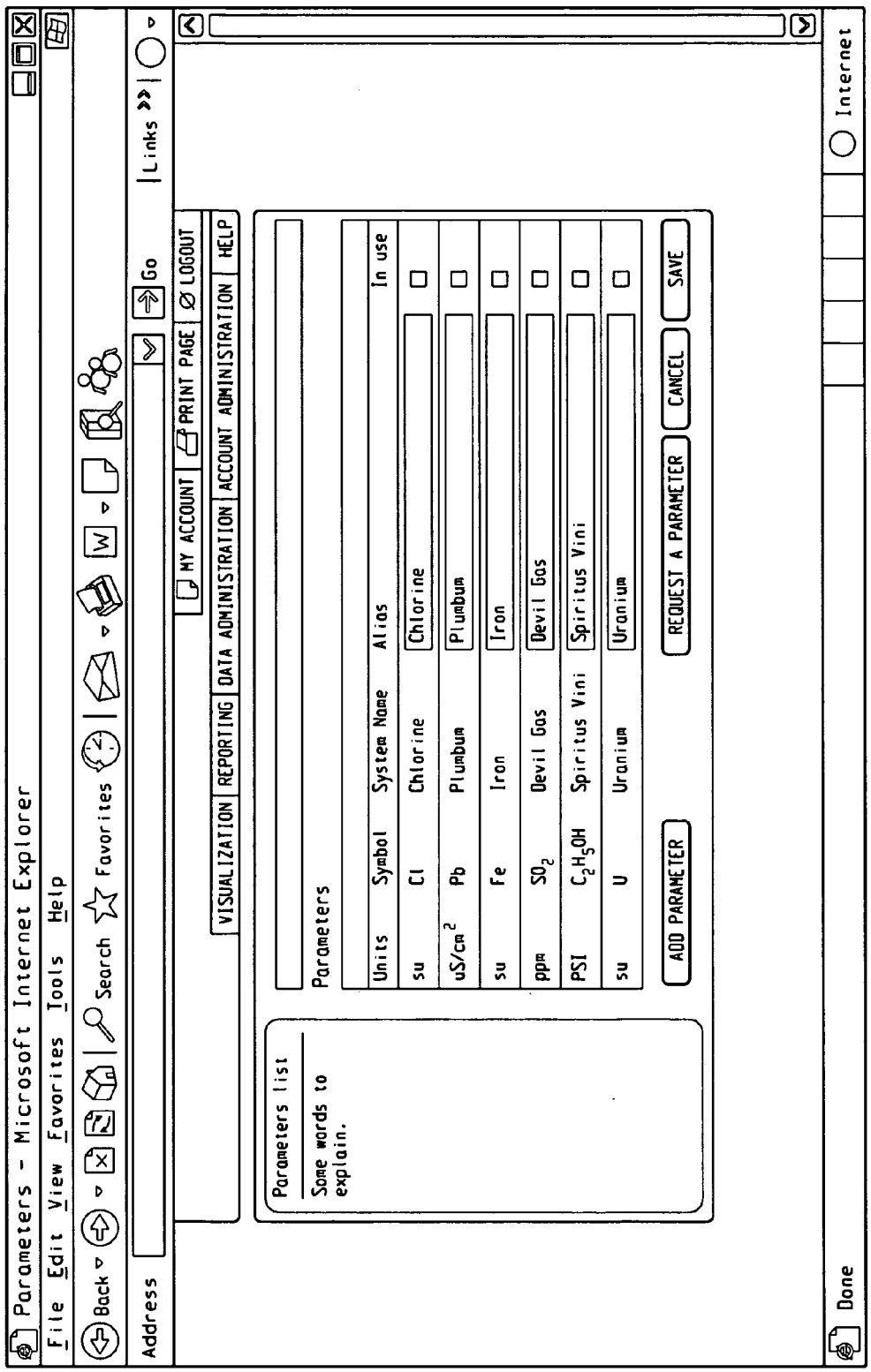
Figure 11G:
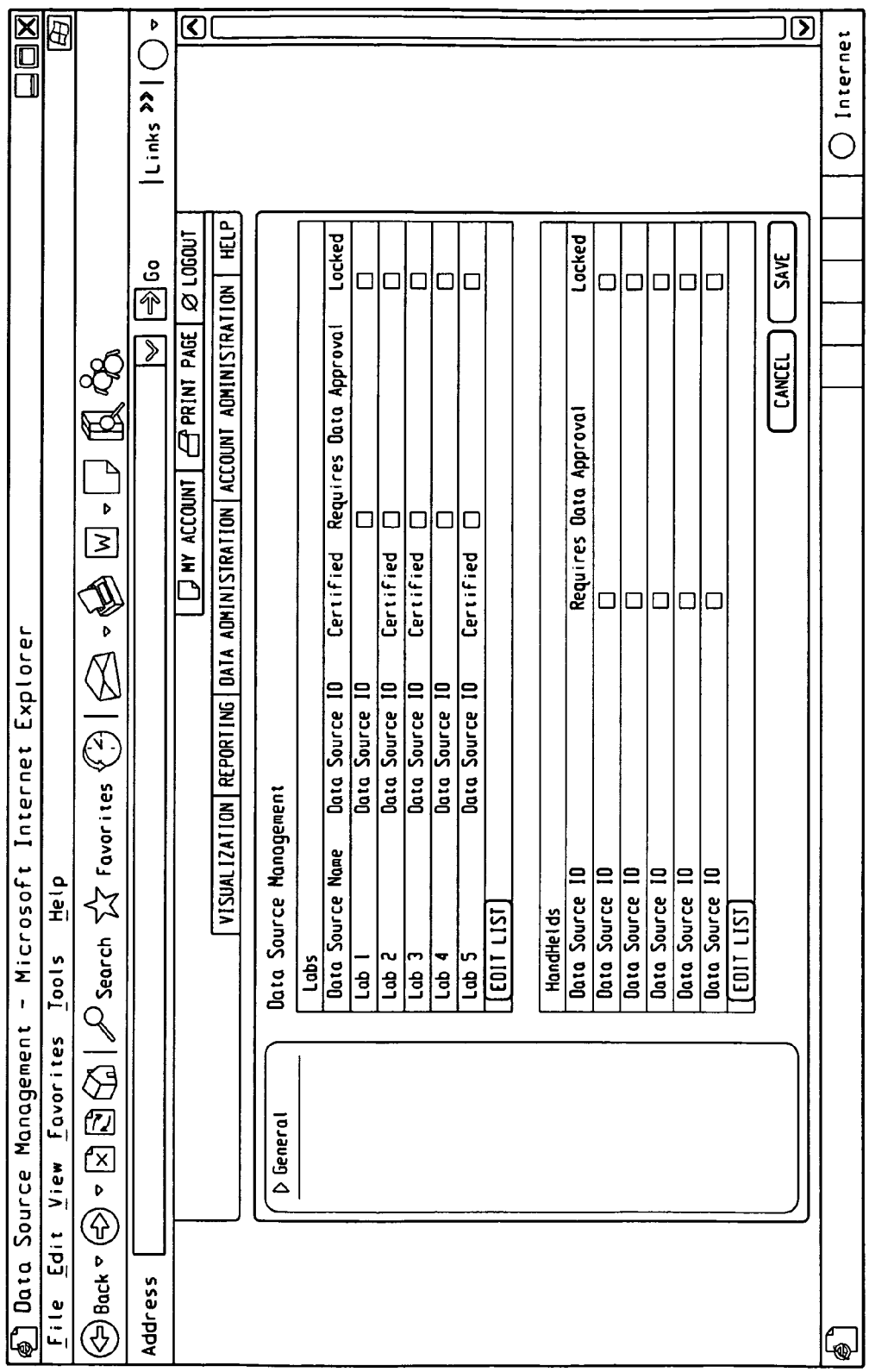

Referring back to the main page shown in FIG. 8A, if the ACCOUNT ADMINISTRATION link at the top of the page is clicked, a screen such as shown in FIG. 11A is displayed. This screen includes a link for "Users Management", clicking on which allows viewing a page such as shown in FIG. 11B, which allows viewing and editing information of users, as well as creating new users. Clicking the "Alerts/Alarms Management" link in FIG. 11A allows viewing a page such as shown in FIG. 11C, which shows a map as described previously and which allows setting alert, alarm, and normal range settings. This page also allows specifying which users will receive notifications (e.g., via e-mail, SMS, pager, etc.) for alarm and alert conditions. Clicking the "Location Management" link in FIG. 11A brings up the screen in FIG. 11D, which allows creating new locations at which data will be measured, specifying the measurement frequency for a given location, as well as any expiration date. Also borders of a given region to view can be set using the "Change Borders" link and dragging appropriate location bars. Clicking on the "General" tab brings up a page shown in FIG. 11E, which allows viewing, specifying and/or editing particular information about a given account. Clicking the "Parameters" link in FIG. 11E, brings up the screen shown in FIG. 11F, which allows specifying parameters to be displayed as defaults when locations are selected on a map with a cursor, for example, and specifying alias names for certain parameters. Clicking the "Data Sources" link shown in FIG. 11E, brings up the screen shown in FIG. 11G, which specifies how data from particular sources (e.g., handheld devices and/or outside laboratories) will be designated in terms of status. For example, some sources can be locked out, such that data from those sources is recorded but is not regarded as accepted data for general visualization, some sources can be flagged as needing approval before their data is accepted for general visualization, and some sources can be flagged as certified such that their data is accepted for visualization without approval.

An aspect that is reflected by the foregoing description is that the approach described herein, among other things, takes multiple steps to ensure the integrity of data that is measured and provided for access. Also, another aspect that implicates the integrity of the fluid test data is the fact that it can be measured by chip-based sensors without the need for significant human intervention and with excellent reproducibility. Thus, the errors often encountered in traditional water quality testing by individuals (e.g., errors in collected grab samples, laboratory errors by individuals in making wet chemistry measurements, etc.) are alleviated in a chip-based approach. Thus, even those who do not collect and/or analyze fluid test data themselves can have confidence in the accuracy and integrity of fluid test data gathered and shared as described herein. Moreover, fluid test data that is generated by sensors with unique identifiers recognized by the computer system 4 as well as fluid test data that has a source other than electronic sensors whose unique identifiers are known to the computer system 4 (e.g, laboratory-based analysis data generated by a laboratory from a sample taken from a known location such that the fluid test data is generated under the control of the laboratory) can be tracked by a chain of custody record (electronic or otherwise) associated with the sample to authenticate the integrity of the sample. For example, if such fluid test data is transmitted by a network to the computer system controlled by the service provider, information about the sample's chain of custody can also transmitted to the computer system controlled by the service provider. In the case of handheld sensors, the chain of custody information can include information pertaining to the GPS-recorded location.

As can be seen, the present disclosure has been explained by way of exemplary embodiments which it is not limited. Various modifications and alterations of the core concepts will occur to those skilled in the art without departing from the scope of the invention as articulated in the claims appended hereto. It is reiterated that advantages and attendant aspects of various embodiments of the invention are not necessarily part of the invention. Rather, the invention should be determined by a review of the claims appended hereto, as well as equivalents of the elements thereof.

It is further noted that the systems and methods may be implemented on various types of computer architectures, such as for example on a single general purpose computer or workstation, or on a networked system, or in a client-server configuration, or in an application service provider configuration.

It is further noted that the systems and methods may include data signals conveyed via networks (e.g., local area network, wide area network, internet, combinations thereof, etc.), fiber optic medium, carrier waves, wireless networks, etc. for communication with one or more data processing devices. The data signals can carry any or all of the data disclosed herein that is provided to or from a device.

Additionally, the methods and systems described herein may be implemented on many different types of processing devices by program code comprising program instructions that are executable by the device processing subsystem. The software program instructions may include source code, object code, machine code, or any other stored data that is operable to cause a processing system to perform methods described herein. Other implementations may also be used, however, such as firmware or even appropriately designed hardware configured to carry out the methods and systems described herein.

The systems' and methods' data (e.g., associations, mappings, etc.) may be stored and implemented in one or more different types of computer-implemented ways, such as different types of storage devices and programming constructs (e.g., data stores, RAM, ROM, Flash memory, flat files, databases, programming data structures, programming variables, IF-THEN (or similar type) statement constructs, etc.). It is noted that data structures describe formats for use in organizing and storing data in databases, programs, memory, or other computer-readable media for use by a computer program.

The systems and methods may be provided on many different types of computer-readable media including computer storage mechanisms (e.g., CD-ROM, diskette, RAM, flash memory, computer's hard drive, etc.) that contain instructions for use in execution by a processor to perform the methods' operations and implement the systems described herein.

The computer components, software modules, functions, data stores and data structures described herein may be connected directly or indirectly to each other in order to allow the flow of data needed for their operations. It is also noted that a module or processor includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Finally, as used in the description herein and throughout the claims that follow, the meanings of "and" and "or" include both the conjunctive and disjunctive and may be used interchangeably unless the context expressly dictates otherwise; the phrase "exclusive or" may be used to indicate situation where only the disjunctive meaning may apply.

What is claimed is:

1. A method of monitoring fluid quality, comprising the steps of:

receiving, by a computer system controlled by a service provider, first fluid test data generated by a first sensor unit controlled by first entity, wherein the first sensor unit is configured to establish communication with the computer system via one or more communication networks, and wherein the first fluid test data includes first location information identifying where the first fluid test data was taken, storing the first fluid test data, receiving, by the computer system controlled by the service provider, second fluid test data generated under the control a second entity different from the first entity, wherein the second fluid test data includes second location information identifying where the second fluid test data was taken, storing the second fluid test data permitting a first user authorized by the first entity to access aspects of the first fluid test data from the computer system controlled by the service provider via the Internet using a graphical computer interface at a first computer operated by the first user, and permitting a second user authorized by the second entity to access aspects of the second fluid test data from the computer system controlled by the service provider via the Internet using a graphical computer interface at a second computer operated by the second user, wherein permitting the access to the first user allows the first user to visualize first information associated with the first fluid test data overlaid on a geographical map displayed on the graphical computer interface of the first computer, and wherein permitting access to the second user allows the second user to visualize second information associated with the second fluid test data overlaid on a geographical map displayed on the graphical computer interface of the second computer.

2. The method of claim 1, comprising permitting an administrator affiliated with the first entity to grant permission to other individuals to visualize information associated with the first fluid test data via the Internet using respective graphical computer interfaces, wherein the other individuals are not affiliated with the first entity.

3. The method of claim 1, wherein the first sensor unit is a portable unit that comprises a global positioning system (GPS) unit and is configured to communicate with said one or more networks via wireless communication.

4. The method of claim 1, wherein the first sensor unit is a stationary sensor unit intended to have a fixed known location and which communicates with one or more networks.

5. The method of claim 1, wherein the second fluid test data is laboratory-based analysis data generated by a laboratory from a sample taken from a known location, wherein the second fluid test data is generated under the control of the laboratory, and wherein the second fluid test data is tracked by a chain of custody of the sample.

6. The method of claim 5, wherein, if the second fluid test data is transmitted by a network to the computer system controlled by the service provider, information about the sample's chain of custody is also transmitted to the computer system controlled by the service provider.

7. The method of claim 1, wherein the first fluid test data is water test data associated with potable water.

8. The method of claim 1, wherein the one or more communication networks include one or more networks selected from the group comprising wireless tower networks, wired networks, and combinations thereof.

9. The method of claim 1, wherein the first and second fluid test data include data selected from the group comprising physical properties data, chemical properties data, biological properties data, radiological properties data, and combinations thereof.

10. The method of claim 1, wherein the first sensor unit is a portable unit that comprises a global positioning system (GPS) unit or is a stationary sensor unit intended to have a fixed known location;

wherein the first sensor unit transmits a unique identifier that has been registered with the computer system along with the first fluid test data.

11. The method of claim 10, wherein the geographical map displayed on the graphical computer interface of the first computer includes a location indicator of the first sensor unit.

12. The method of claim 1, comprising paying consideration to the first entity in exchange for access to the first fluid test data that was generated by the first sensor unit.

13. The method of claim 1, wherein the first fluid test data is provided by a laboratory information management system or a supervisory control and data acquisition system or a public Environmental Protection Agency database.

14. The method of claim 1, comprising:
receiving additional data that is overlaid on the geographical map along with the first fluid test data on the graphical computer interface of the first computer;
wherein the additional data includes medical data, weather data, historical environmental data, or combinations thereof.

15. The method of claim 1, comprising:
receiving additional data that is overlaid on the geographical map along with the first fluid test data on the graphical computer interface of the first computer;
wherein the additional data includes municipal test data, industrial test data, commercial test data, or combinations thereof; wherein an aggregate test data layer display is generated by the overlaying of the additional data on the geographical map along with the first fluid test data.

16. The method of claim 1, comprising receiving a user interactive map command for manipulating the geographical map.

17. The method of claim 16, wherein the user interactive map command includes a map zoom in command or a map zoom out command.

18. The method of claim 1, comprising displaying fluid test parameters for selection by the first user;
wherein a graph is displayed of the selected parameters.

19. The method of claim 18, comprising defining one or more additional parameters that are derived from the first fluid test data;
wherein the defined one or more additional parameters are displayed on the graph.

20. The method of claim 18, comprising displaying sensor locations for selection by the first user;
wherein the graph is displayed of the selected parameters for the selected sensor locations.

21. The method of claim 20, comprising receiving a selection of a displayed sensor location;
providing to the first user information regarding the selected sensor location.

22. The method of claim 21, wherein the information regarding the selected sensor location includes information about longitude and latitude, operator of the sensor, date and time of the last test, and a listing of the values for the selected parameters from the last test.

23. The method of claim 1, comprising defining alert and alarm thresholds through the graphical computer interface of the first computer;
displaying data on the geographical map that correspond to a defined threshold.

24. The method of claim 23, comprising displaying data on the geographical map that corresponds to a defined normal threshold;
wherein a notification is sent to one or more predefined entities if an alert or alarm threshold is satisfied.

25. The method of claim 1, comprising displaying contoured lines on the geographical map to indicate equal concentrations of a selected parameter.

26. The method of claim 25, comprising generating an outline of a hot spot on the geographical map.

27. The method of claim 1, comprising displaying colored contoured lines on the geographical map to indicate equal concentrations of a selected parameter.

28. The method of claim 27, wherein the colored contoured lines provide the ability for the first user to see a parameter-concentration distribution for an entire area using one chart, instead of having to process multiple charts to gain a similar appreciation for the distribution.

29. The method of claim 1, wherein the first sensor unit transmits a unique identifier that has been registered with the computer system along with the first fluid test data;
using the unique identifier and a chain of custody record associated with a sample to determine chain of custody for the sample.

30. A system of monitoring fluid quality, comprising:
a computer system controlled by a service provider, configured to receive first fluid test data generated by a first sensor unit controlled by first entity, wherein the first sensor unit is configured to establish communication with the computer system via one or more communication networks, and wherein the first fluid test data includes first location information identifying where the first fluid test data was taken,
wherein the computer system is configured to receive second fluid test data generated under the control a second entity different from the first entity, wherein the second fluid test data includes second location information identifying where the second fluid test data was taken,
a data store for storing the first and second fluid test data,
software instructions configured to permit a first user authorized by the first entity to access aspects of the first fluid test data from the computer system controlled by the service provider via the Internet using a graphical computer interface at a first computer operated by the first user, and
said software instructions permitting a second user authorized by the second entity to access aspects of the second fluid test data from the computer system controlled by the service provider via the Internet using a graphical computer interface at a second computer operated by the second user,
wherein said permitting of the access to the first user is for allowing the first user to visualize first information associated with the first fluid test data overlaid on a geographical map displayed on the graphical computer interface of the first computer, and
wherein said permitting of the access to the second user is for allowing the second user to visualize second information associated with the second fluid test data overlaid on a geographical map displayed on the graphical computer interface of the second computer.

31. The system of claim 30, comprising wherein the software instructions are configured to permit an administrator affiliated with the first entity to grant permission to other individuals to visualize information associated with the first fluid test data via the Internet using respective graphical computer interfaces, wherein the other individuals are not affiliated with the first entity.

32. The system of claim 30, wherein the first sensor unit is a portable unit that comprises a global positioning system (GPS) unit and is configured to communicate with said one or more networks via wireless communication.

33. The system of claim 30, wherein the first sensor unit is a stationary sensor unit intended to have a fixed known location and which communicates with one or more networks.

34. The system of claim 30, wherein the second fluid test data is laboratory-based analysis data generated by a laboratory from a sample taken from a known location, wherein the second fluid test data is generated under the control of the laboratory, and wherein the second fluid test data is tracked by a chain of custody of the sample.

35. The system of claim 34 wherein, if the second fluid test data is transmitted by a network to the computer system controlled by the service provider, information about the sample's chain of custody is also transmitted to the computer system controlled by the service provider.

36. A graphical user interface for monitoring fluid quality, comprising:
 a geographical map;
 a display of fluid test data that is overlaid on the geographical map, wherein the fluid test data was generated by a sensor unit;
 contoured lines overlaid on the geographical map to indicate equal concentrations of a fluid test parameter;
 a selection region configured to permit a user to select fluid test parameters;
 a graph region for displaying a graph of fluid test parameters selected by the user via the selection region.

37. The graphical user interface of claim 36, wherein the geographical map includes a location indicator of the sensor unit.

38. The graphical user interface of claim 36, wherein the graphical user interface is configured to receive a user interactive map command for manipulating the geographical map.

39. The graphical user interface of claim 36, wherein one or more additional parameters that are derived from the fluid test data are defined; and wherein the defined one or more additional parameters are displayed on the graph of the selected fluid test parameters.

40. The graphical user interface of claim 36, further comprising a sensor selection region displaying sensor locations that is configured to permit the user to select sensor locations; wherein the graph of fluid test parameters displays the selected fluid test parameters for the selected sensor locations.

41. The graphical user interface of claim 36, further comprising an outline of a hot spot on the geographical map.

42. The graphical user interface of claim 36, wherein the contoured lines on the geographical map to indicate equal concentrations of a selected parameter are colored contoured lines.

43. The graphical user interface of claim 42, wherein the colored contoured lines provide the ability for the user to see a parameter-concentration distribution for an entire area using one chart, instead of having to process multiple charts to gain a similar appreciation for the distribution.

* * * * *